(12) United States Patent
Smith et al.

(10) Patent No.: US 11,896,870 B2
(45) Date of Patent: Feb. 13, 2024

(54) DEVICES AND METHODS FOR EXERCISE OR ANALYSIS OF THE NECK REGION

(71) Applicant: NECK TRONICS INC., Conquerall (CA)

(72) Inventors: William Smith, Bridgewater (CA); Petrus Haase, Conquerall Mills (CA)

(73) Assignee: NECK TRONICS INC., Conquerall (CA)

( * ) Notice: Subject to any disclaimer, the term of this patent is extended or adjusted under 35 U.S.C. 154(b) by 0 days.

(21) Appl. No.: 17/190,910

(22) Filed: Mar. 3, 2021

(65) Prior Publication Data

US 2021/0268332 A1 Sep. 2, 2021

Related U.S. Application Data

(63) Continuation of application No. 16/347,212, filed as application No. PCT/CA2017/051088 on Sep. 15, 2017, now abandoned.
(Continued)

(51) Int. Cl.
*A63B 23/025* (2006.01)
*A61B 5/11* (2006.01)
(Continued)

(52) U.S. Cl.
CPC .......... *A63B 23/025* (2013.01); *A61B 5/1122* (2013.01); *A61B 5/22* (2013.01);
(Continued)

(58) Field of Classification Search
CPC ............................. A63B 23/025; A61H 1/0296
See application file for complete search history.

(56) References Cited

U.S. PATENT DOCUMENTS

| | | | |
|---|---|---|---|
| 4,768,779 A | 9/1988 | Oehman, Jr. | |
| 4,845,987 A | 7/1989 | Kenneth | |

(Continued)

FOREIGN PATENT DOCUMENTS

| | | |
|---|---|---|
| DE | 202006008550 U1 | 8/2006 |
| DE | 102008025601 B3 | 1/2010 |

(Continued)

OTHER PUBLICATIONS

International Search Report for PCT/CA2017/051088, dated Dec. 19, 2017.
(Continued)

*Primary Examiner* — Nyca T Nguyen
(74) *Attorney, Agent, or Firm* — Schmeiser, Olsen & Watts, LLP

(57) ABSTRACT

Provided herein are devices and methods for analysis and/or exercise of a body region of a subject. Such devices may include a guide arm supported by a support frame; a receiving surface supported by the guide arm, the receiving surface for receiving input force from the subject; and a motor assembly in communication with the guide arm, the motor assembly controlling movement of the receiving surface based on received input force. Exercise and/or analysis methods described herein may include steps of instructing the subject to apply an input force to a receiving surface; sensing the applied input force over time; and controlling movement of the receiving surface based on the received input force using a motor assembly, whereby the motor assembly moves the receiving surface in a pre-determined direction, so long as the input force remains within an allowable tolerance, until a pre-set end position is reached.

17 Claims, 41 Drawing Sheets

Related U.S. Application Data

(60) Provisional application No. 62/497,060, filed on Nov. 7, 2016.

(51) Int. Cl.
   *A61H 1/02* (2006.01)
   *A61B 5/22* (2006.01)
   *A61B 5/00* (2006.01)
   *A63B 21/02* (2006.01)

(52) U.S. Cl.
   CPC ......... *A61B 5/6822* (2013.01); *A61H 1/0296* (2013.01); *A61H 2001/0207* (2013.01); *A61H 2205/04* (2013.01); *A63B 21/02* (2013.01)

(56) References Cited

U.S. PATENT DOCUMENTS

| | | | |
|---|---|---|---|
| 4,893,808 A | 1/1990 | McIntyre | |
| 5,336,138 A | 8/1994 | Arjawat | |
| 6,454,680 B1 | 9/2002 | Taimela | |
| 6,551,214 B1 | 4/2003 | Taimela | |
| 6,692,451 B2 | 2/2004 | Splane, Jr. | |
| 7,104,926 B2 | 9/2006 | Carlson | |
| 8,038,588 B2 | 10/2011 | Hobson | |
| 8,636,631 B2 * | 1/2014 | Carlson | A63B 21/222 482/79 |
| 2003/0028130 A1 | 2/2003 | Wunderly | |
| 2003/0115954 A1 | 6/2003 | Vladimir | |
| 2004/0033869 A1 | 2/2004 | Carlson | |
| 2004/0220500 A1 * | 11/2004 | Dahl | A61H 1/0218 601/25 |
| 2007/0055190 A1 | 3/2007 | Bonutti et al. | |
| 2007/0272010 A1 * | 11/2007 | O'Leary | A63B 23/025 73/379.01 |
| 2008/0058164 A1 | 3/2008 | Douglas | |
| 2011/0152711 A1 | 6/2011 | Della Santina et al. | |
| 2012/0035512 A1 * | 2/2012 | Su | A63B 21/4035 601/5 |
| 2012/0108394 A1 | 5/2012 | Jones | |
| 2012/0232438 A1 * | 9/2012 | Cataldi | A63B 21/4045 601/5 |
| 2012/0253241 A1 | 10/2012 | Levital et al. | |
| 2014/0094721 A1 * | 4/2014 | Diallo | A63B 24/0087 601/5 |
| 2015/0290072 A1 | 10/2015 | Singhal | |
| 2016/0038811 A1 | 2/2016 | Lagier et al. | |
| 2016/0101011 A1 * | 4/2016 | Swenson | A61H 1/0296 482/10 |
| 2016/0213551 A1 | 7/2016 | Budagher | |
| 2016/0243396 A1 | 8/2016 | Taylor et al. | |
| 2020/0222754 A1 * | 7/2020 | Walker | A63B 21/00192 |

FOREIGN PATENT DOCUMENTS

| | | |
|---|---|---|
| KR | 101282485 B1 | 7/2013 |
| KR | 101506278 B1 | 3/2015 |
| WO | 2013140406 A1 | 9/2013 |

OTHER PUBLICATIONS

Written Opinion for PCT/CA2017/051088, dated Dec. 19, 2017.
European Extended Search Report dated May 11, 2020 for Application No. 17866679.8.
Non-Final Office Action dated Sep. 4, 2020 for U.S. Appl. No. 16/347,212.

* cited by examiner

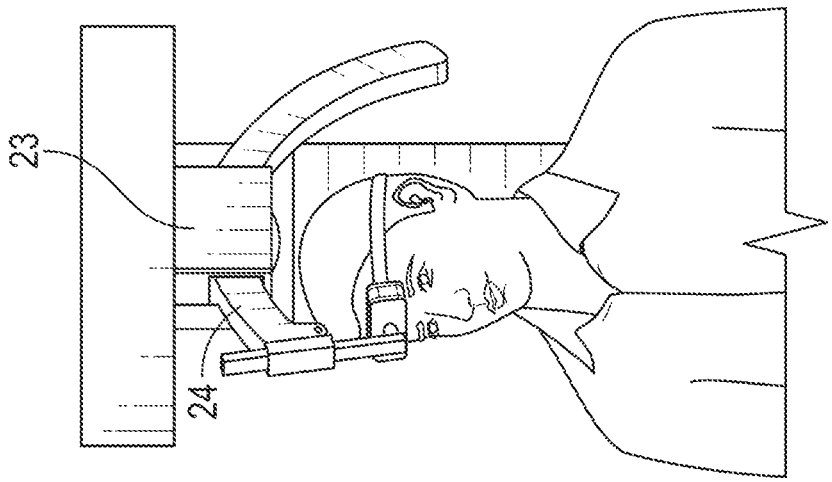
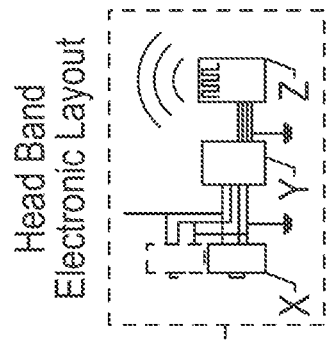
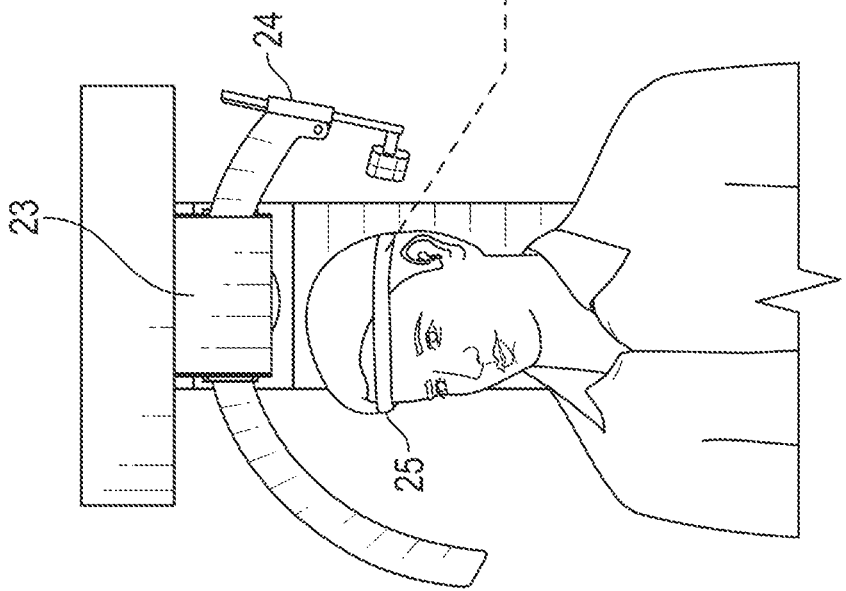
FIG. 20B
FIG. 20A

DEVICES AND METHODS FOR EXERCISE OR ANALYSIS OF THE NECK REGION

CROSS-REFERENCE TO RELATED APPLICATIONS

This application is a continuation application of U.S. application Ser. No. 16/347,212, filed May 3, 2019, and entitled "DEVICES AND METHODS FOR EXERCISE OR ANALYSIS OF THE NECK REGION," which claims priority to PCT Application No. PCT/CA2017/051088, having a filing date of Sep. 15, 2017, which is based on U.S. Provisional Application No. 62/497,060, having a filing date of Nov. 7, 2016. The entire contents of all priority documents are hereby incorporated by reference.

FIELD OF TECHNOLOGY

The following relates generally to exercise and analytical devices, and methods for exercising or analyzing a body region. More specifically, the following relates to devices and methods for analysis and/or exercise of a neck region or other joint mechanics of a subject.

BACKGROUND

Proper analysis/diagnosis of muscle injury, and proper exercise of affected muscles, is key to effective rehabilitation following injury, and in treatment of various conditions affecting the musculoskeletal system.

Due to the high prevalence of whiplash and other such traumas, injuries to the head and neck region are common examples of musculoskeletal injuries in need of analysis and rehabilitative treatment. Indeed, Whiplash Associated Disorders (WAD) and concussions are important problems in the medical field. Unfortunately, the musculoskeletal system of the neck region is complex, and development of reliable targeted analysis of injury and range of motion, as well as effective targeted neck rehabilitative exercise apparatus, has proven difficult.

Typical neck exercises for improving neck muscle strength include static (i.e. isometric) exercises, and dynamic (i.e. isokinetic) exercises. Neck exercise devices for strengthening neck muscles have been developed in the field. Such devices are typically operable to apply force to the head of a person. Conventionally, this force is generated by elastic means or an elastic force generator (i.e. by springs, or tensile bands), weights (i.e. by a suspended mass), or by resistance means or resistor (i.e. shock absorbers which resist motion of the head when pressed). Such devices suffer certain disadvantages, however.

By way of example, in many cases the direction of force applied by the device is uncontrolled or poorly controlled, and thus does not allow for effective targeting of particular neck muscle(s) during exercise or analysis. It is also common for the magnitude of the force applied by the devices to vary throughout the range of motion of the exercise, particularly where elastic means or elastic force generator such as a progressive spring are used to generate force. Further, conventional force generation means or force generator of conventional exercise devices generally produce force in certain limited directions. As well, conventional devices typically do not provide the subject with feedback regarding the subject's performance of the exercise, limiting the overall effectiveness of the exercise.

As conventional neck exercise devices generate force/resistance using elastics, weights, resistance means (resistor), or other such components, these devices are typically not designed to allow for force on the subject during use to be eliminated immediately, thus posing a potential safety hazard. If, for example, the subject "gives up" and ceases to exert effort mid-stroke during exercise, the developed or "loaded" force in the elastic/weight/resistance means (resistor) of the device can "snap back" the subject's head, potentially causing injury.

Alternative, additional, and/or improved devices and methods for analysis and/or exercise of the neck region and/or a body region and/or joint mechanics of a subject are desirable.

SUMMARY

An aspect relates to devices and methods for analysis and/or exercise of a body region of a subject which may allow for controlled application of force during use, protecting against "snap back" injury. Such devices and methods may provide isometric exercise, isokinetic exercise, or both, to the subject during use, and/or may allow for assessment of muscle function, range of motion, or both, of the subject during use. In certain embodiments, devices and methods provided herein may employ a motor assembly for controlling motion of a receiving surface with which the subject interacts during exercise and/or analysis, whereby the motor assembly controls the motion based on input force received from the subject at the receiving surface. The motor assembly may, for example, move the receiving surface away (or toward, depending on the configuration and/or application) from the subject in a direction substantially aligned with the subject's input force at a predetermined rate, so long as the input force remains within an allowable tolerance (i.e. above a predetermined force threshold value, for example), until a pre-determined end position is reached. In such manner, analysis and/or exercise of the subject may be carefully controlled and/or targeted. Furthermore, in certain embodiments, the motor assembly may be used to stop movement of the receiving surface immediately upon interruption of the input force, thereby protecting against "snap back" injury to the subject.

It is an aspect of embodiments of the present invention to provide devices and methods for analysis and/or exercise of, for example, the neck region.

In an embodiment, there is provided herein a device for analysis and/or exercise of a neck region of a subject, the device comprising:

a support frame;

a curved guide arm supported by the support frame;

a receiving surface supported by the curved guide arm, the receiving surface for receiving input force from the subject; and a motor assembly in communication with the curved guide arm, the motor assembly controlling movement of the receiving surface with respect to the subject based on input force received from the subject at the receiving surface.

In another embodiment of the above device, the receiving surface may be fixedly mounted to or integrated with the curved guide arm, and the motor assembly may be mounted to the support frame and control movement of the curved guide arm, such that movement of the receiving surface with respect to the subject is determined/regulated by movement of the curved guide arm by the motor assembly. In still another embodiment of the above device, the receiving surface may be movably mounted to the curved guide arm, and the motor assembly may be mounted to the curved guide arm and control movement of the receiving surface along the curved guide arm, such that movement of the receiving surface with respect to the subject is determined/regulated by movement of the receiving surface along the curved guide arm by the motor assembly.

In another embodiment of the above device or devices, the motor assembly may engage with the curved guide arm via one or more substantially non-slip complementary engagement members located on the motor assembly and curved guide arm.

In yet another embodiment of the above device or devices, the device may further comprise one or more input sensor(s) for sensing input force received from the subject at the receiving surface and transmitting a control signal based on the input force, and a controller for receiving the control signal and controlling action of the motor assembly based on the control signal. In still another embodiment, one or more of the input sensor(s) may be located at the receiving surface.

In another embodiment of the above device or devices, the motor assembly may be configured to drive the receiving surface in a direction substantially aligned with the input force (for example, away from the subject) at a predetermined rate, so long as the input force remains within an allowable tolerance (for example, above a minimum threshold, below a maximum threshold, or both). The motor may perform such action until, for example, a pre-determined end position for the receiving surface is reached.

In yet another embodiment of the above device or devices, the motor assembly may be configured to stop movement of the receiving surface with respect to the subject upon interruption of the input force from the subject upon the receiving surface, upon failure of the input force to remain within an allowable tolerance, or both. In still another embodiment, the allowable tolerance may comprise a lower threshold value for the input force to exceed, an upper threshold value for the input force to not exceed, an acceptable direction vector range for the input force to align within, or any combination thereof.

In still another embodiment of the above device or devices, the device may further comprise a positioning sensor which tracks location of the receiving surface, head positioning of the subject, or both, in 3D space.

In yet another embodiment of the above device or devices, the curved guide arm may be rotatable with respect to the support frame about a substantially vertical axis, allowing for positioning of the receiving surface about at least a portion of an outer perimeter region surrounding the subject.

In another embodiment of the above device or devices, the device may comprise a seat for the subject which orients the neck region of the subject with the receiving surface. By way of example, the seat, or the device itself, or both, may be height-adjustable to align with the subject's head or other body region during use.

In yet another embodiment of the above device or devices, the motor assembly may control movement of the receiving surface with respect to the subject to provide isometric exercise, isokinetic exercise, or both, to the subject during use; to assess range of motion of the subject during use; or a combination thereof.

In another embodiment of the above device or devices, the device may further comprise a user interface for guiding the subject's interaction with the receiving surface during use.

In still another embodiment of the above device or devices, the user interface may instruct the subject to apply input force to the receiving surface in a specific manner and provide the subject with real-time feedback allowing the subject to adjust application of input force so as remain within an allowable tolerance. In certain embodiments, the allowable tolerance may comprise a lower threshold value for the input force to exceed, an upper threshold value for the input force to not exceed, an acceptable direction vector range for the input force to align within, or any combination thereof.

In another embodiment of the above device or devices, the user interface may comprise a graphical interface displayed to the subject during use, an auditory interface played for the subject during use, or a combination thereof. In certain embodiments, the user interface may comprise a graphical user interface which provides an immersive visual experience to the subject during use which guides interaction of the subject with the receiving surface.

In another embodiment of the above device or devices, the device may comprise one or more sensors monitoring the position of the subject. By way of example, the device may comprise one or more sensors for monitoring the position of the back and/or shoulders of the subject during use. Such sensors may be used to, for example, verify that motion of the head against the receiving surface is being generated by muscles in the neck rather than tilting of the upper body (i.e., the sensors may monitor/verify that the subject's back and/or shoulders remain substantially stationary during use). In certain embodiments, such sensors may trigger a feedback signal (i.e. an audio or visual signal) for the subject if movement if improper movement of the back and/or shoulders is detected during use.

In another embodiment, there is provided herein a method for exercising or analyzing a neck region of a subject, the method comprising:
  instructing the subject to apply an input force to a receiving surface;
  sensing the input force applied to the receiving surface over time; and
  controlling movement of the receiving surface with respect to the subject based on the input force received from the subject at the receiving surface using a motor assembly,
  whereby the motor assembly drives or otherwise allows controlled movement of the receiving surface in a direction substantially aligned with the input force at a predetermined rate, so long as the input force remains within an allowable tolerance, thereby exercising or analyzing function of the neck region.

The motor may perform such action until, for example, a pre-determined end position for the receiving surface is reached.

In another embodiment of the above method, the motor assembly may stop movement of the receiving surface with respect to the subject upon sensed interruption of the input force from the subject upon the receiving surface, upon sensed failure of the input force to remain within the allowable tolerance, or both. In certain embodiments, the allowable tolerance may comprise a lower threshold value for the input force to exceed, an upper threshold value for the input force to not exceed, an acceptable direction vector range for the input force to align within, or any combination thereof.

In another embodiment of the above method or methods, the method may further comprise tracking location of the receiving surface, head positioning of the subject, or both, in 3D space over time.

In still another embodiment of the above method or methods, the motor assembly may control movement of the receiving surface with respect to the subject to provide isometric exercise, isokinetic exercise, or both, to the subject; to assess range of motion of the subject; or a combination thereof.

In yet another embodiment of the above method or methods, the instructing step may comprise providing a user interface guiding the subject's interaction with the receiving surface.

In another embodiment of the above method or methods, the user interface may instruct the subject to apply input force to the receiving surface in a specific manner and may provide the subject with real-time feedback allowing the subject to adjust application of input force so as remain within the allowable tolerance.

In yet another embodiment of the above method or methods, the user interface may comprise a graphical interface, an auditory interface, or a combination thereof.

In still another embodiment of the above method or methods, the user interface may comprise a graphical user interface which provides an immersive visual experience to the subject during use which guides interaction of the subject with the receiving surface.

In yet another embodiment of the above method or methods, the method may be performed using a device as defined hereinabove.

In another embodiment, there is provided herein a use of a device as defined hereinabove for performing analysis and/or exercise of a neck region of a subject.

In another embodiment of the above use, the device may be for use in performing a method as defined hereinabove.

BRIEF DESCRIPTION

Some of the embodiments will be described in detail, with references to the following Figures, wherein like designations denote like members, wherein:

FIG. 1 provides a perspective view of an embodiment of a device for analysis and/or exercise of a neck region of a subject;

Figure 5:
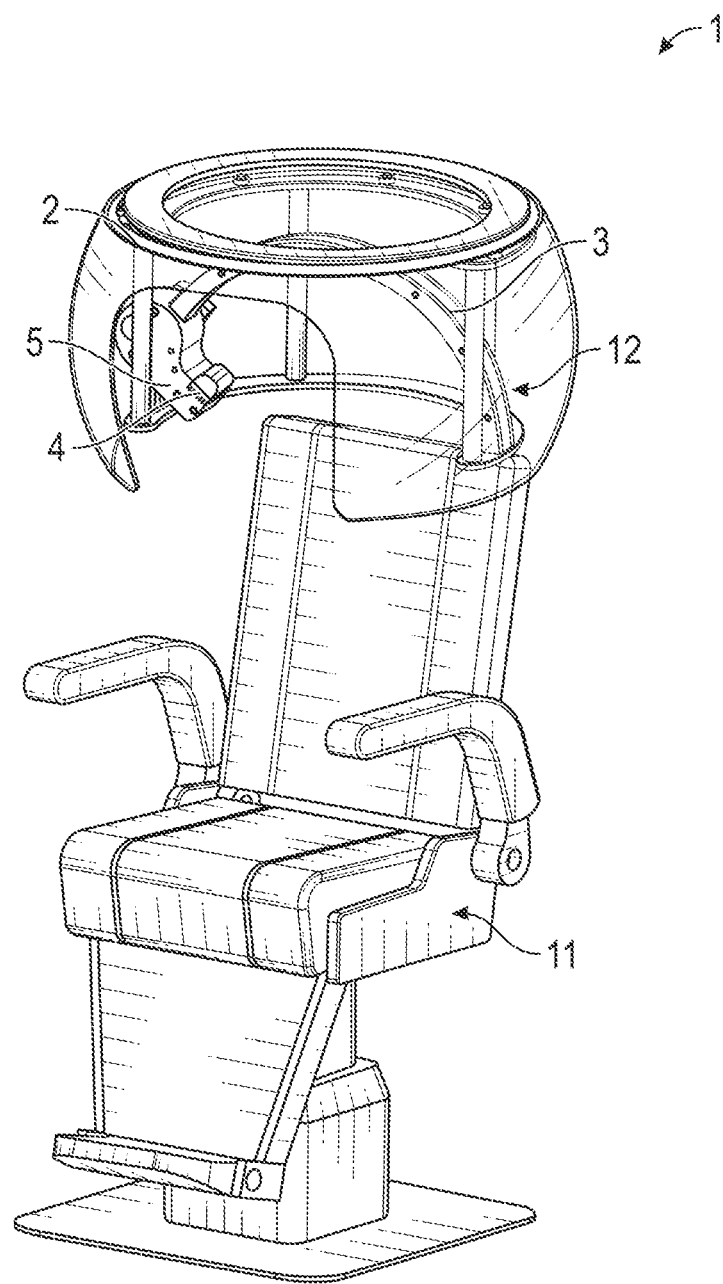
FIG. 5 shows a perspective view of another embodiment of a device for analysis and/or exercise of a neck region of a subject.
Figure 9A:
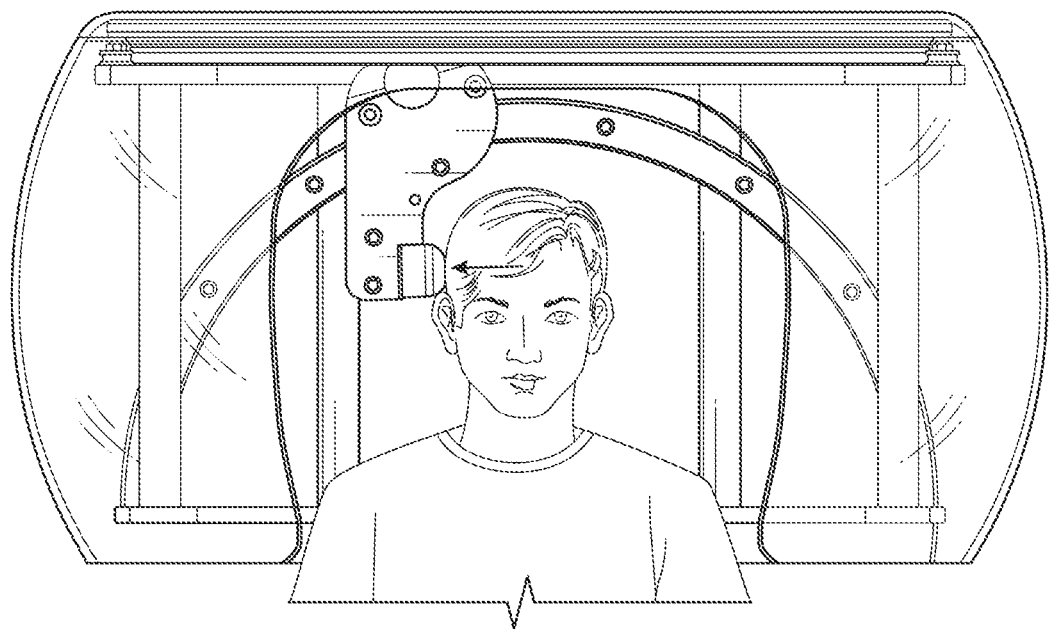
FIG. 9A shows a perspective view of a subject engaging with the receiving surface of the device embodiment of FIG. 5.
Figure 9B:
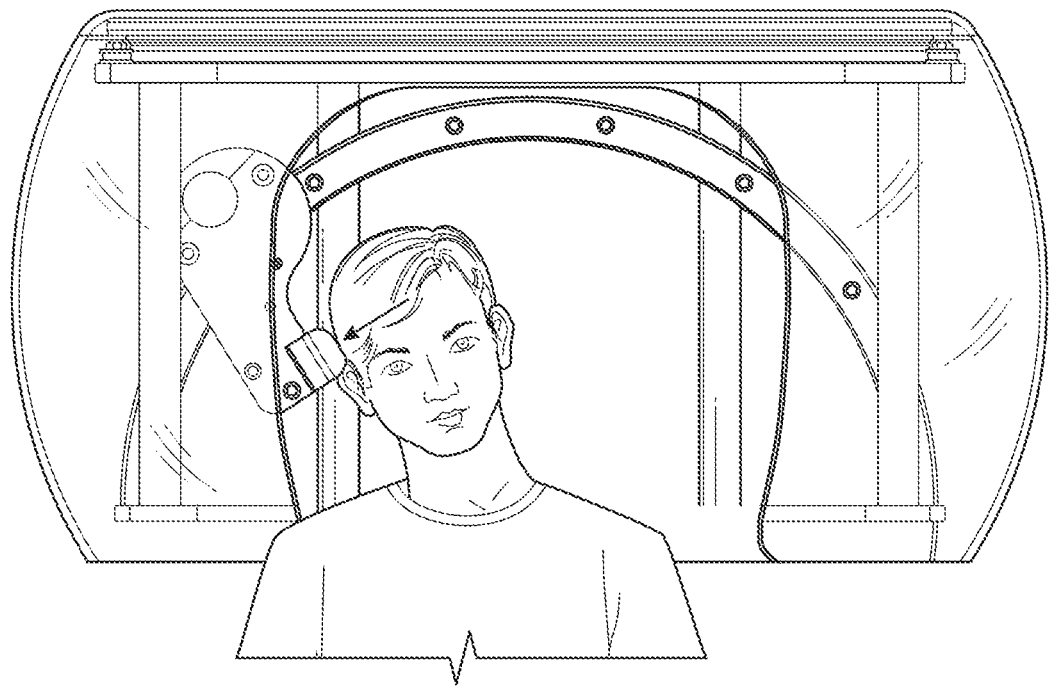
Figure 10:
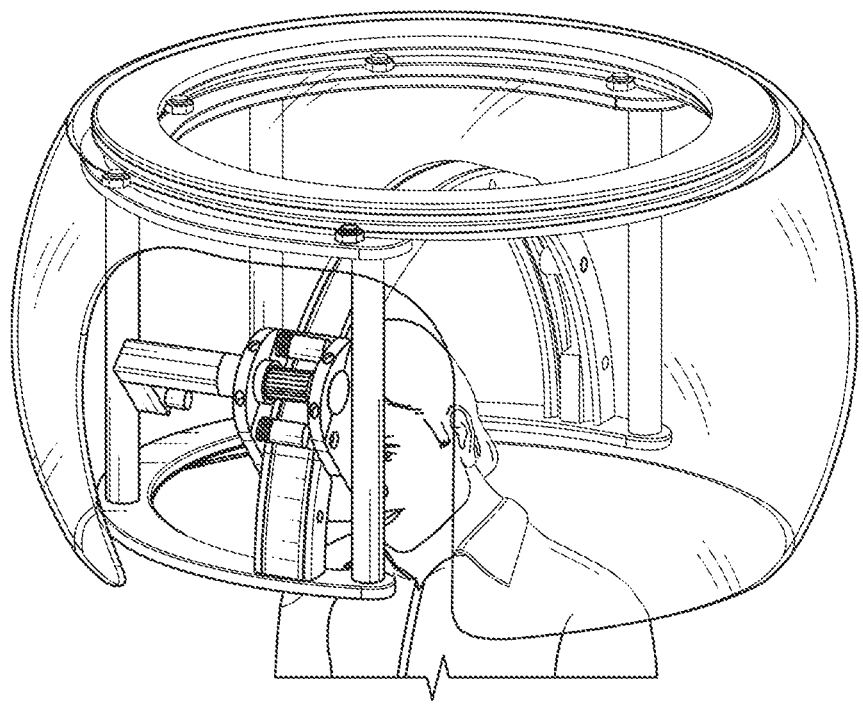
Figure 11A:
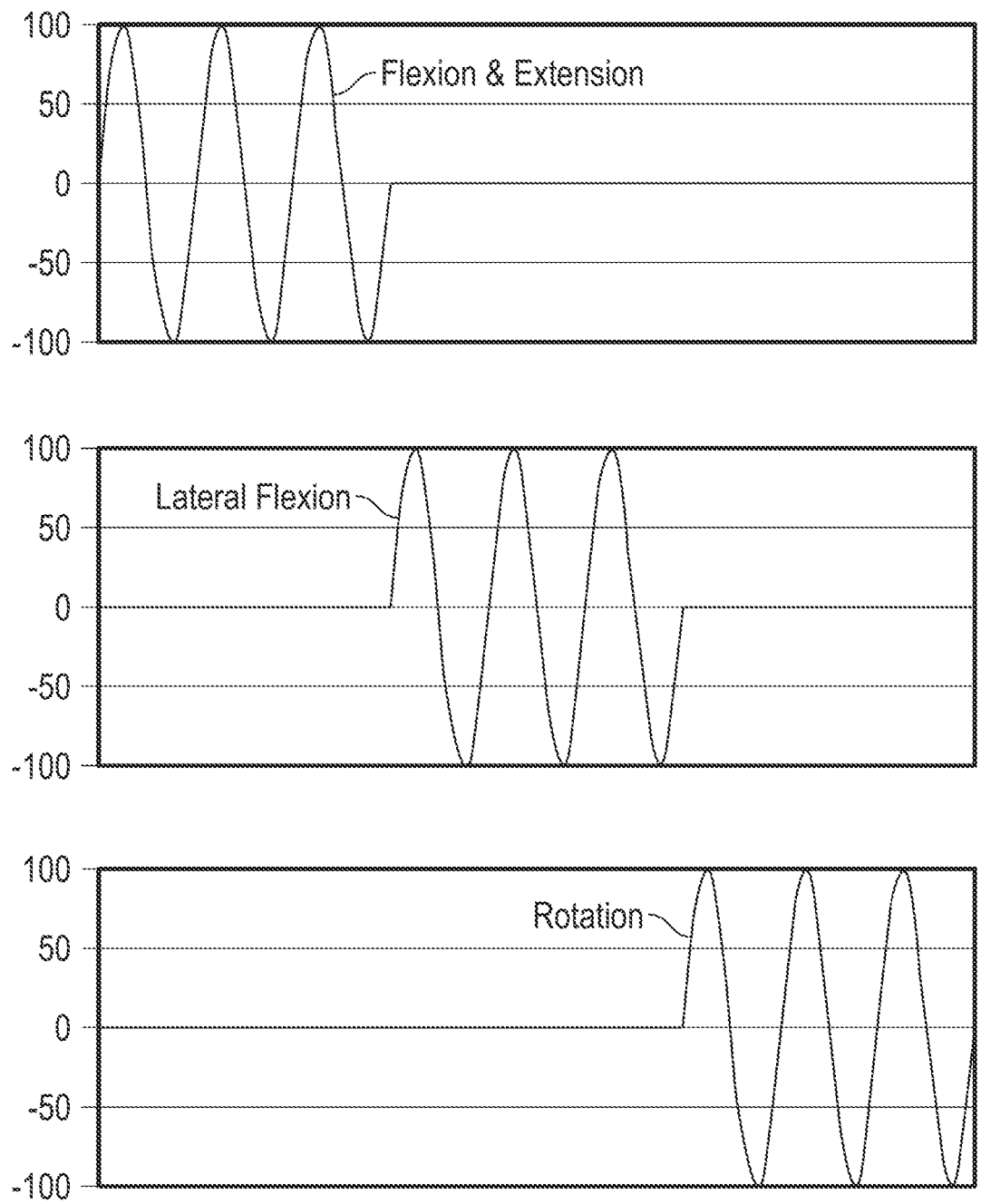
Figure 12A:
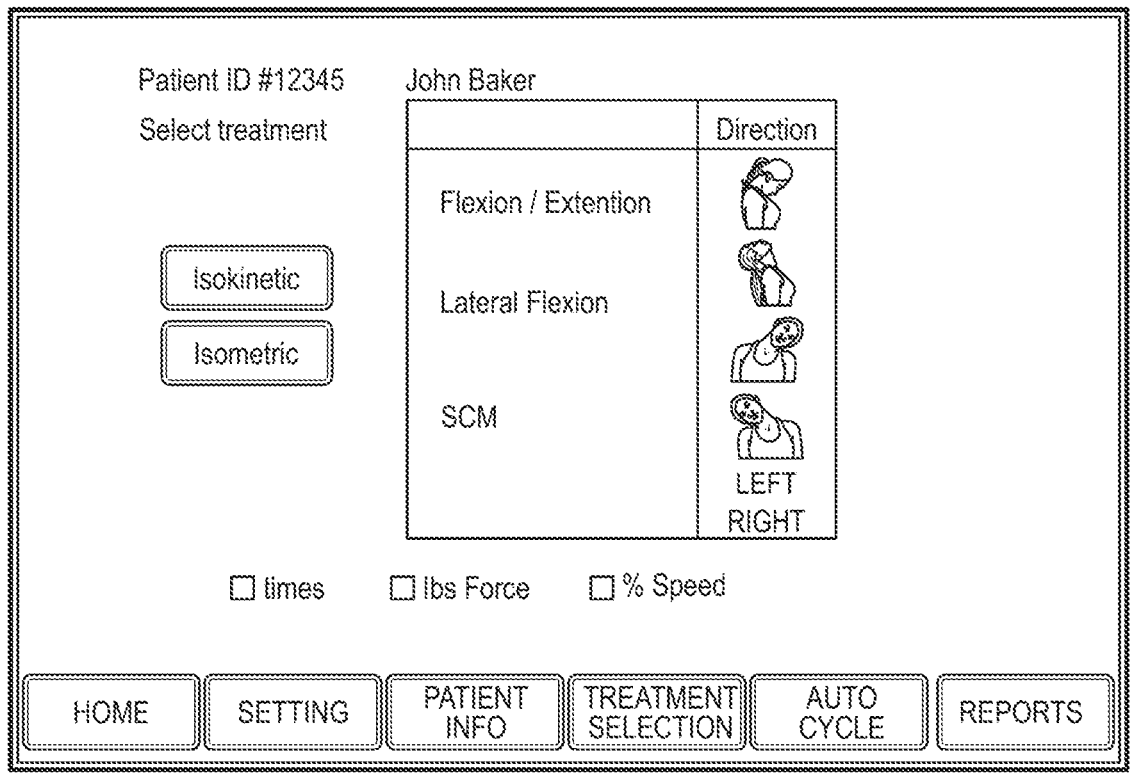
Figure 12B:
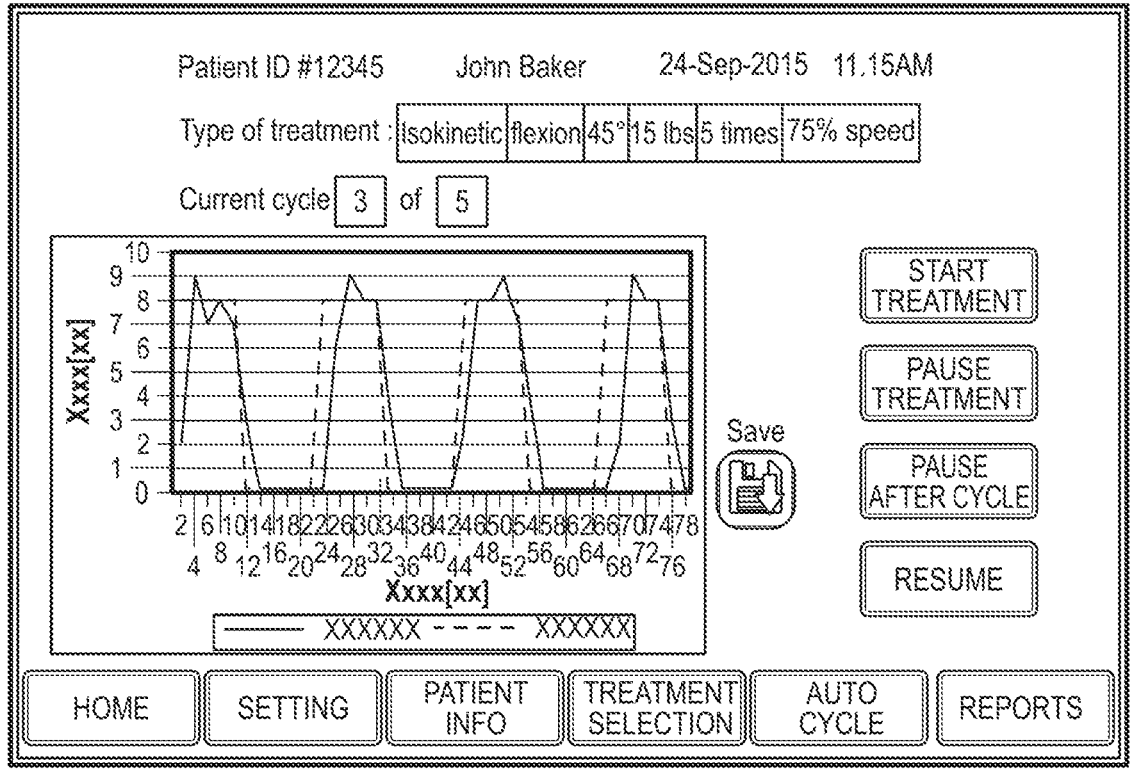
Figure 13:
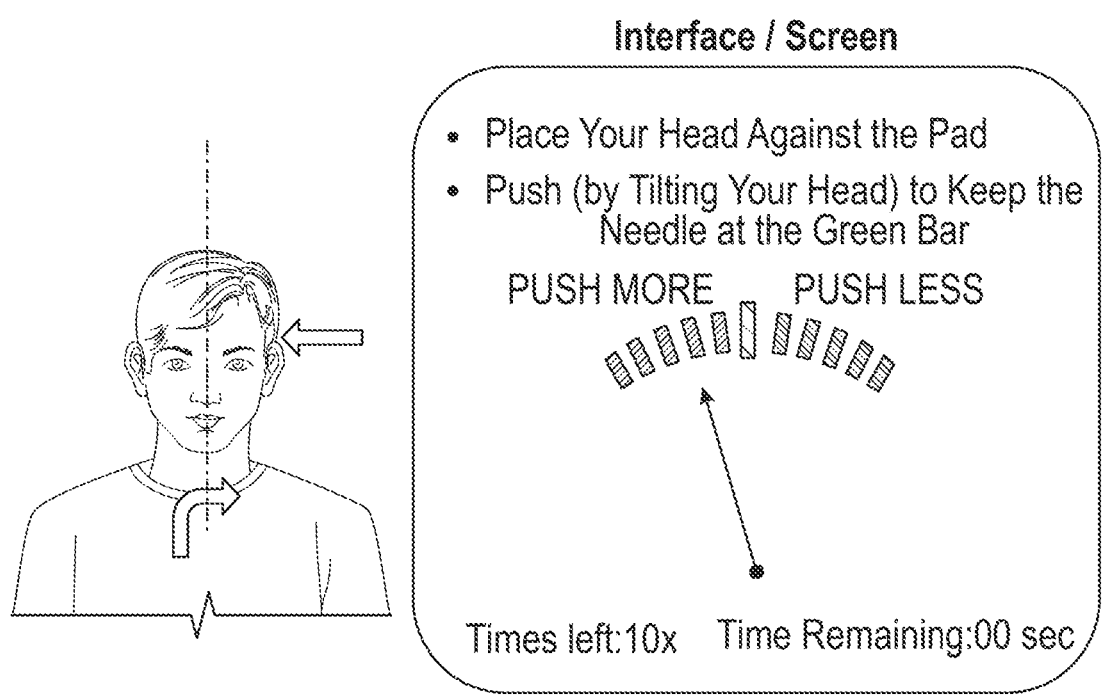
Figure 14:
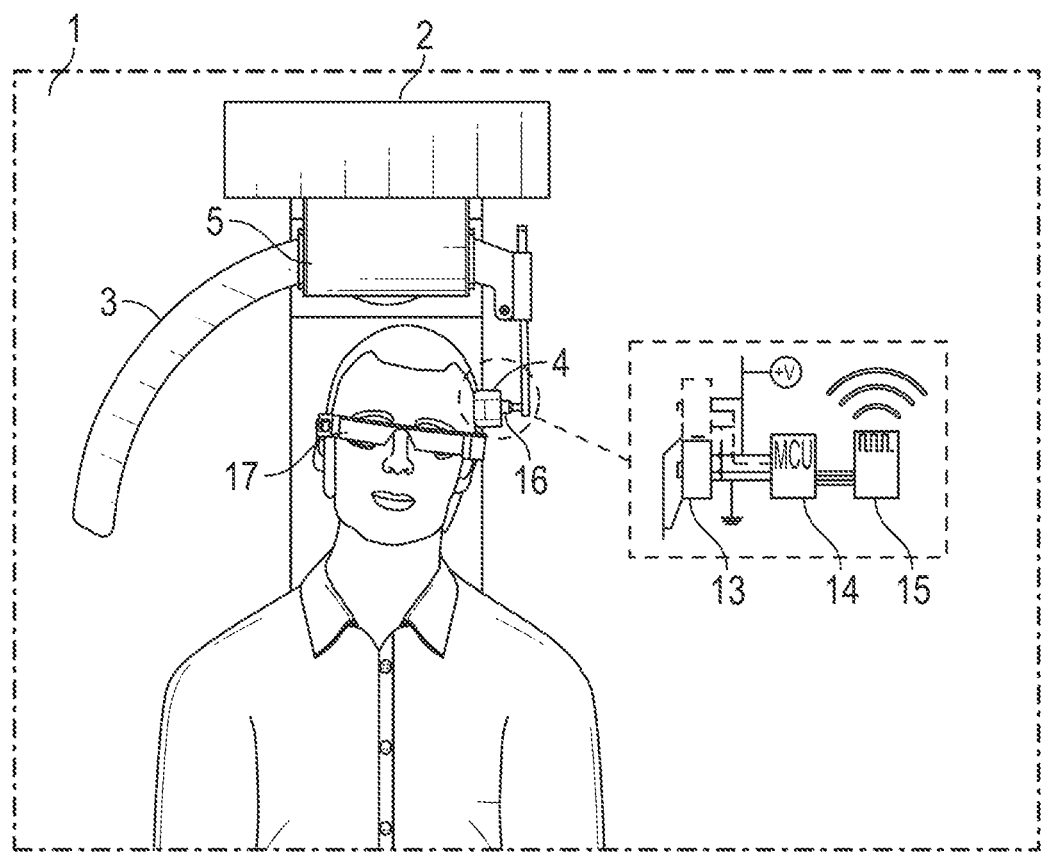
Figure 15:
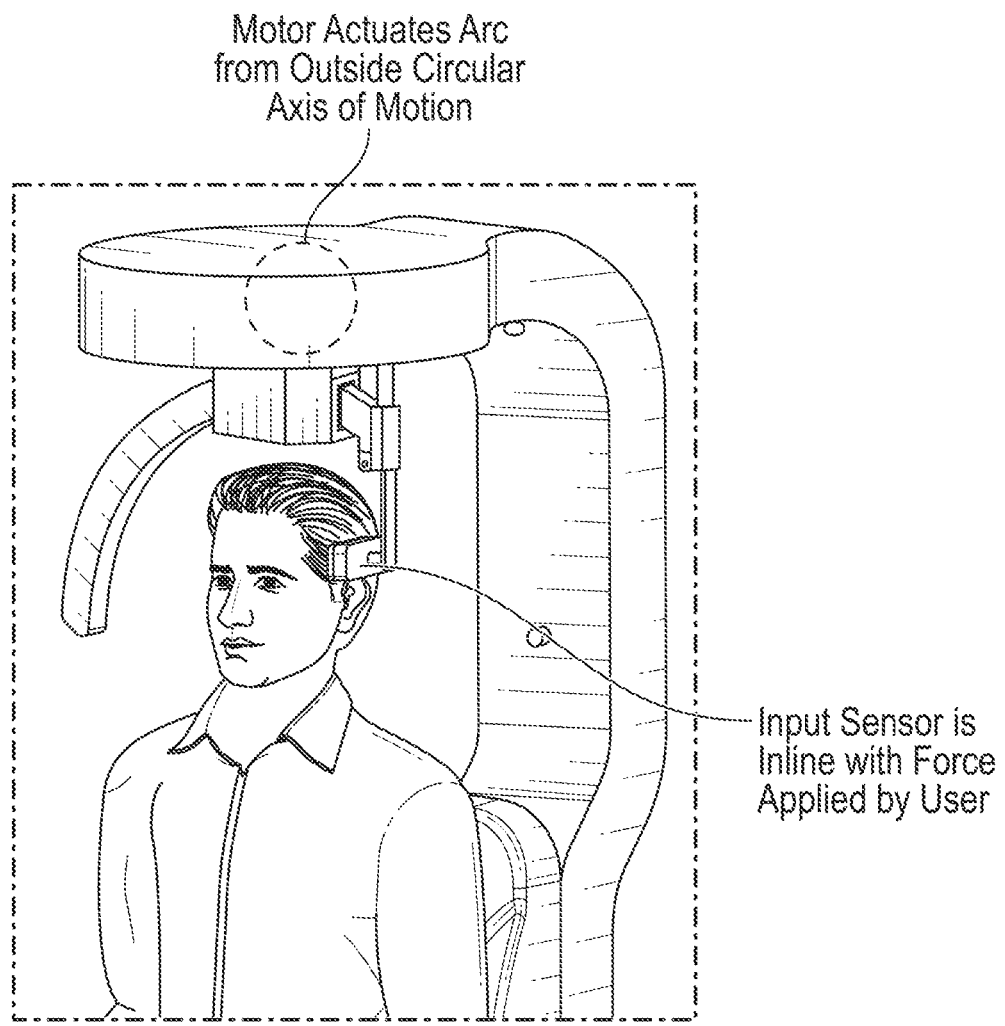
Figure 16:
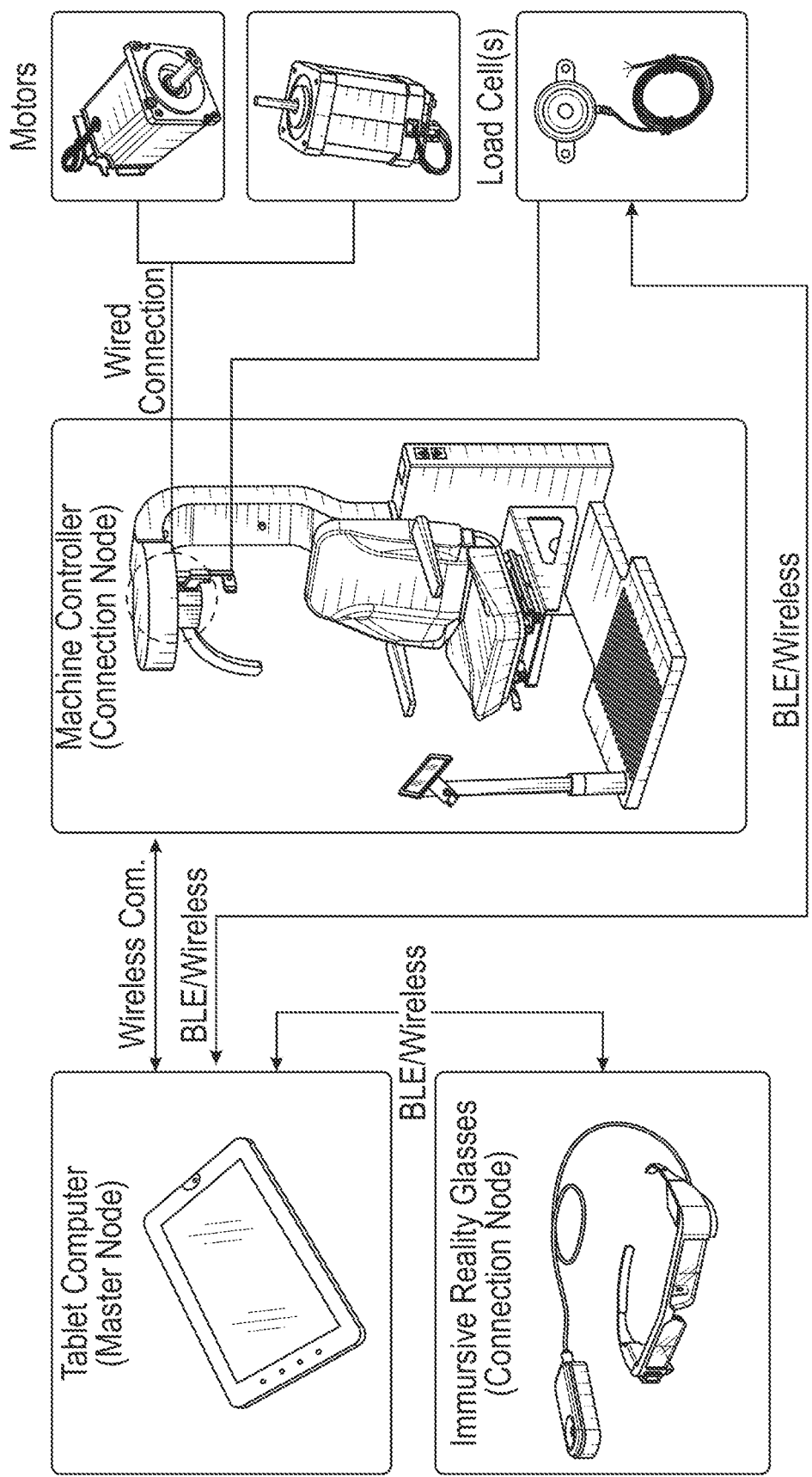
Figure 17:
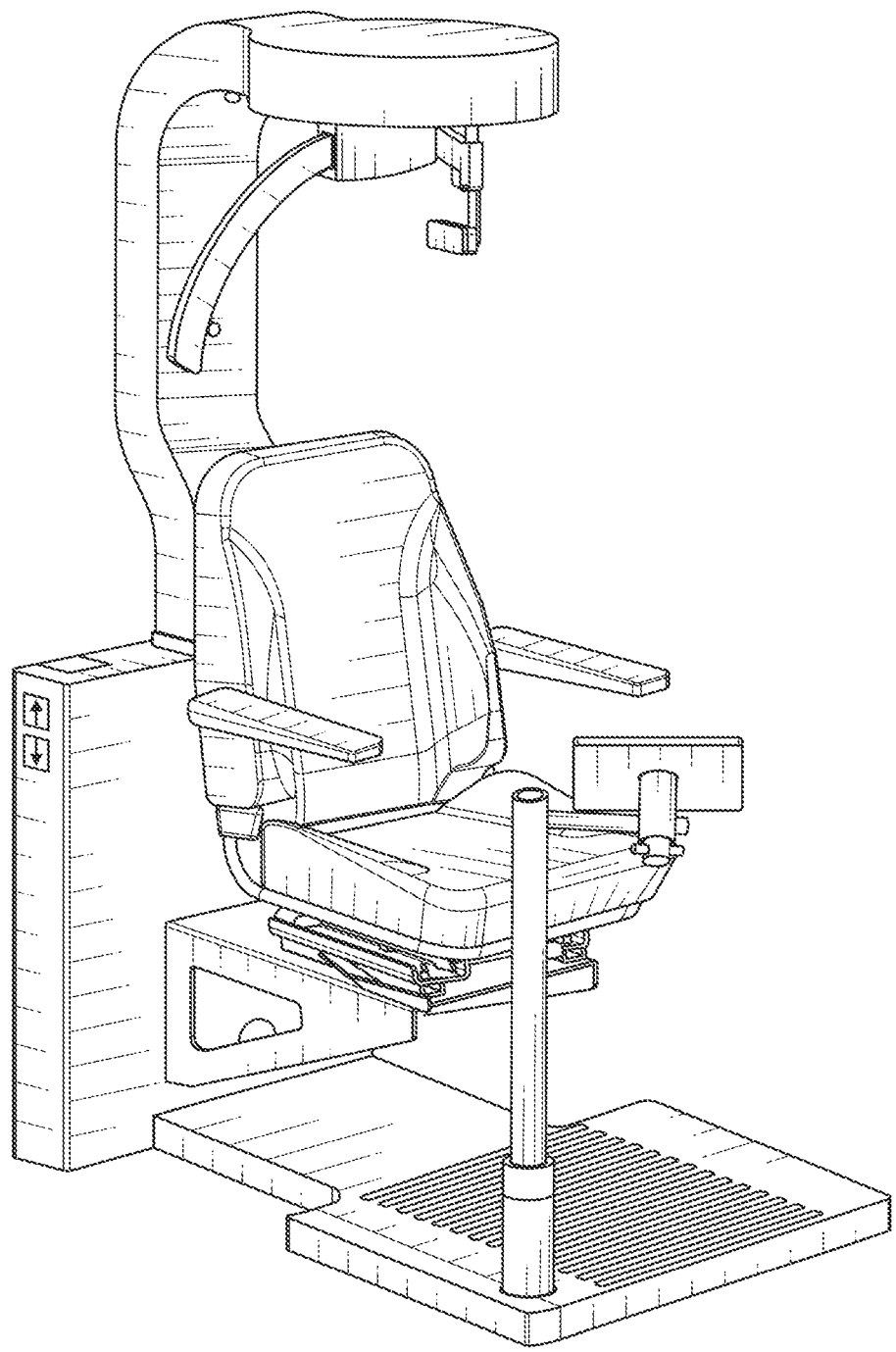
Figure 18A:
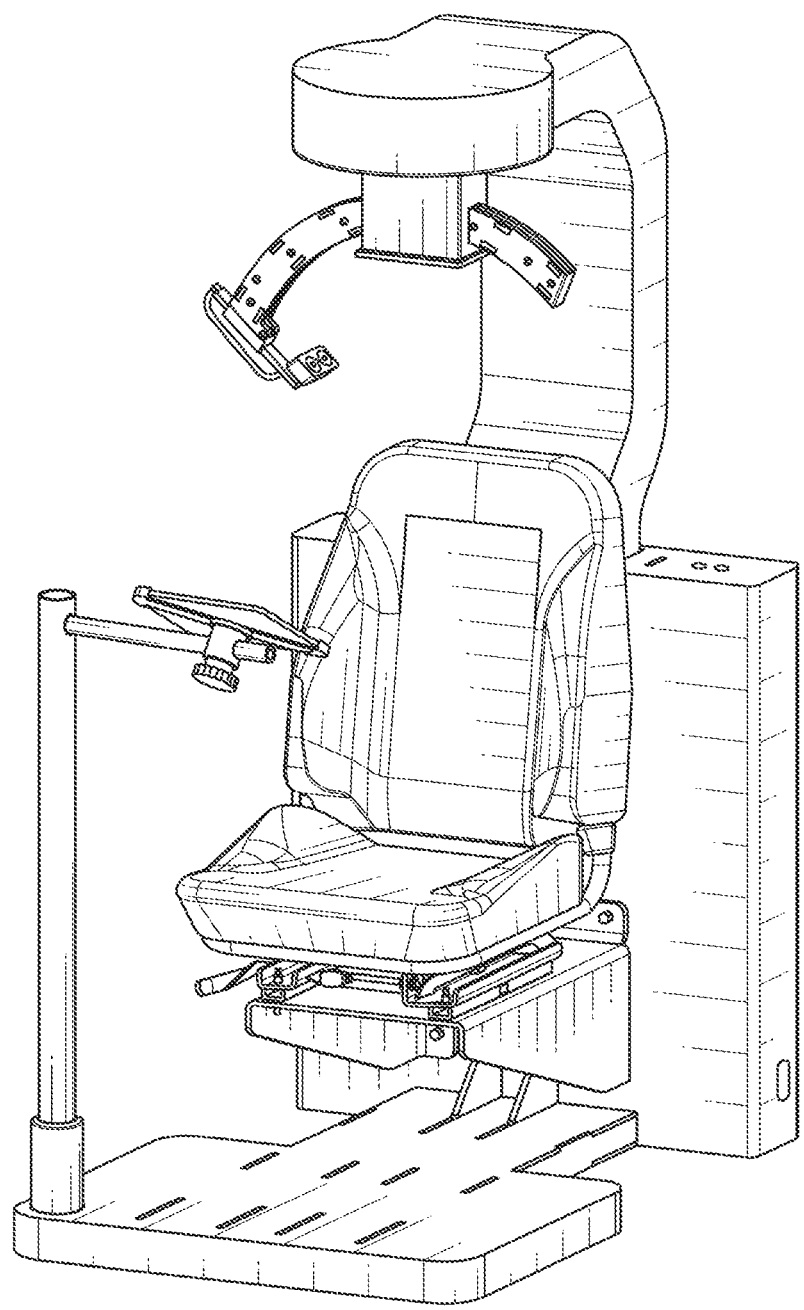
Figure 18B:
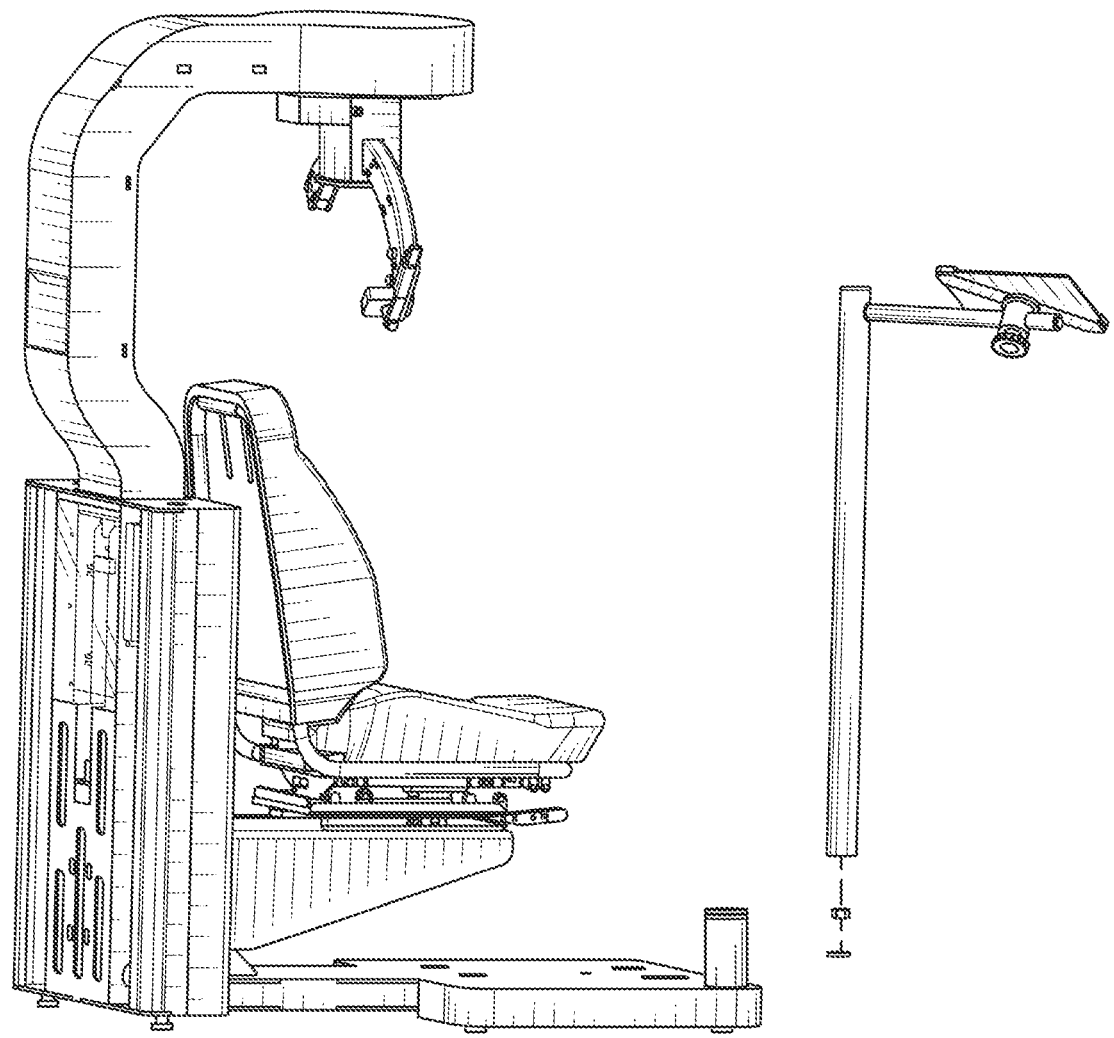
Figure 18C:
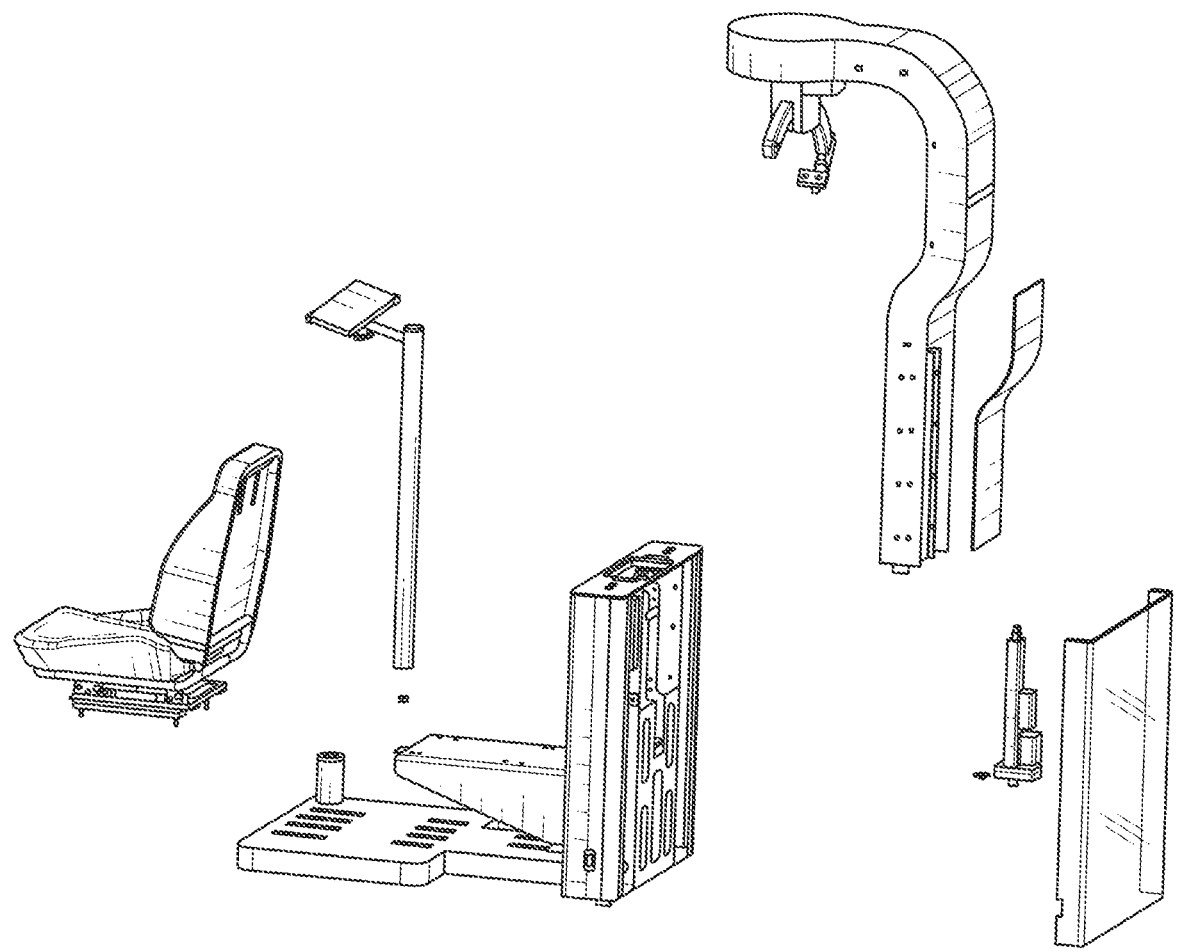
Figure 18D:
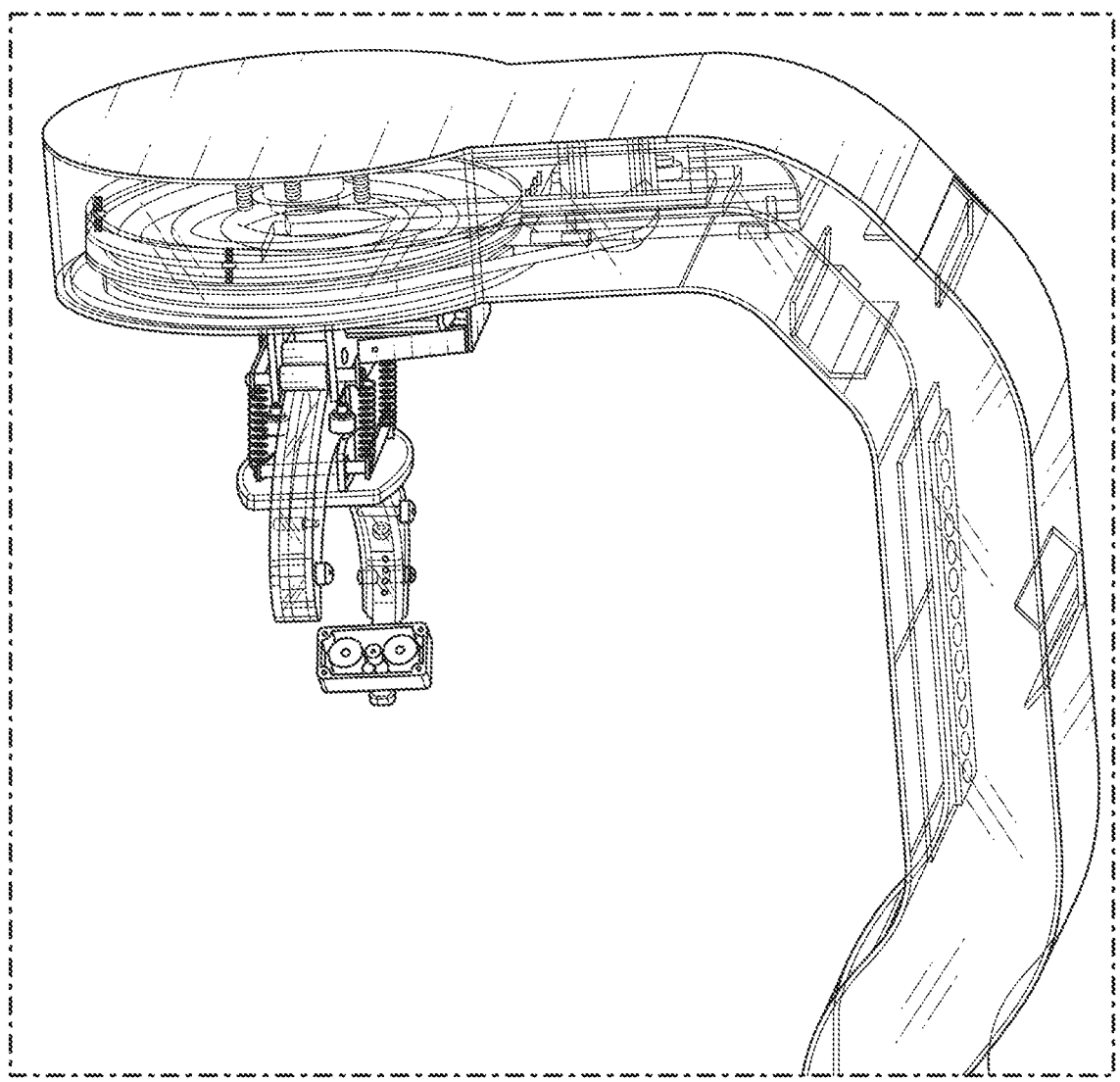
Figure 18E:
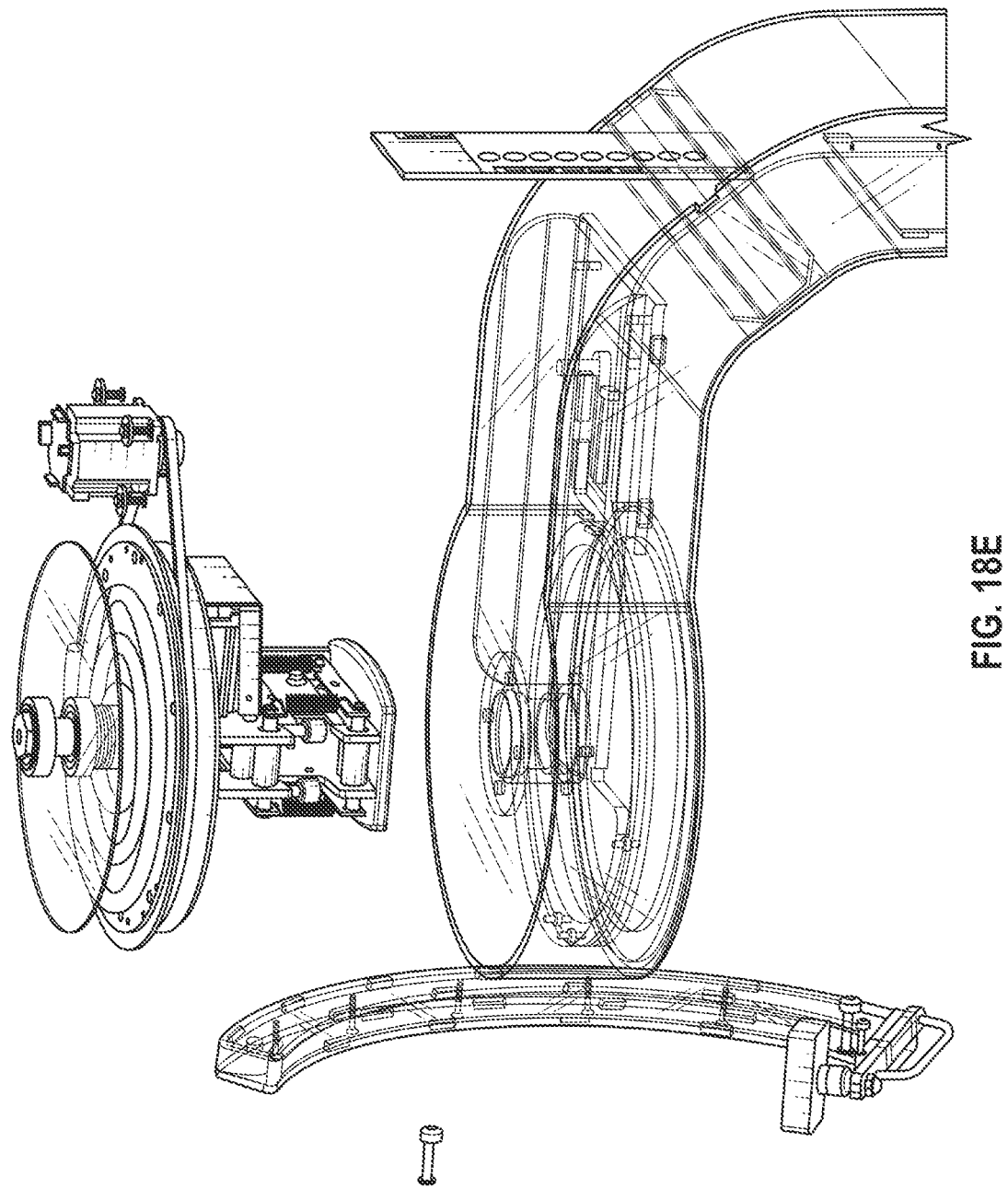
Figure 18F:
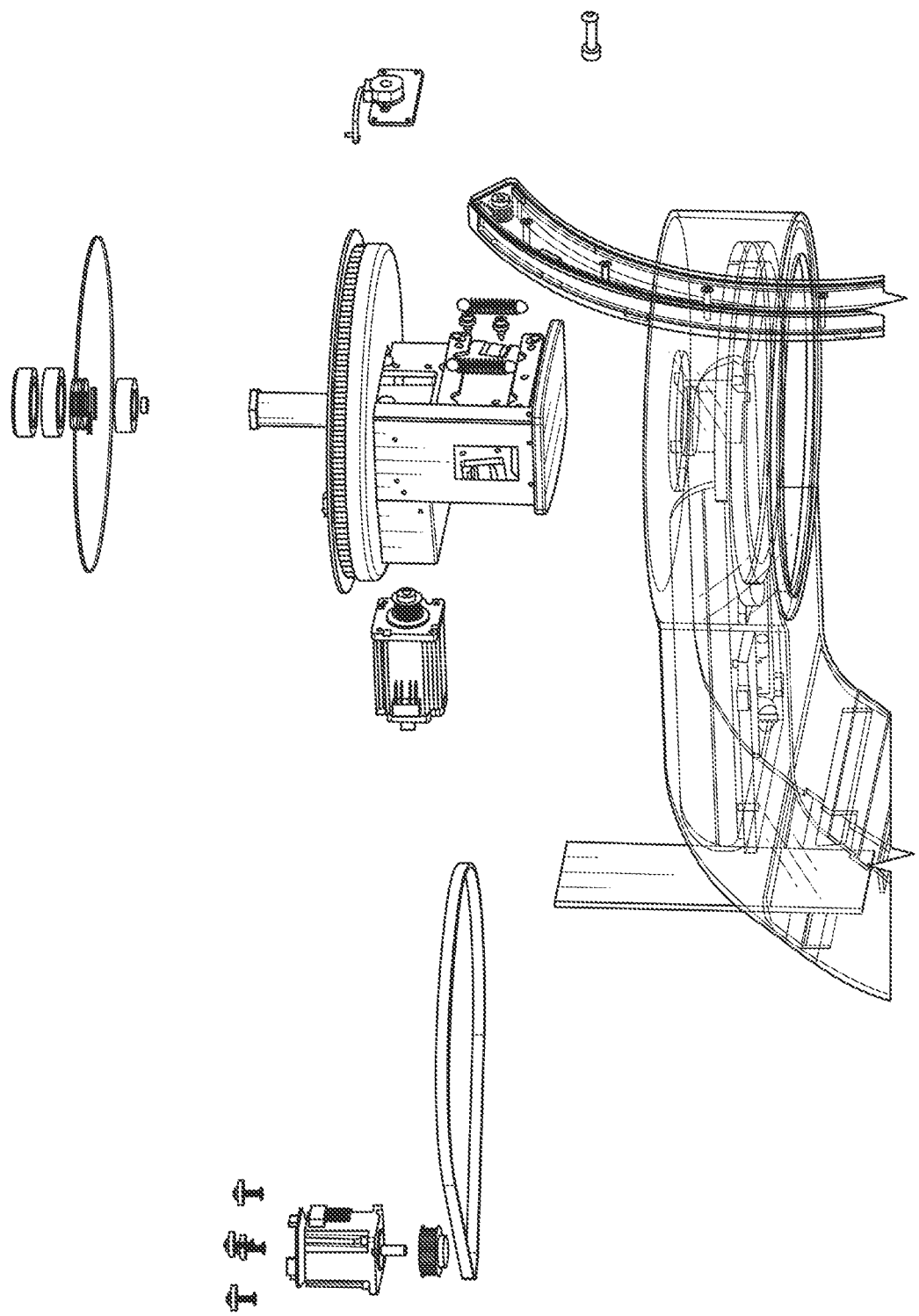
Figure 18G:
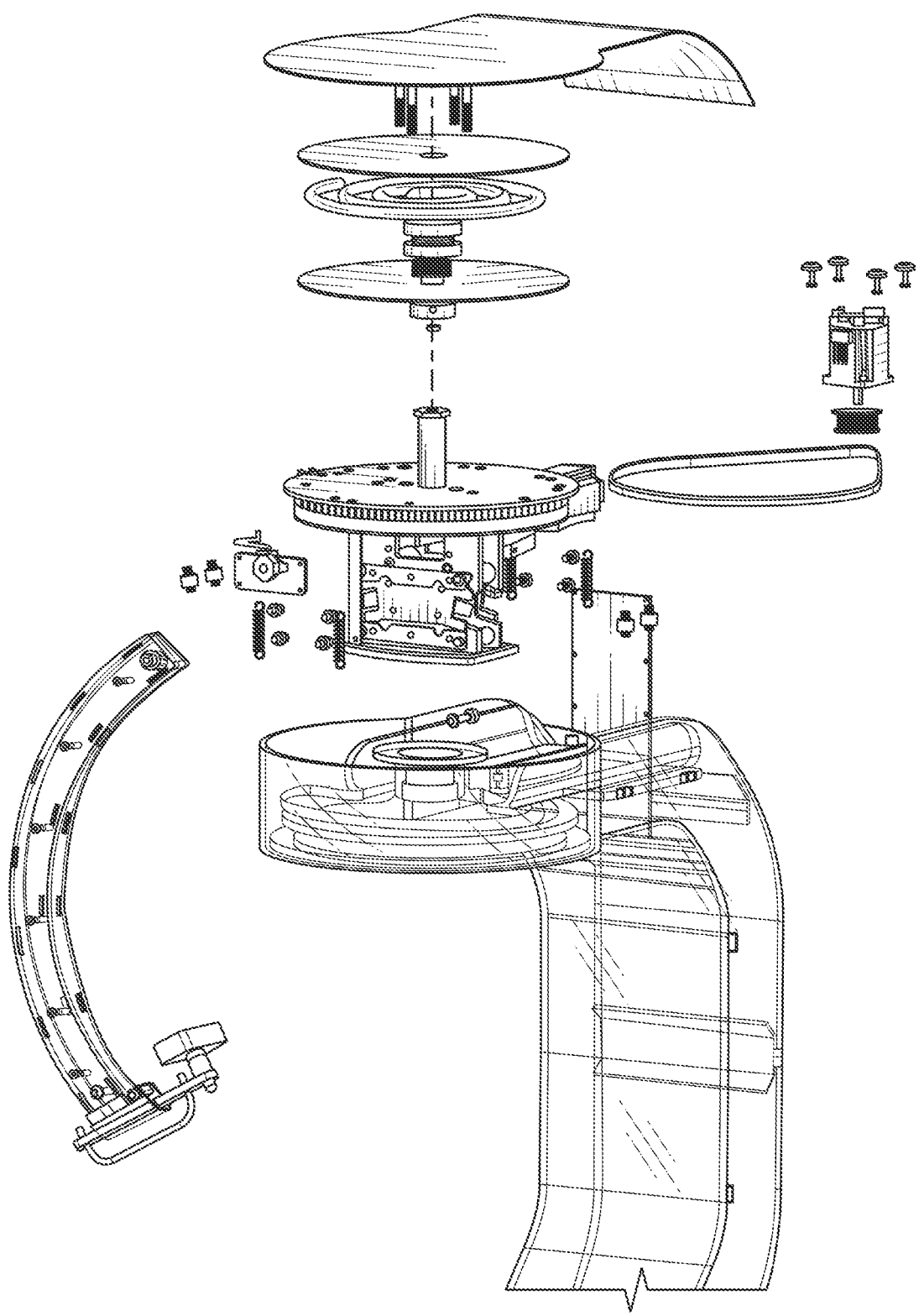
Figure 19:
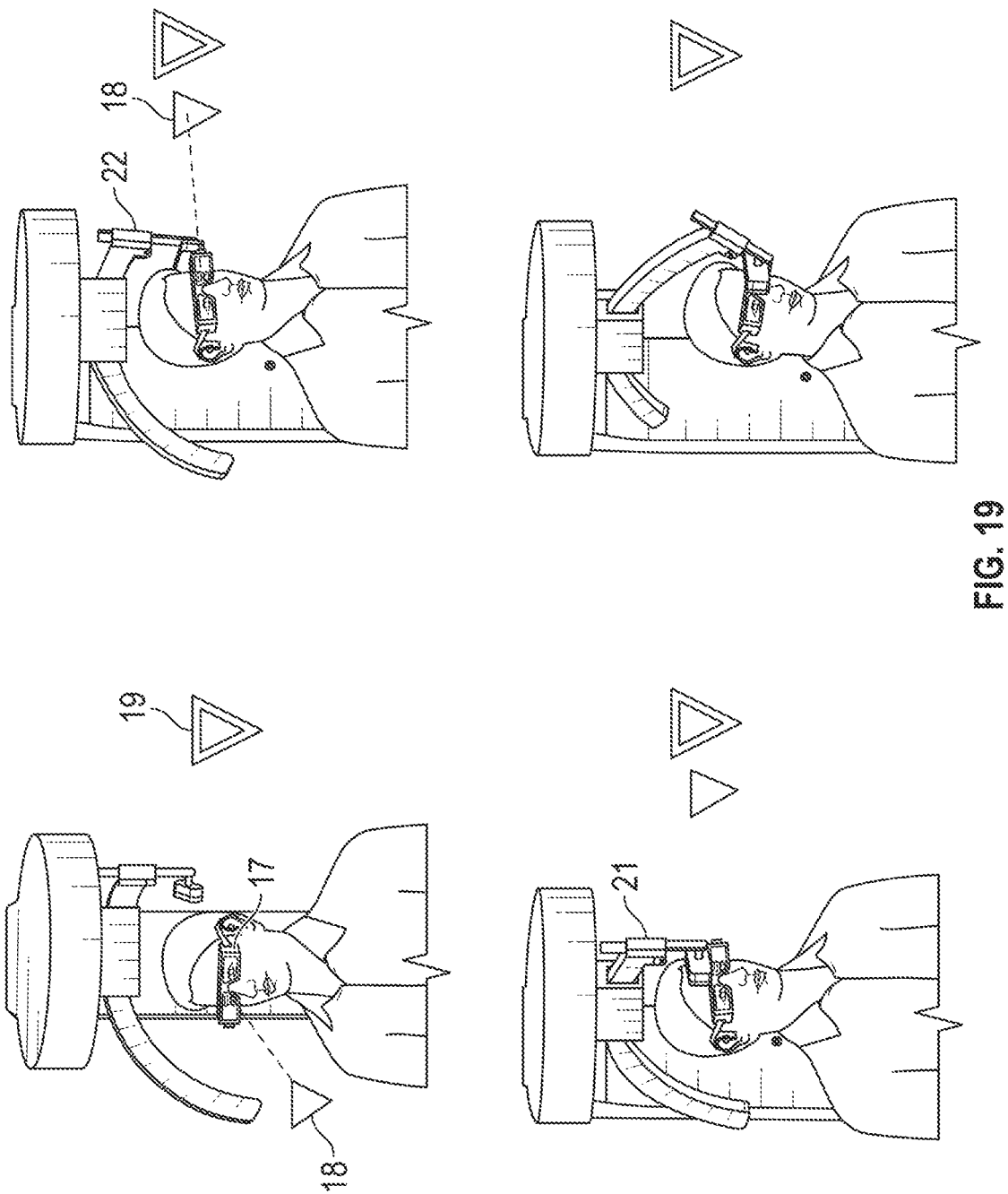
Figure 21:
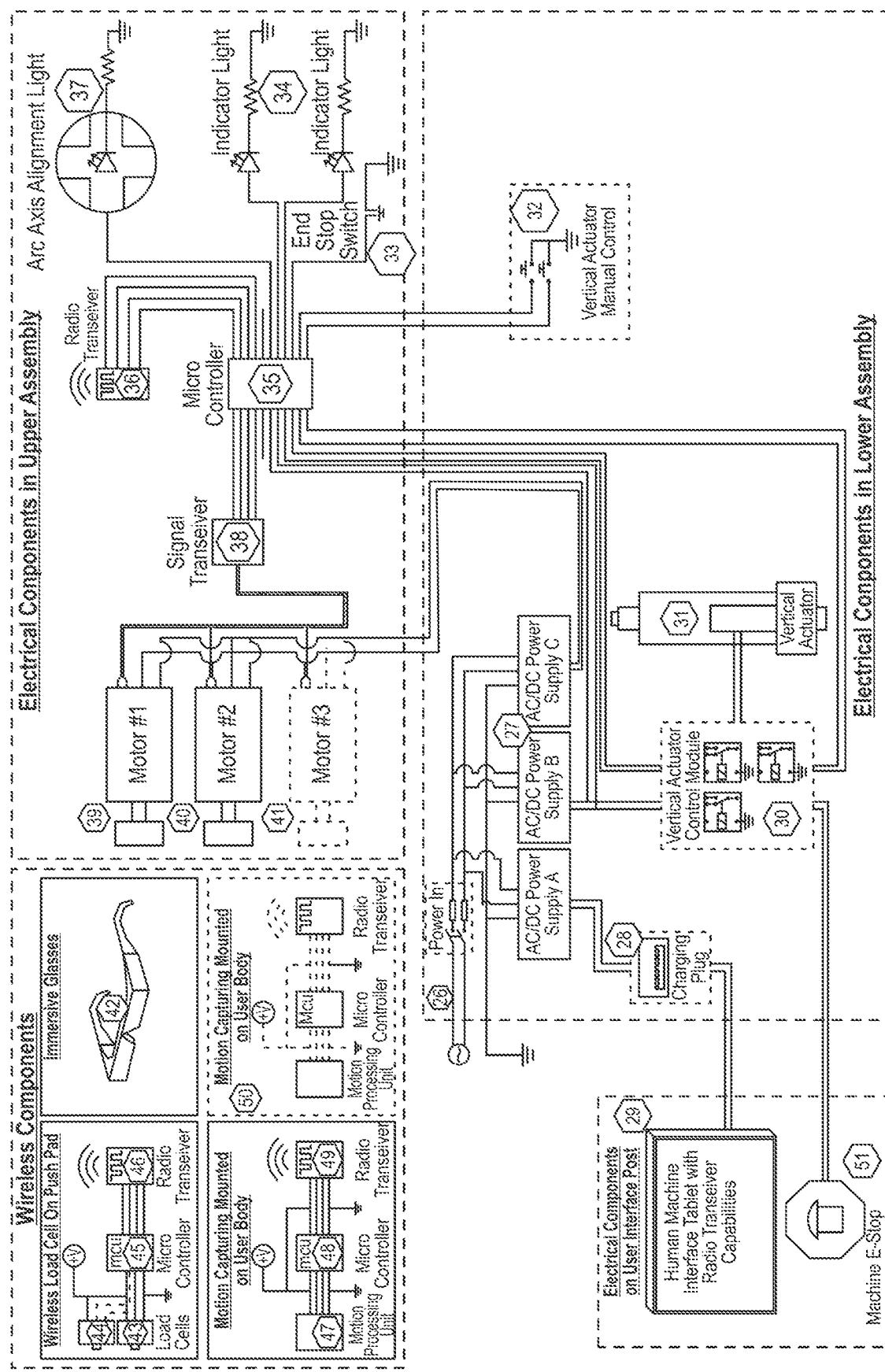
Figure 22:
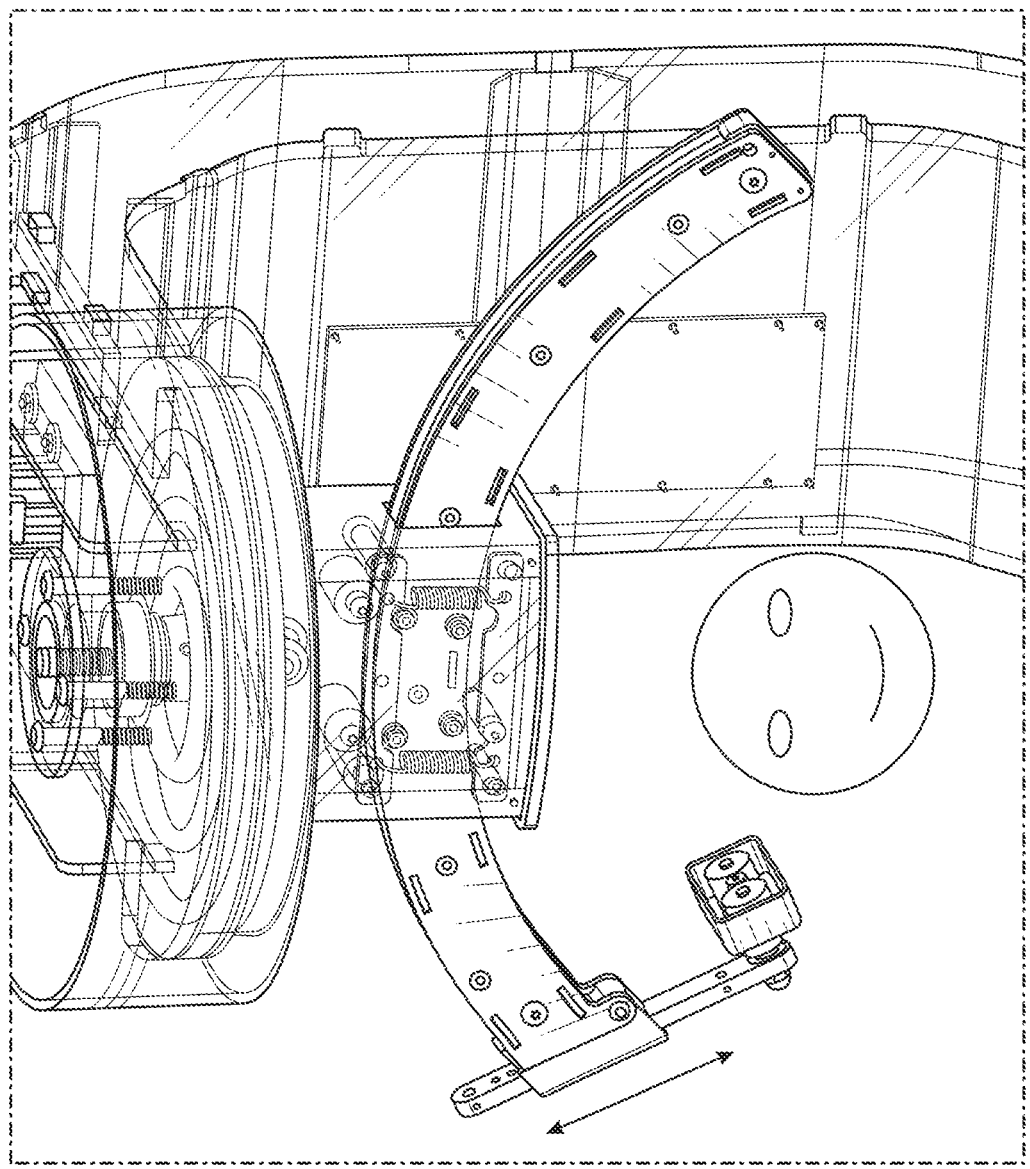
Figure 23:
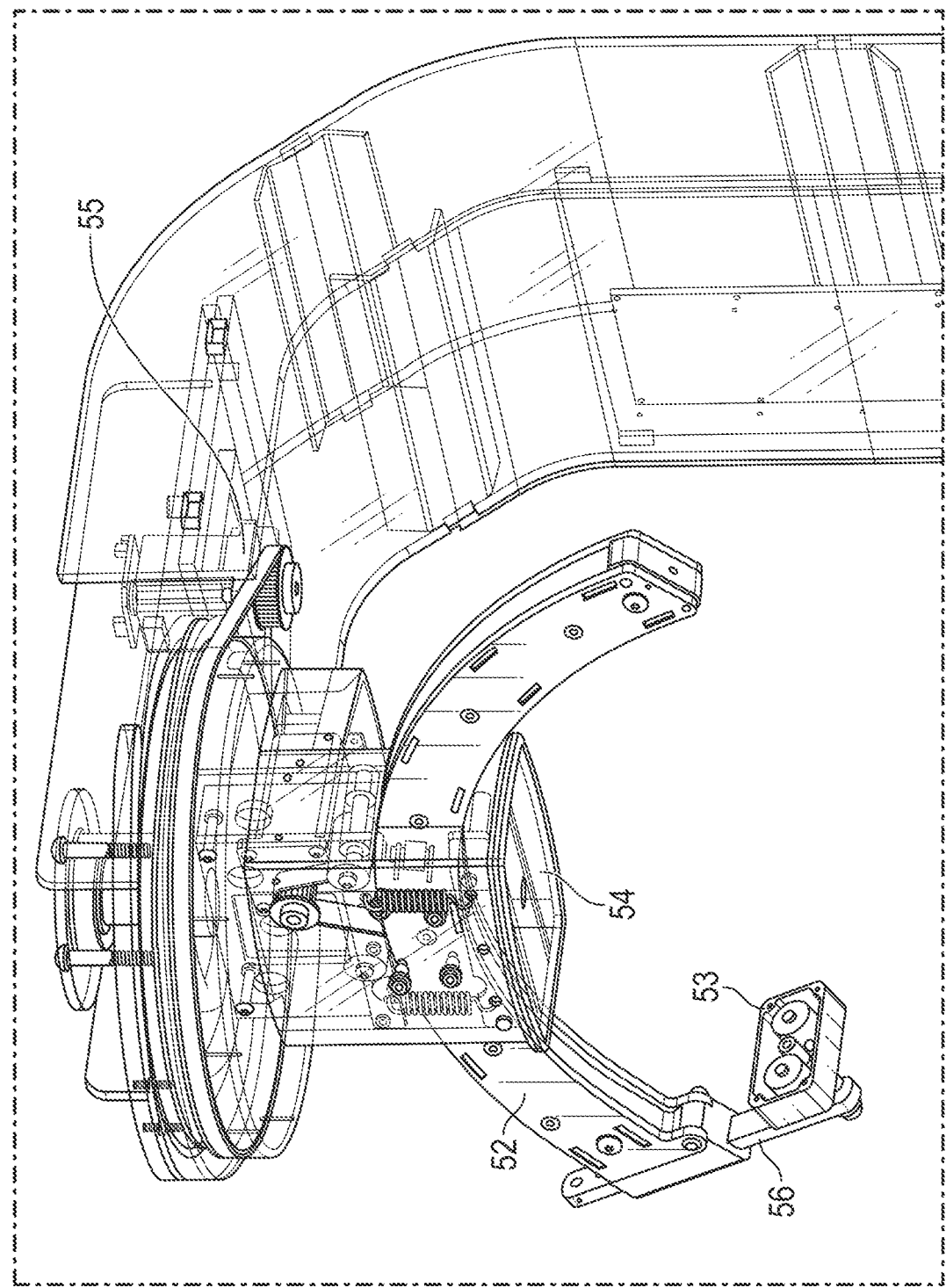
Figure 24:
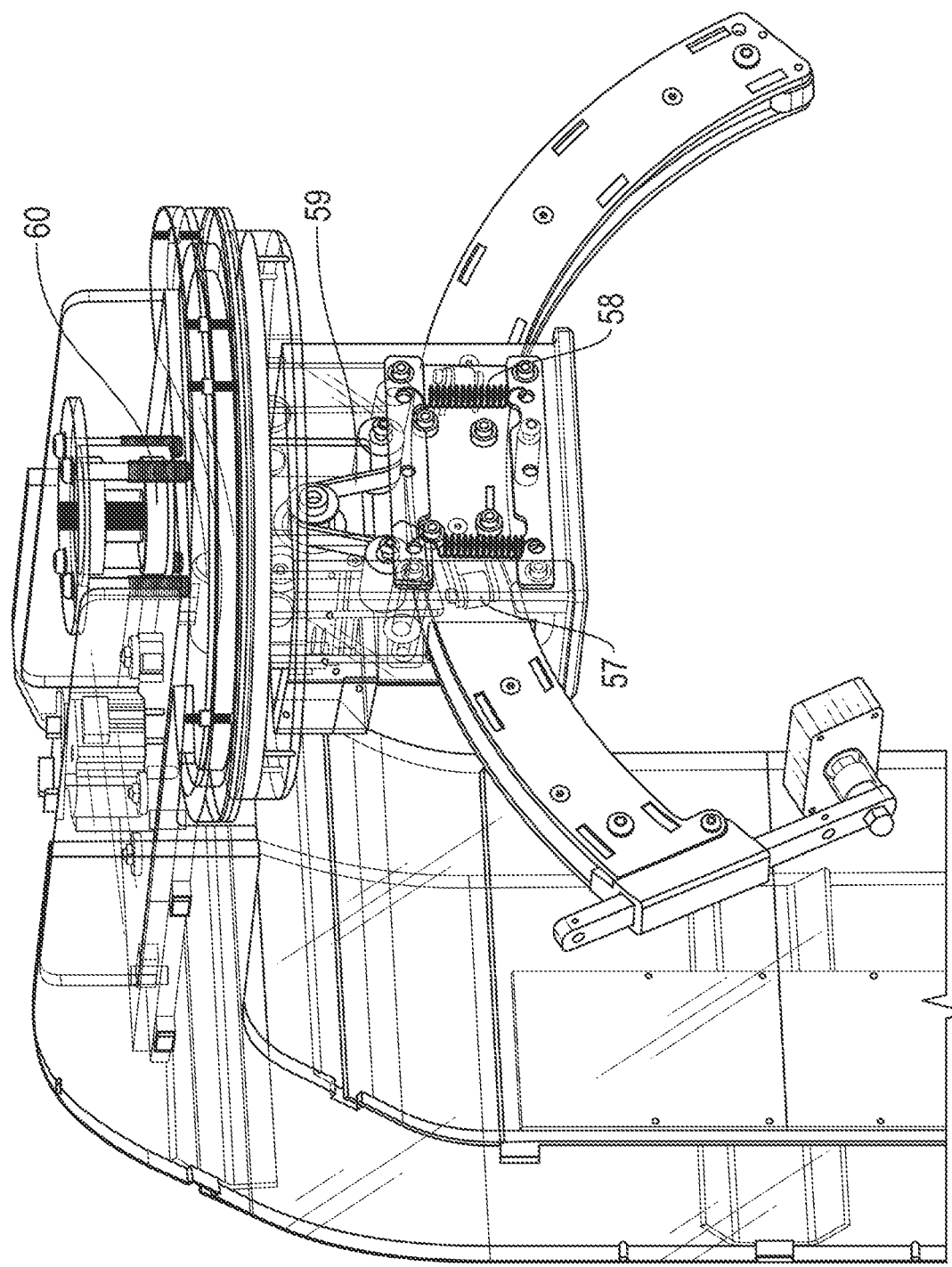
Figure 25:
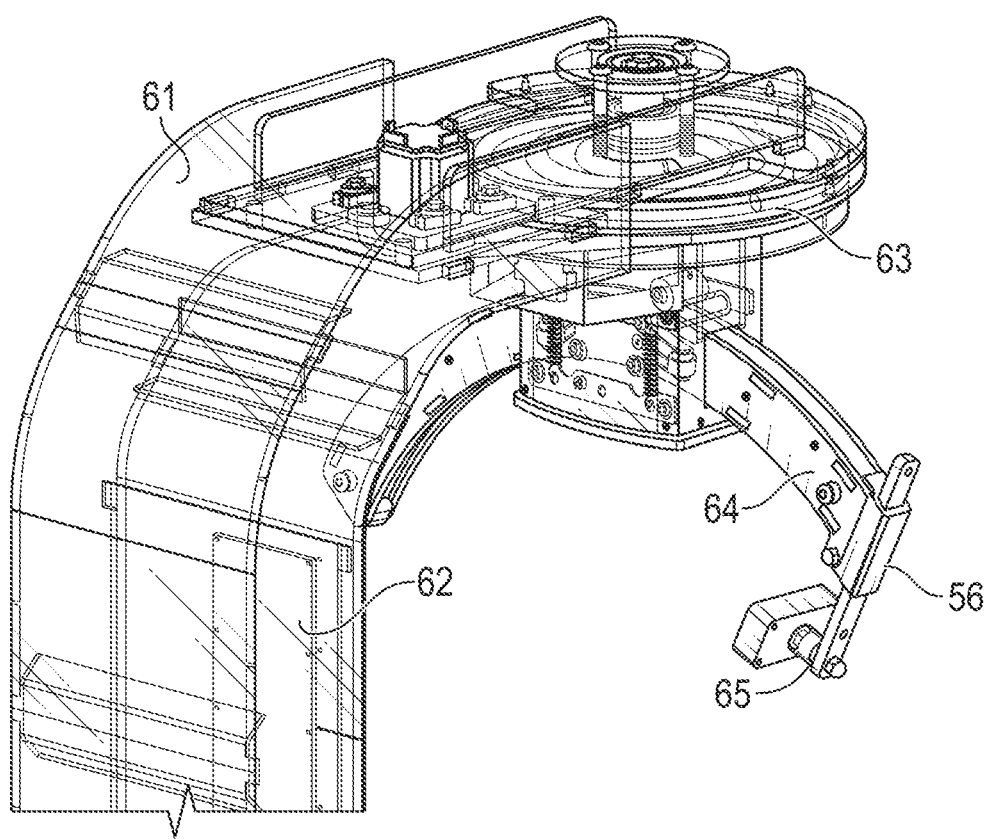
Figure 26:
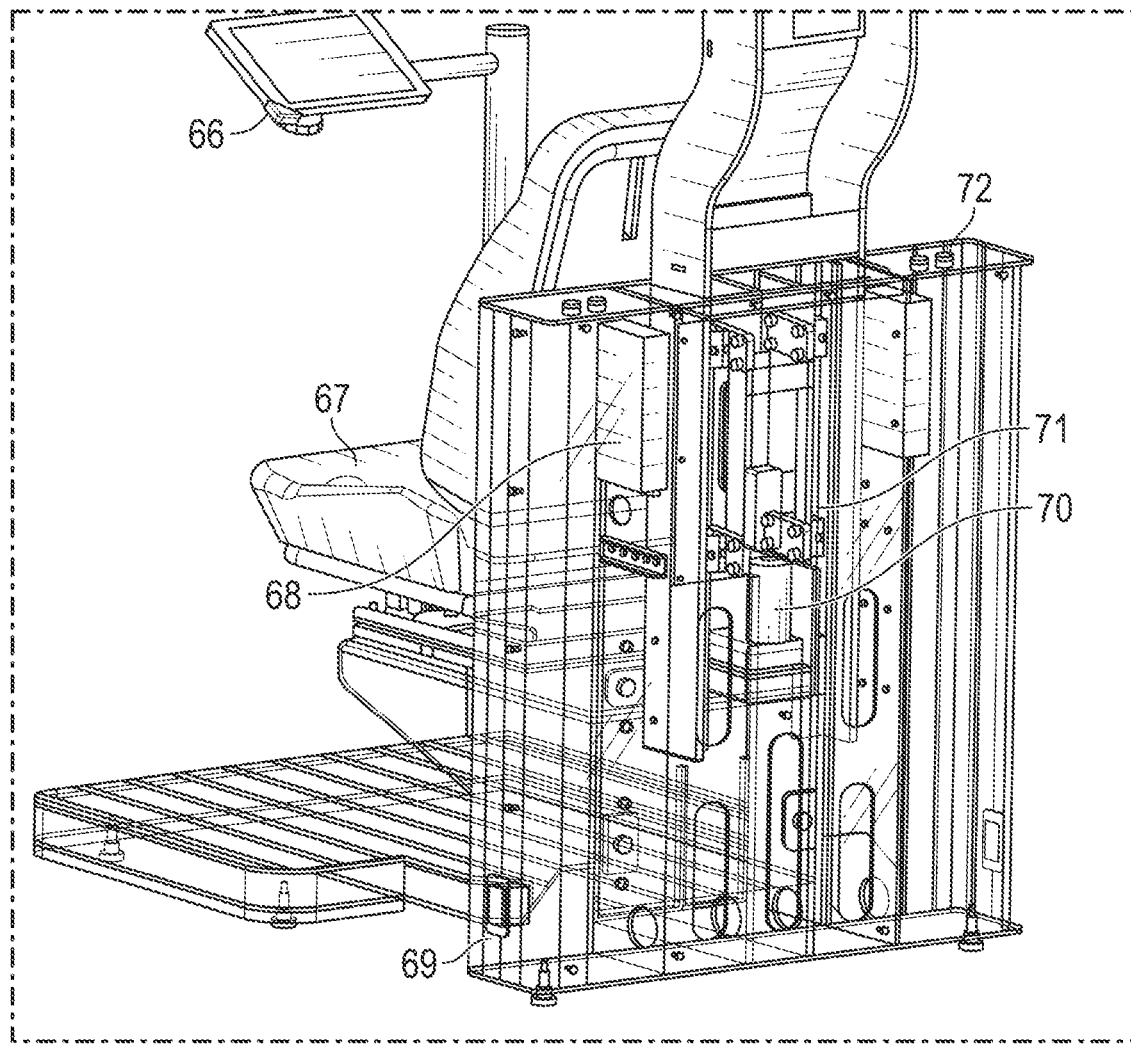
Figure 27:
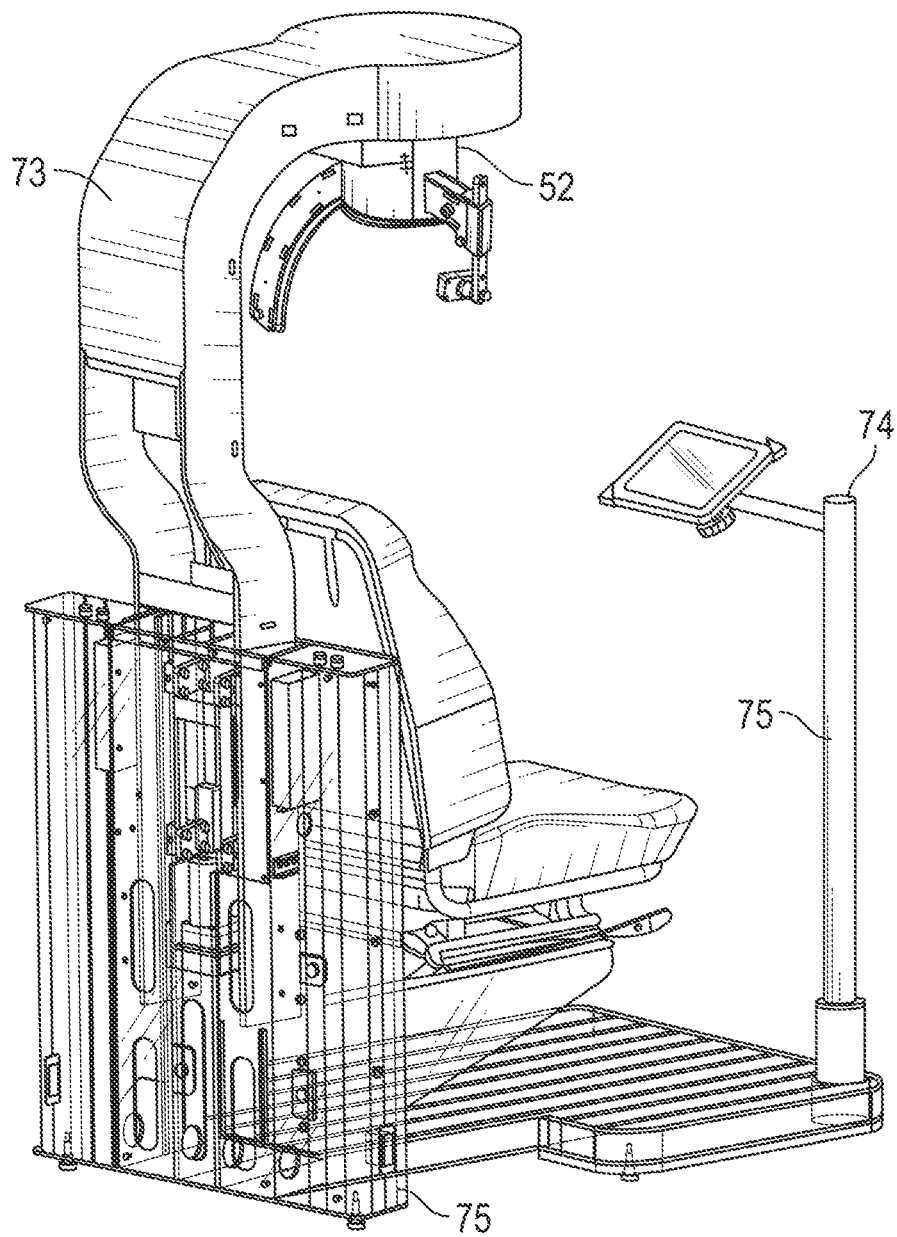
Figure 28:
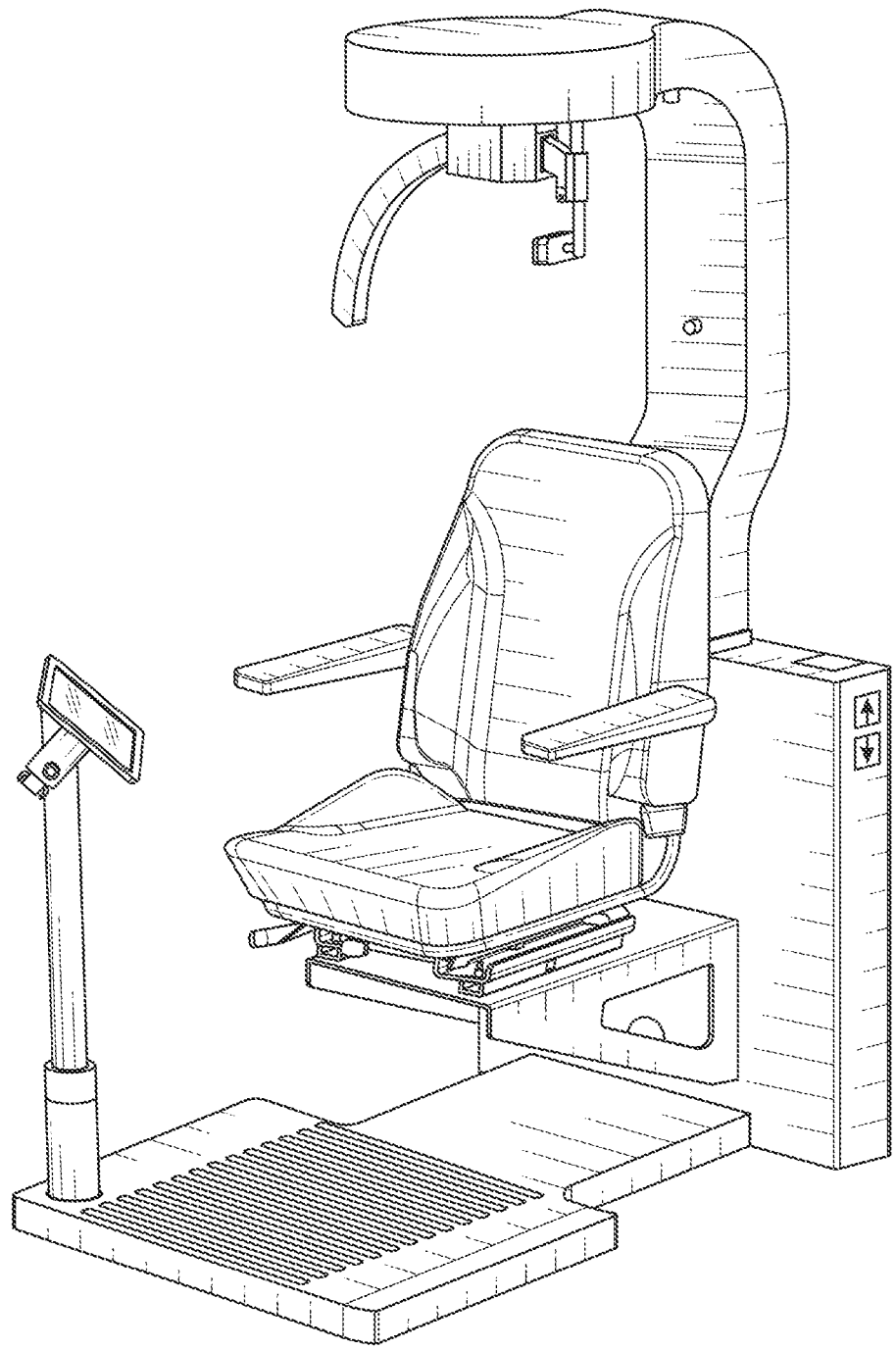
Figure 29:
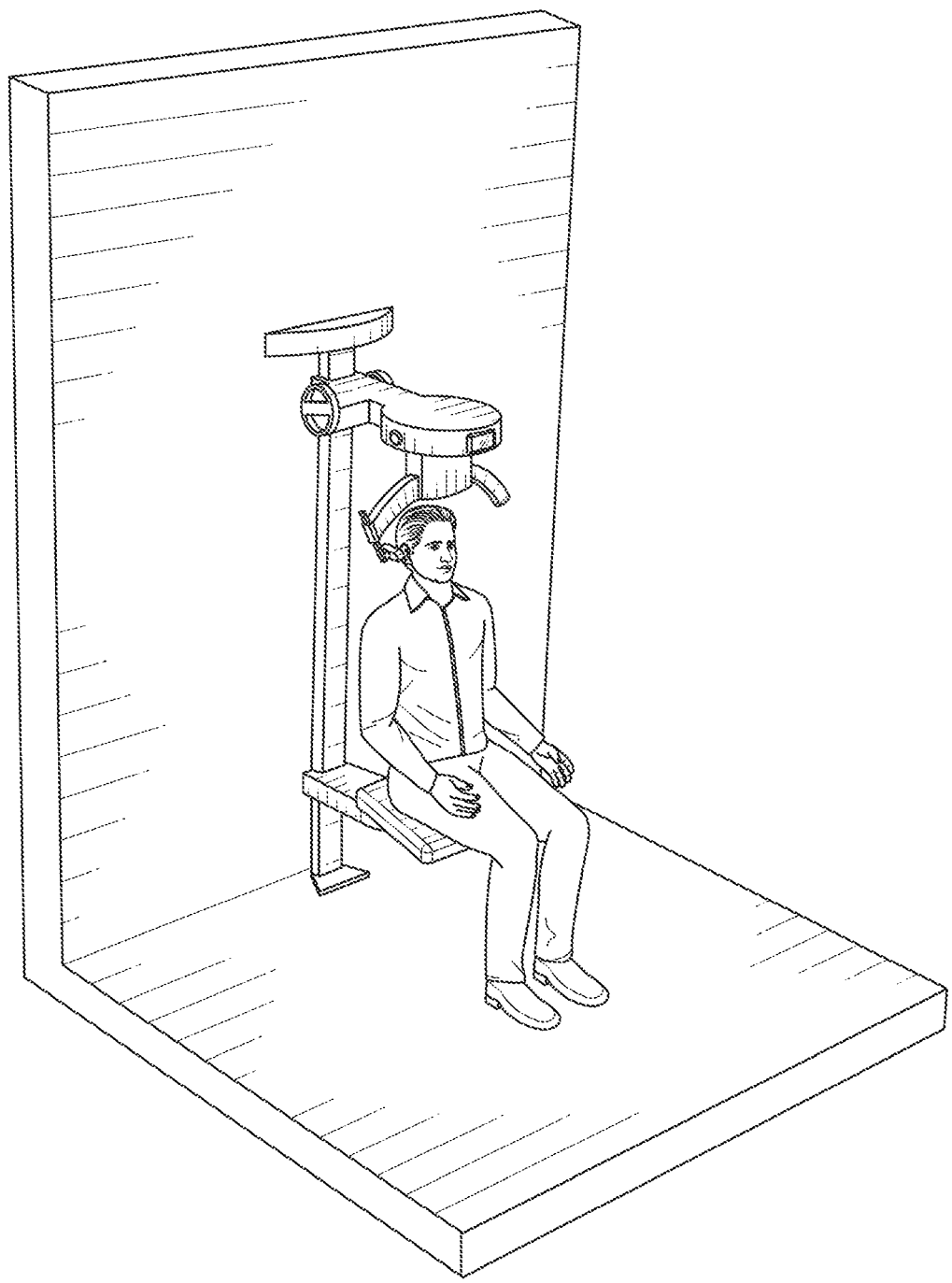
Figure 30:
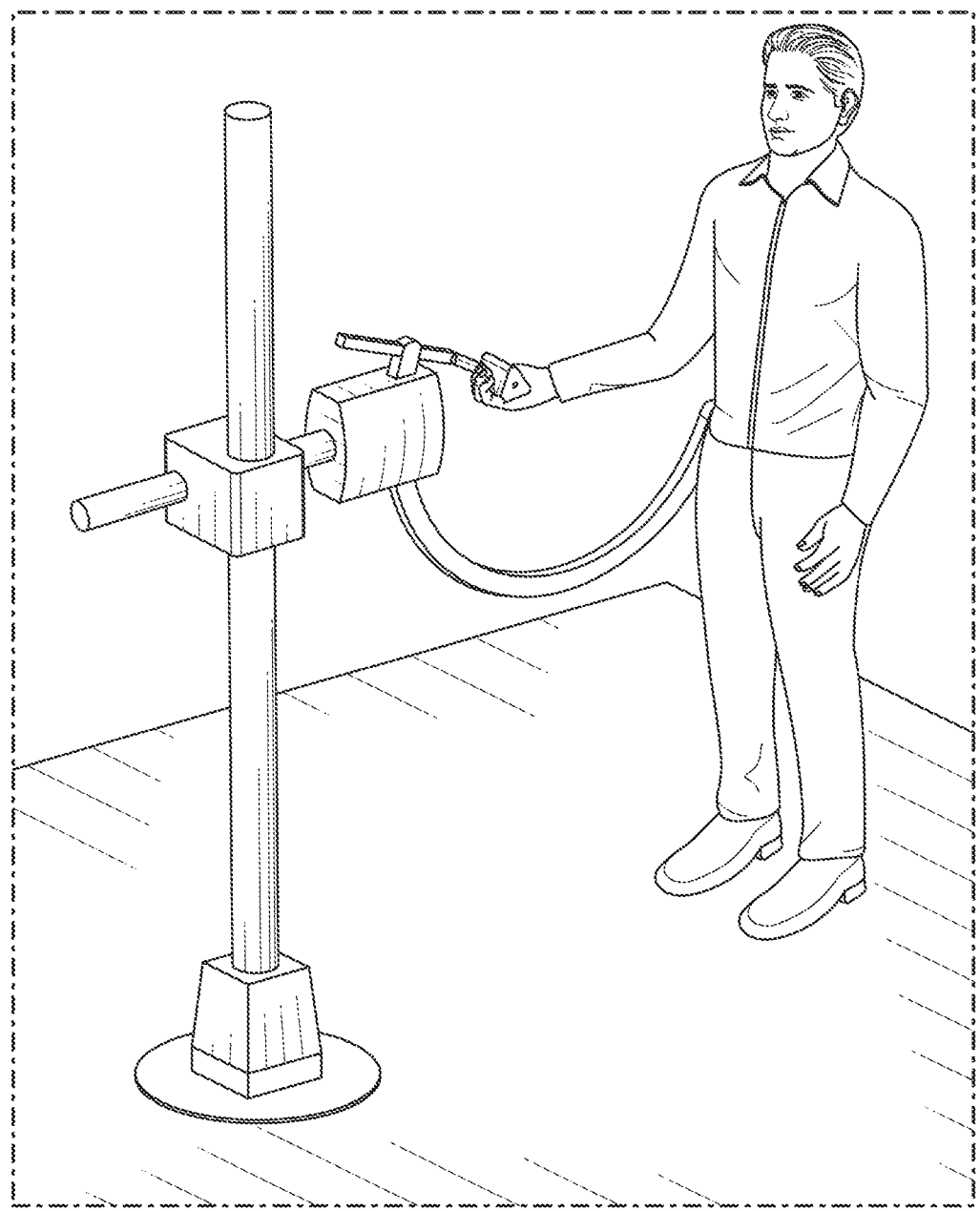
Figure 31:
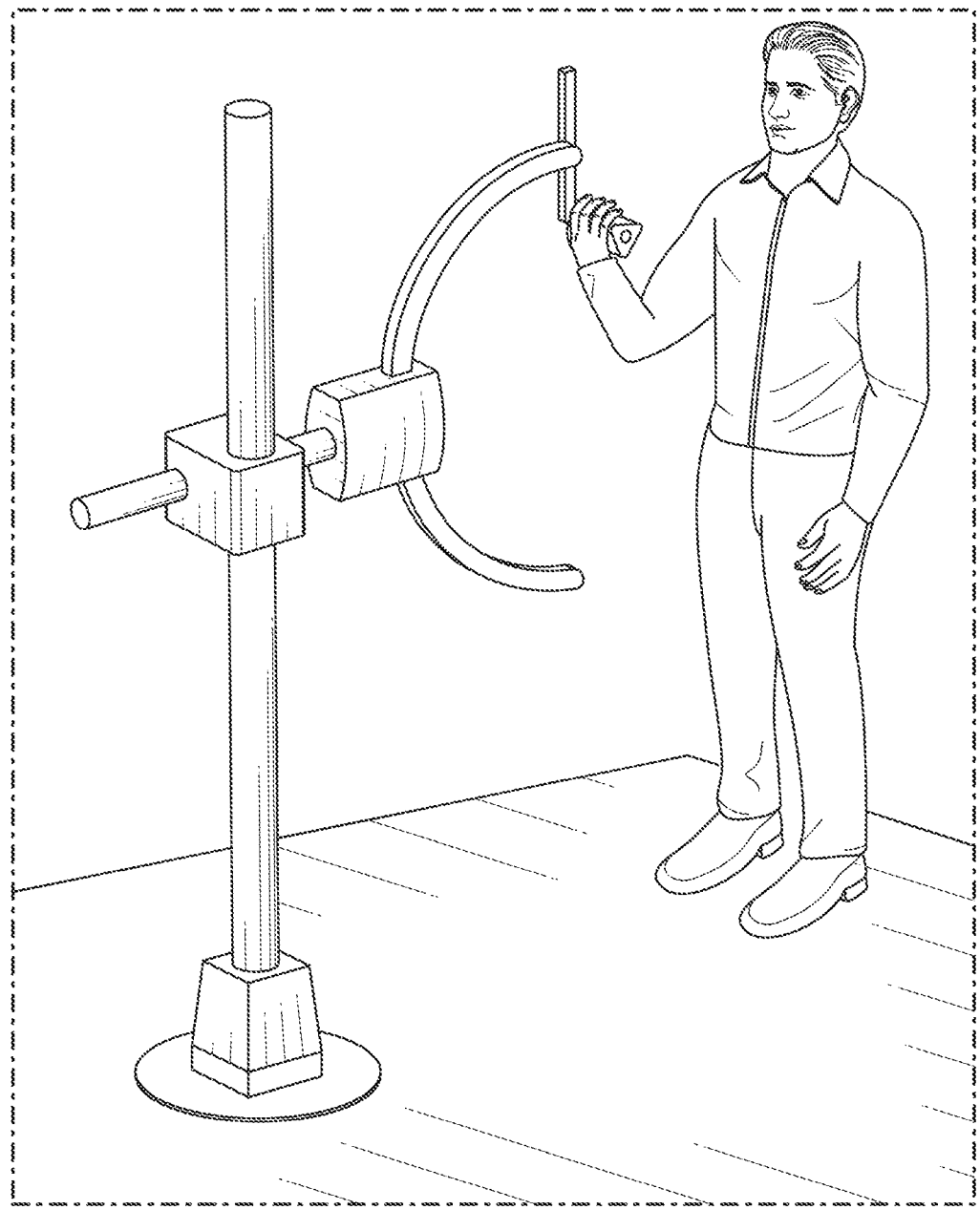
Figure 32:
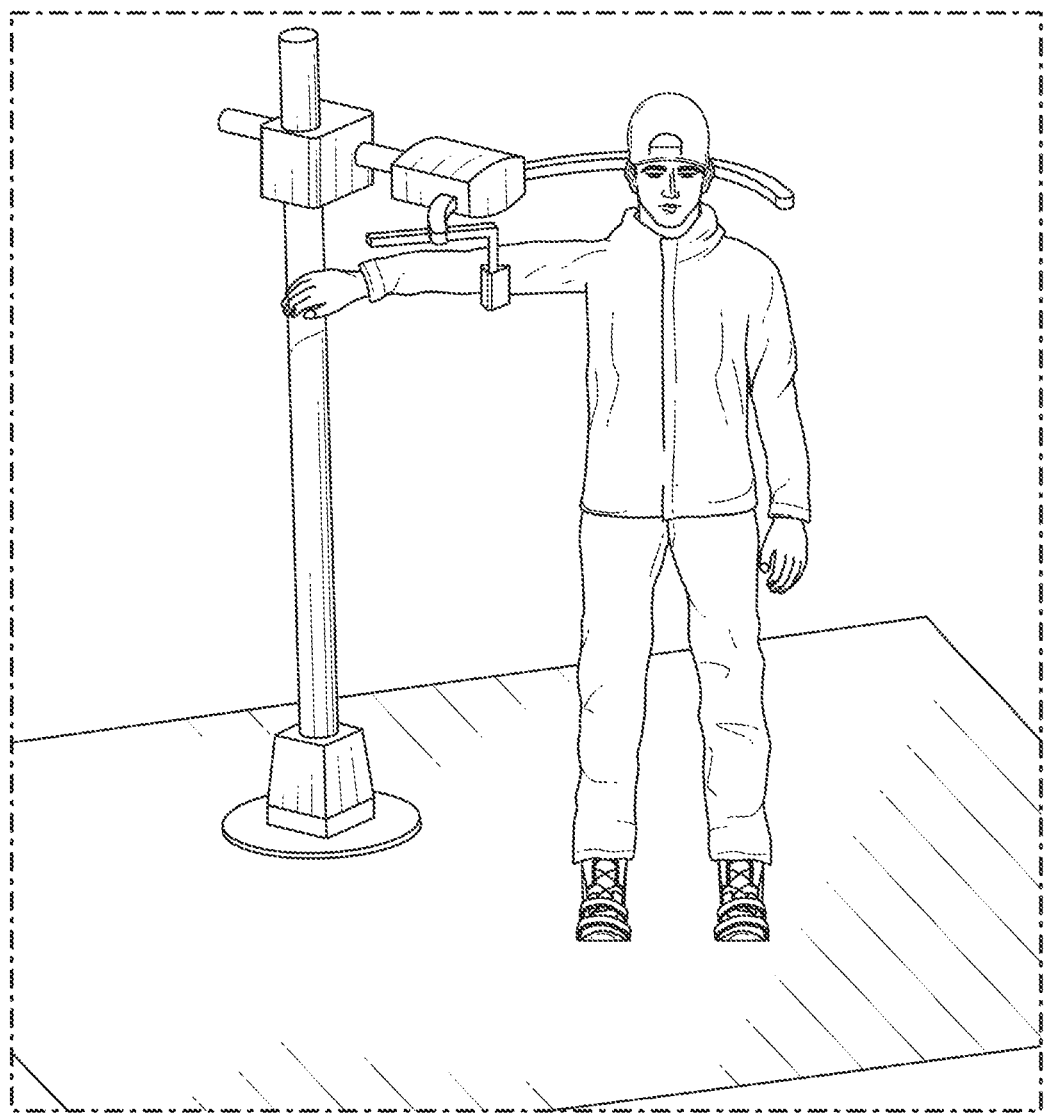
Figure 33:
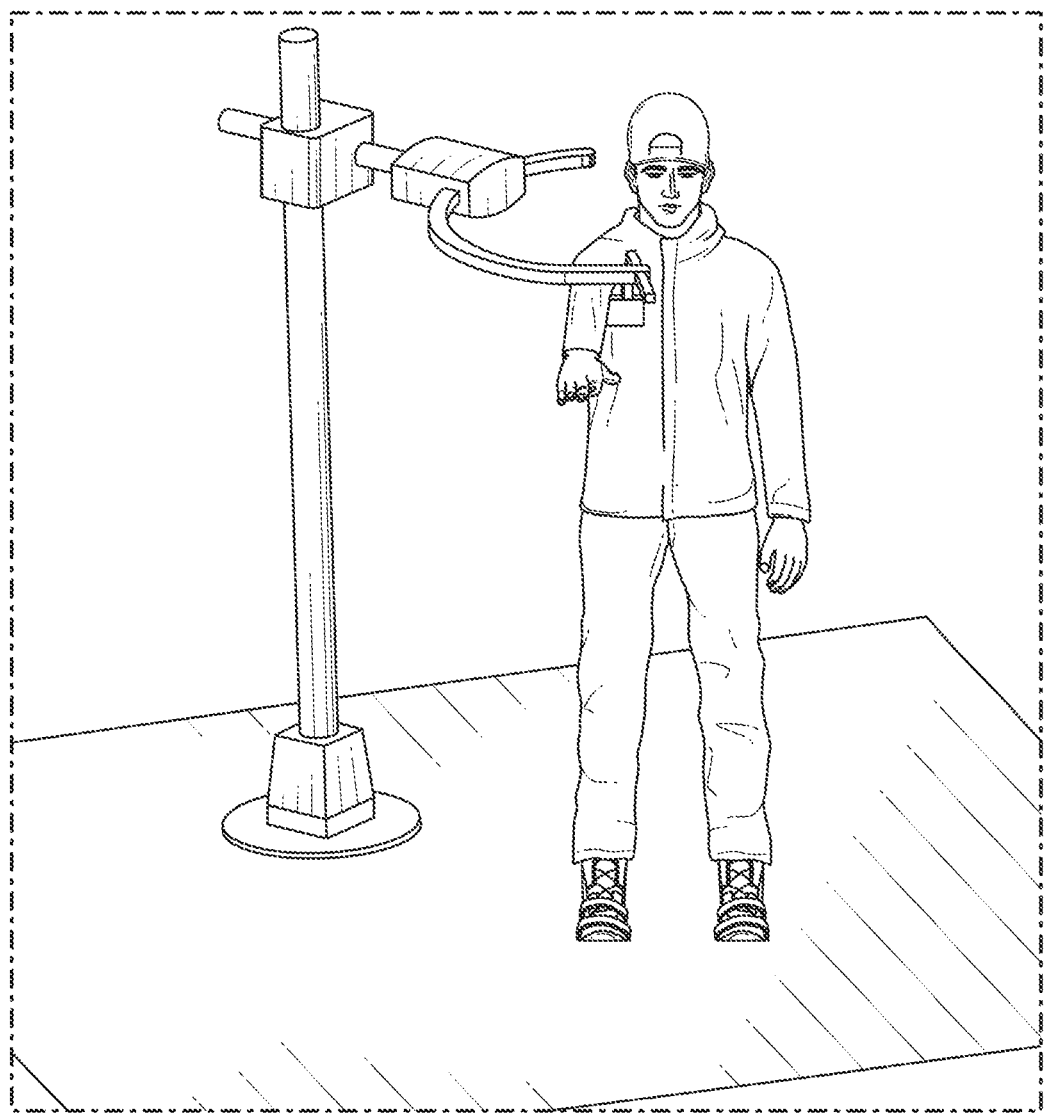
Figure 34:
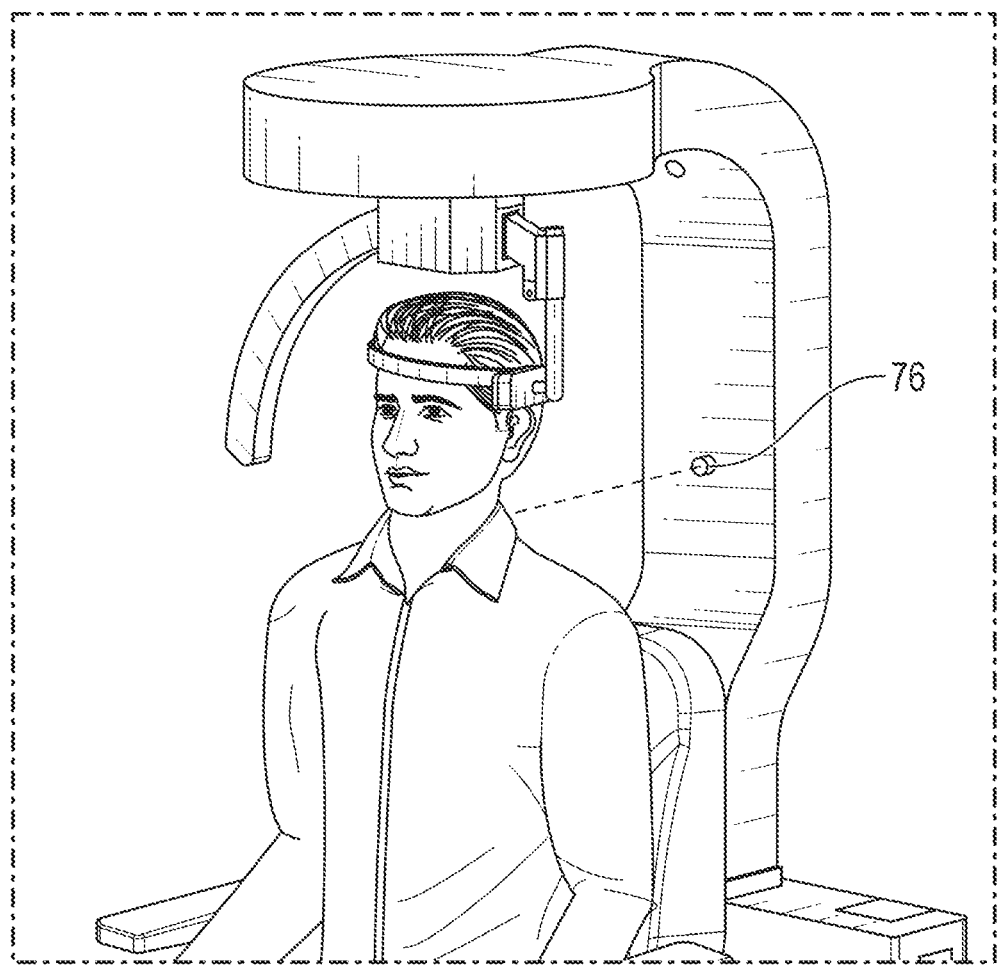

FIG. 9 B shows a perspective view of the subject performing exercise by applying force to the receiving surface;

FIG. 10 shows a perspective view of the exercising subject of FIG. 9 performing exercise of different muscles using the device embodiment of FIG. 5 with the curved guide arm rotated to a different position;

FIG. 11A shows simulated Range of Motion (ROM) readings for a healthy subject;

FIG. 11 B shows simulated Range of Motion (ROM) readings for an injured subject;

FIG. 12A shows an example of a graphical user interface which may be provided for selecting parameters of an exercise or analysis session using a device as described herein;

FIG. 12B shows an example of a graphical user interface displaying subject performance data collected during use;

FIG. 13 shows an example of a graphical user interface displayed to the subject during use, guiding the subject's interaction with the device and providing real-time feedback to the subject;

FIG. 14 shows another embodiment of a device as described herein, with a user interacting with the receiving surface of the device, the receiving surface having an input sensor combined therewith and employing a ball joint linkage to maintain the user force substantially perpendicular to the input sensor along the actuation path of the device during use. The depicted user is wearing augmented reality glasses, which direct or assist the user in performing exercise;

FIG. 15 shows another embodiment of a device as described herein, in which a user is interacting with the receiving surface of the device, and the device provides a rotational actuator-type mechanism in which the motor actuates the guide arm from outside the circular axis of motion; and in which the input sensor is integrated directly inline with the force applied by the user;

FIG. 16 shows a connection diagram for an embodiment of a device as described herein including an AR headset;

FIG. 17 shows another embodiment of a device as described herein including a chair for a user and a height-adjustable support frame allowing the curved guide arm to be raised or lowered according to user height;

FIG. 18A depicts a front rightside perspective view of yet another embodiment of a device as described;

FIG. 18B depicts a back left side perspective view of the embodiment of FIG. 18A;

FIG. 18C depicts an exploded view of the embodiment of FIG. 18A;

FIG. 18D depicts a view of a component of FIG. 18A wherein various components are made transparent;

FIG. 18E depicts an exploded view of the component of FIG. 18D;

FIG. 18F depicts yet another exploded view of the component of FIG. 18D;

FIG. 18G depicts yet another exploded view of the component of FIG. 18D;

FIG. 19 shows various steps (steps 1-4) of a user using an embodiment of a device as described herein which is equipped with an AR headset for guidance through a session of neck exercise using an embodiment of a device as described herein;

FIG. 20A shows another embodiment of a device as described herein, and depicts an example of how the receiving surface may be driven to a desired position about the user to allow for the user to perform an exercise or analysis session;

FIG. 20B shows another embodiment of a device as described herein, and depicts an example of how the receiving surface may be driven to a desired position about the user to allow for the user to perform an exercise or analysis session;

FIG. 21 provides an example of an embodiment of an electrical scheme for a device as described herein;

FIG. 22 provides an example of an embodiment of a device as described herein employing a third motor for adjustment of receiving surface positioning with respect to the curved guide arm;

FIG. 23 depicts another example of an embodiment of a device as described herein, in this example used for neck exercise and/or assessment, as described in Example 2;

FIG. 24 depicts a left side perspective view of the embodiment of FIG. 23;

FIG. 25 depicts another perspective view of the embodiment of FIG. 23;

FIG. 26 depicts another perspective view of the bottom of a device of the embodiment of FIG. 23;

FIG. 27 depicts another perspective view of the entire device of the embodiment of FIG. 23;

FIG. 28 provides a perspective view of a device embodiment similar to those show in FIGS. 23-27;

FIG. 29 depicts a device variant which is wall-mounted;

FIG. 30 depicts embodiments of devices as described herein configured for exercise and/or assessment of the elbow or bicep (FIGS. 30-31), or of the shoulder (FIGS. 32-33);

FIG. 31 depicts the embodiment as described herein configured for exercise and/or assessment of the elbow or bicep as shown in FIG. 30;

FIG. 32 depicts the embodiment as described herein configured for exercise and/or assessment of the shoulder as shown in FIG. 30;

FIG. 33 depicts the embodiment as described herein configured for exercise and/or assessment of the shoulder as shown in FIG. 30; and FIG. 34 depicts a device embodiment including a targeting light to assist with alignment corrections.

DETAILED DESCRIPTION

Described herein are devices and methods for analysis and/or exercise of a body region of a subject. It will be appreciated that embodiments and examples are provided for illustrative purposes intended for those skilled in the art and are not meant to be limiting in any way.

In an embodiment, there is provided herein a device (1) for analysis and/or exercise of a neck region of a subject, the device comprising:

a support frame (2);
a curved guide arm (3) supported by the support frame (2);
a receiving surface (4) supported by the curved guide arm (3), the receiving surface (4) for receiving input force from the subject; and
a motor assembly (5) in communication with the curved guide arm (3), the motor assembly (5) controlling movement of the receiving surface (4) with respect to the subject based on input force received from the subject at the receiving surface (4).

Figure 1:
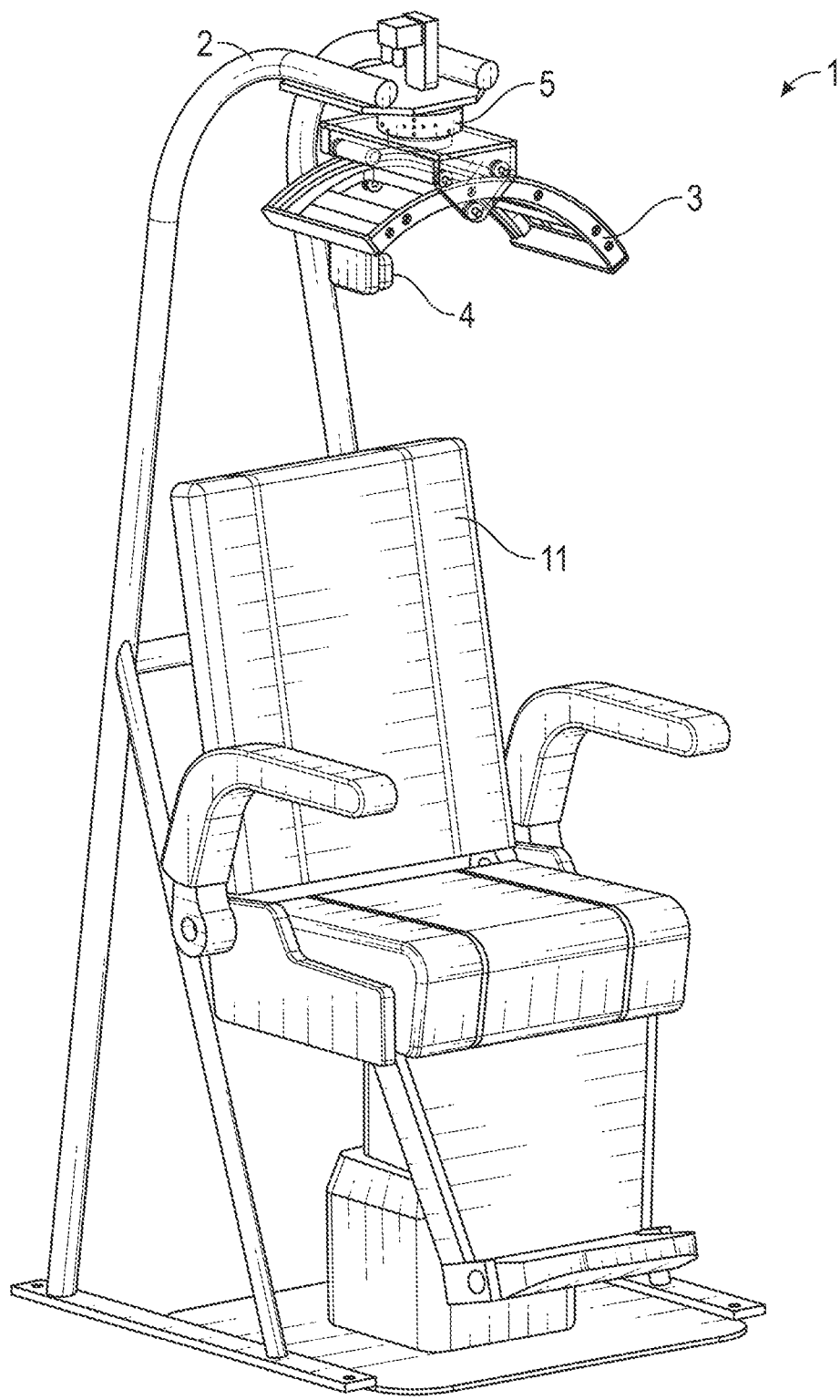

Examples of embodiments of such devices are depicted in FIGS. 1 and 5.

As will be understood, a subject may use such a device to exercise, strengthen, or rehabilitate one or more target neck muscles. Alternatively, or in addition, such a device may be used to analyze or diagnose muscle function and/or injury in a neck region of the subject. In certain embodiments, the receiving surface may be positioned about the head of the subject such that interaction of the subject with the receiving surface will target particular neck muscle(s) for exercise and/or analysis. Exercise may include one or more applications of input force imparted by the subject upon the receiving surface, resulting in "strokes" or repetitions for strengthening of associated neck muscles. Analysis may include one or more applications of input force imparted by the subject upon the receiving surface, details of which may be measured to provide information on neck muscle function and/or range of motion in a particular direction or motion.

It will be recognized that the support frame may include any suitable frame or structure for supporting the device during use. Suitable frames may include a standing frame, a wall or ceiling-mounted frame, or other such structure. In certain embodiments, the support frame may comprise, for example, a standing frame including one or more cantilevered arms for supporting the device, the one or more cantilevered arms supported over a base, and the support frame being sized and shaped to receive a subject. In certain embodiments, the support frame may receive a chair for supporting the subject in a position suitable for interaction with the receiving surface of the device. As will be understood, in certain embodiments, the support frame may be configured for increased structural rigidity to allow use of the device by subjects of varying dimensions and/or weights in a controlled manner to avoid damage and/or injury.

The curved guide arm of the device may include any suitable guide arm or guide rail capable of being supported by the support frame and interacting with the motor assembly. In certain embodiments, the curved guide arm may be substantially curved or arc-shaped to align the receiving surface with the range of motion of a subject's head during use, however it is contemplated that other non-curved guide arms or partially curved guide arms may also be possible for particular applications and/or for particular device designs. By way of example, in certain embodiments, a straight guide arm may be used in designs incorporating a height-adjustable receiving surface, such that the guide arm and height adjustable receiving surface co-operate to follow an arc-shaped path aligned with the range of motion of a subject's head during use.

The receiving surface may comprise any suitable structure for receiving input force from the subject. The receiving surface may comprise, for example, a housing presenting an inwardly facing pad or cushion toward the subject. The receiving surface may be adapted, for example, to comfortably receive or accommodate the subject applying force thereto and may include a consumable covering or surface allowing for sterilization/cleaning between subjects, for example.

The motor assembly may comprise any suitable motorized assembly capable of acting on the guide arm to control or regulate movement of the receiving surface with respect to the subject based on input force received from the subject at the receiving surface during use. The motor assembly may comprise a motor, such as any suitable electric motor known in the art, configured to drive along or otherwise interact with the guide arm to regulate movement/positioning of the receiving surface with respect to the subject over time. In certain embodiments, the motor assembly may comprise a servomotor or a stepper motor, as described in further detail below.

The motor assembly may be configured to respond to input force imparted by the subject on the receiving surface, as is described in detail below. In certain embodiments, for example, the motor assembly may drive, or otherwise allow, motion of the receiving surface in a direction substantially aligned with the subject's input force at a predetermined rate, so long as the input force remains within an allowable tolerance (i.e. above a predetermined force threshold value, for example). The motor may perform such action until, for example, a pre-determined end position or suitable stopping point for the receiving surface is reached. Furthermore, in certain embodiments, the motor assembly may be used to stop movement of the receiving surface immediately upon interruption of the input force applied by the subject, thereby protecting against "snap back" injury to the subject. In certain embodiments, the motor assembly may be configured to provide isometric exercise, isokinetic exercise, or both, to the subject during use, and/or may be configured to allow for assessment of muscle function, range of motion, or both, of the subject during use.

In certain embodiments, the motor assembly may be configured to provide a holding torque maintaining the receiving surface in a fixed position until input force from the subject on the receiving surface reaches an allowable tolerance (i.e. above a predetermined force threshold value, for example), at which point a motor of the motor assembly may activate to drive the receiving surface in a direction substantially aligned with the subject's input force at a predetermined rate, so long as the input force remains within the allowable tolerance. The motor may perform such action until, for example, a pre-determined end position or suitable stopping point for the receiving surface is reached. In such embodiments, although the subject may experience a sensation that they are pushing the receiving surface away (or toward, depending on configuration and/or application), it is the motor assembly which is actually controlling location of the receiving surface (i.e. the motor is not "back driven" by the subject; rather, the motor assembly is activated by the subject's input force to alter position of the receiving surface).

In certain embodiments, the receiving surface may be fixedly mounted to, or integrated with, the guide arm (optionally, at or near an end of the guide arm), and the motor assembly may be mounted to the support frame and control movement of the curved guide arm, such that movement of the receiving surface with respect to the subject is determined/regulated by movement of the curved guide arm driven by or otherwise acted on by the motor assembly. An example of an embodiment of such a device is depicted in FIGS. 1-4.

Figure 2:
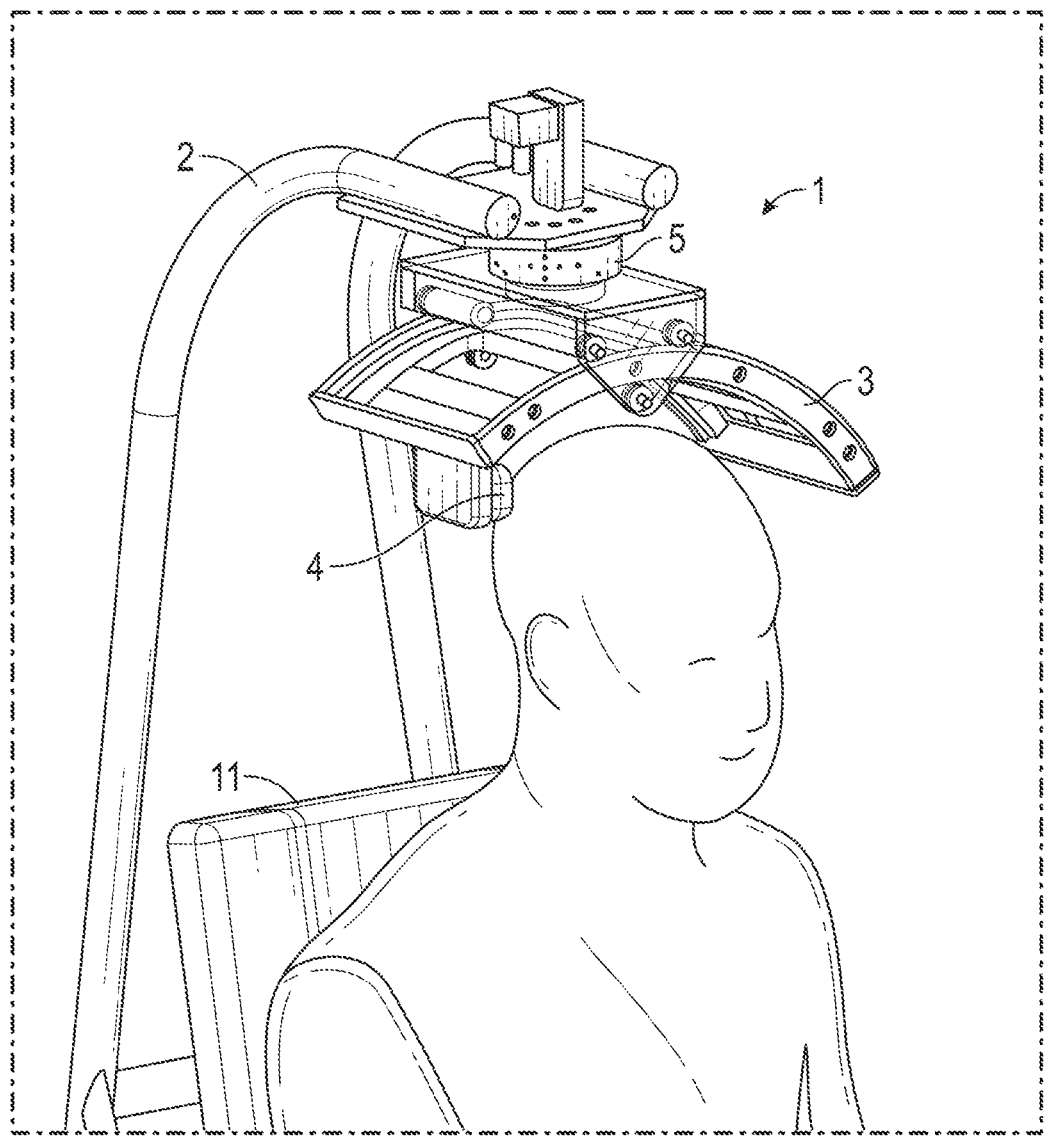
FIG. 2 shows an enlarged perspective view of an upper portion of the device embodiment of FIG. 1, with a subject preparing to use the device.
Figure 3:
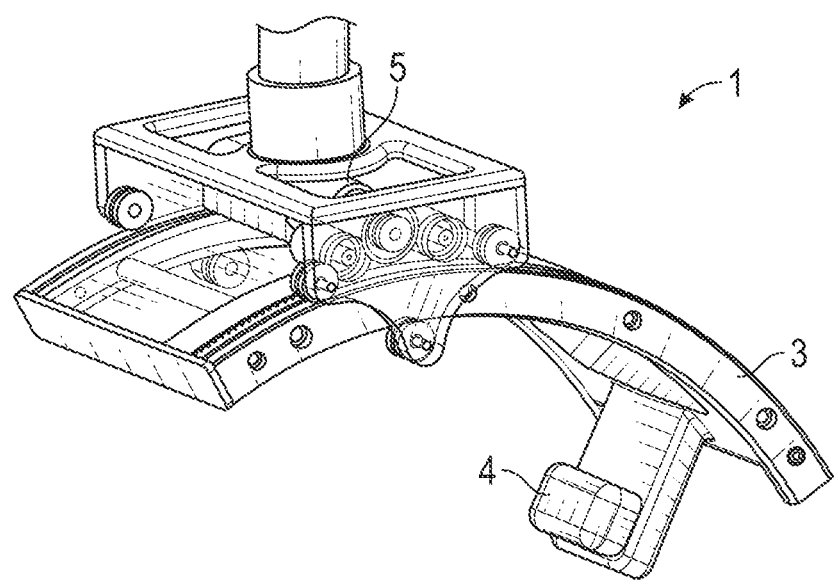
FIG. 3 shows another perspective view of the upper portion of the device embodiment of FIG. 1, with a portion of the outer casing made transparent to show interaction between the motor assembly and the curved guide arm.
Figure 4:
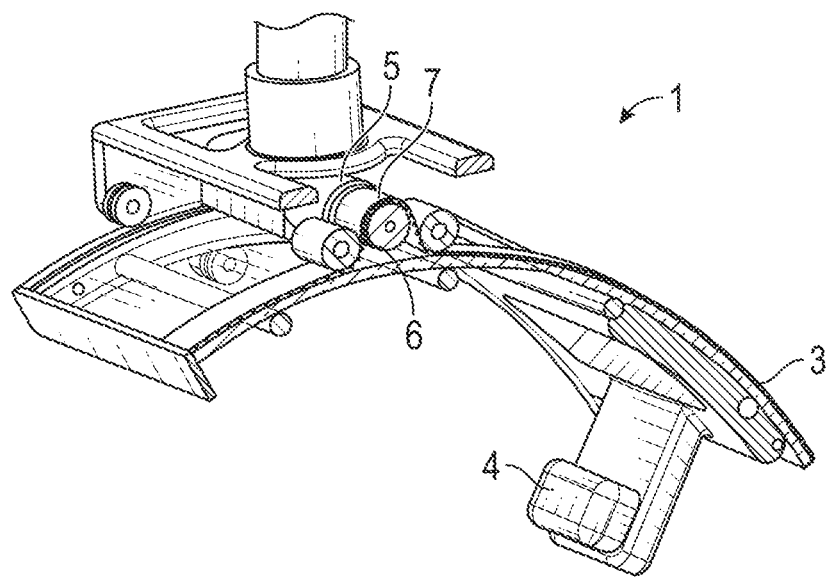
FIG. 4 shows another perspective view of the upper portion of the device embodiment of FIG. 1, with certain portions removed to show non-slip complementary engagement members of the curved guide arm and the motor assembly.

In certain examples of such embodiments, the guide arm (3) may be moveably mounted with the support frame (2) via, for example, a number of wheels or rollers disposed on opposing faces of the guide arm which constrain motion of the guide arm along an arc-shaped path (as shown in FIGS. 2-4). By way of example, the support frame (2) and/or motor assembly (5) mounted thereto may comprise one or more support wheels or rollers disposed at or near each opposing edge of the guide arm (3) and beneath the guide arm (3) so as to support the guide arm (3) from below, wherein the guide arm (3) may comprise corresponding tracks or grooves to rollably engage the support wheels or rollers. The support frame (2) and/or motor assembly (5) mounted thereto may also comprise one or more one or more support wheels or rollers disposed above the guide arm (3) at or near opposing edges of the guide arm (3) so as to limit upward movement of the guide arm (3), wherein the guide arm (3) may comprise corresponding tracks or grooves to rollably engage the support wheels or rollers. In such embodiments, the guide arm (3) may be sandwiched between the support wheels or rollers above and below, which together may limit motion of the guide arm (3) along its arc.

In certain such embodiments, the support wheels or rollers may be rotatably mounted to corresponding support plates disposed at or near opposite edges of the guide arm (see FIGS. 3-4). The support plates may be fixed or integral with a suspension plate, which may be a web, such that the support plates suspend from the suspension plate at or near the opposite edges of the guide arm. The suspension plate may be affixed or integral with a suspension post, which may include a joint at or near a planar center of the suspension plate, to suspend the suspension plate from the suspension post. Thusly, the weight of the guide arm may be borne ultimately by the suspension post.

It will be recognized that several mounting configurations for the motor assembly and the guide arm may be possible and may be selected to suit a particular application.

As will be understood, in certain embodiments, devices described herein having a curved guide arm and a motor assembly mounted to the support frame, for example, may provide a rotational actuator-type mechanism in which the motor actuates the guide arm from outside the circular axis of motion. In such manner, the device may provide a "hollow" axis, which may be more user friendly as the mechanism is away from the user and may facilitate articulation around a stationary user without involving extensive machine setup and configuration. Further, in embodiments in which the force sensor is integrated directly inline with the force applied by the user (i.e. where the input sensor is integrated or combined with the receiving surface), accuracy of the force reading may be enhanced as compared to determining applied load later in the drive train of the machine. An example of such embodiments is depicted in FIG. 15.

In the device (1) embodiment depicted in FIGS. 1-4, the motor assembly may be configured to respond to input force imparted by the subject on the receiving surface (4) to provide isometric exercise, isokinetic exercise, or both, to the subject during use, and/or to allow for assessment of muscle function, range of motion, or both, of the subject during use. In certain embodiments, for example, the motor assembly (5) may drive, or otherwise allow movement of, the receiving surface (4) away from the subject (by acting on the curved guide arm (3)) in a direction substantially aligned with the subject's input force at a predetermined rate, so long as the input force from the subject remains within an allowable tolerance (i.e. above a predetermined force threshold value, for example). The motor may perform such action until, for example, a pre-determined or pre-set end position or suitable stopping point for the receiving surface is reached. As will be understood, in certain embodiments, such a pre-determined or pre-set end position may be adjustable or selectable to suit a particular subject or particular application as needed. Furthermore, in certain embodiments, the motor assembly (5) may be used to stop movement of the receiving surface (4) immediately upon interruption of the input force applied by the subject, thereby protecting against "snap back" injury to the subject.

In alternative embodiments, the receiving surface (4) may be movably mounted to the curved guide arm (3), and the motor assembly (5) may be mounted to the curved guide arm (3) and control movement of the receiving surface (4) along the curved guide arm (3), such that movement of the receiving surface (4) with respect to the subject is determined/regulated by movement of the receiving surface (4)

along the curved guide arm (3) by the motor assembly (5). An example of an embodiment of such a device is depicted in FIGS. 5-10.

Figure 6:
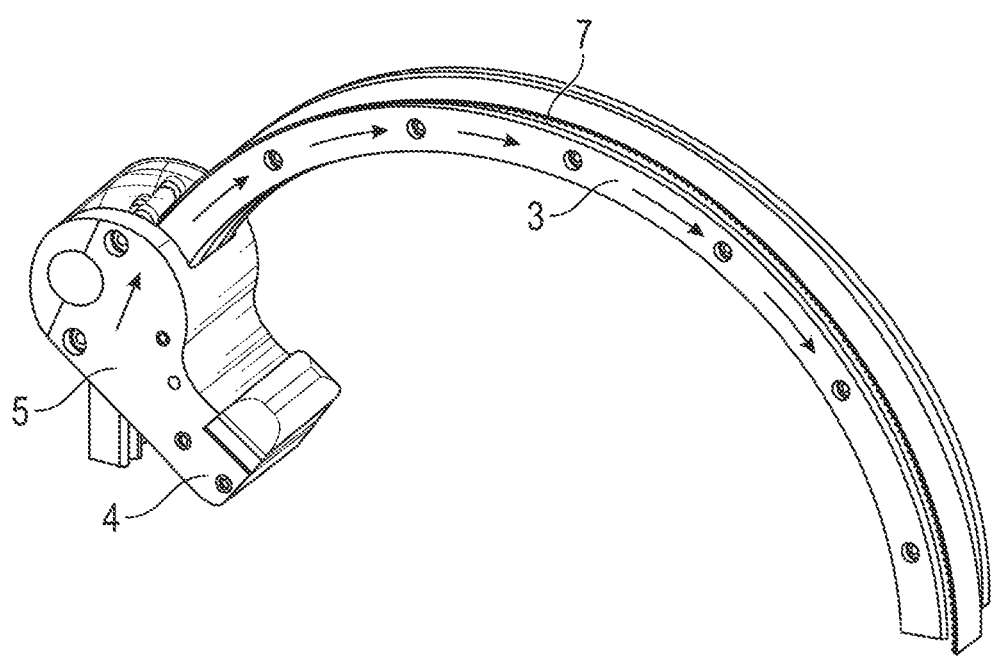
FIG. 6 shows a perspective view of the curved guide arm, motor assembly, and receiving surface of the device embodiment of FIG. 5.

In certain examples of such embodiments, the receiving surface (4) may be movably mounted to the guide arm (3) such that the receiving surface (4) can travel along the guide arm (3). In the embodiment depicted in FIGS. 5-10, the receiving surface (4) is movably mounted to the guide arm (3) via the motor assembly (5), which is located between the receiving surface (4) and the guide arm (3). As shown in FIG. 6, in the illustrated embodiment the receiving surface (4) travels along the curved guide arm (3) under control of the motor assembly (5), which engages with the curved guide arm (3). Although depicted moving in a rightward direction along the guide arm (3), the motor assembly (5) may also drive or otherwise allow motion in the opposite direction (i.e. in the leftward direction) as needed.

It will be recognized that several mounting configurations for the motor assembly and the guide arm may be possible, and may be selected to suit a particular application.

In the device (1) embodiment depicted in FIGS. 5-10, the motor assembly (5) may be configured to respond to input force imparted by the subject on the receiving surface (4) so as to provide isometric exercise, isokinetic exercise, or both, to the subject during use, and/or to allow for assessment of muscle function, range of motion, or both, of the subject during use. In certain embodiments, for example, the motor assembly (5) may drive or otherwise allow or cause motion of the receiving surface (4) away from the subject (by traversing along the curved guide arm (3)) in a direction substantially aligned with the subject's input force at a predetermined rate, so long as the input force from the subject remains within an allowable tolerance (i.e. above a predetermined force threshold value, for example). The motor may perform such action until, for example, a pre-determined or pre-set end position or suitable stopping point for the receiving surface is reached. As will be understood, in certain embodiments, such a pre-determined or pre-set end position may be adjustable or selectable to suit a particular subject or particular application as needed. Furthermore, in certain embodiments, the motor assembly (5) may be used to stop movement of the receiving surface (4) immediately upon interruption of the input force applied by the subject, thereby protecting against "snap back" injury to the subject.

As will be understood, in certain embodiments of the devices described herein, the motor assembly (5) may engage with the curved guide arm (3) via one or more substantially non-slip complementary engagement members located on the motor assembly and curved guide arm. Examples of such non-slip complementary engagement members are shown in each of FIGS. 4, 6, and 7.

By way of example, in embodiments the motor assembly (5) may comprise a motor operable to turn a drive gear-type non-slip complementary engagement member (6), which may be disposed at or near one of the edges of the guide arm (3), wherein the drive gear (6) may be disposed and configured to engage a cooperating curvilinear gear bar-type non-slip complementary engagement member (7) provided at or on a facing surface of the guide arm (3), in a rack-and-pinion arrangement. Alternatively, the drive gear-type non-slip complementary engagement member may be a primary gear, which may engage one or more secondary gears which in turn engage the curvilinear gear bar or rack-type non-slip complementary engagement member, again to move in a rack-and-pinion fashion. Alternatively, and as shown in FIG. 4, the support frame (2) and/or motor assembly (5) may further include support rollers disposed on opposite sides of a drive gear-type non-slip complementary engagement member (6), each to sandwich between the support roller and the drive gear (6) a toothed belt or timing belt-type non-slip complementary engagement member (7) which engages the drive gear (6), and further to press the timing belt (7) against a cooperating toothed curvilinear bar gear or rack provided at or on the upper surface of the guide arm. Alternatively, the timing belt (7) may be affixed at its ends to the guide arm at joints with the guide arm adjacent opposite ends of the guide arm along its arc.

Figure 7:
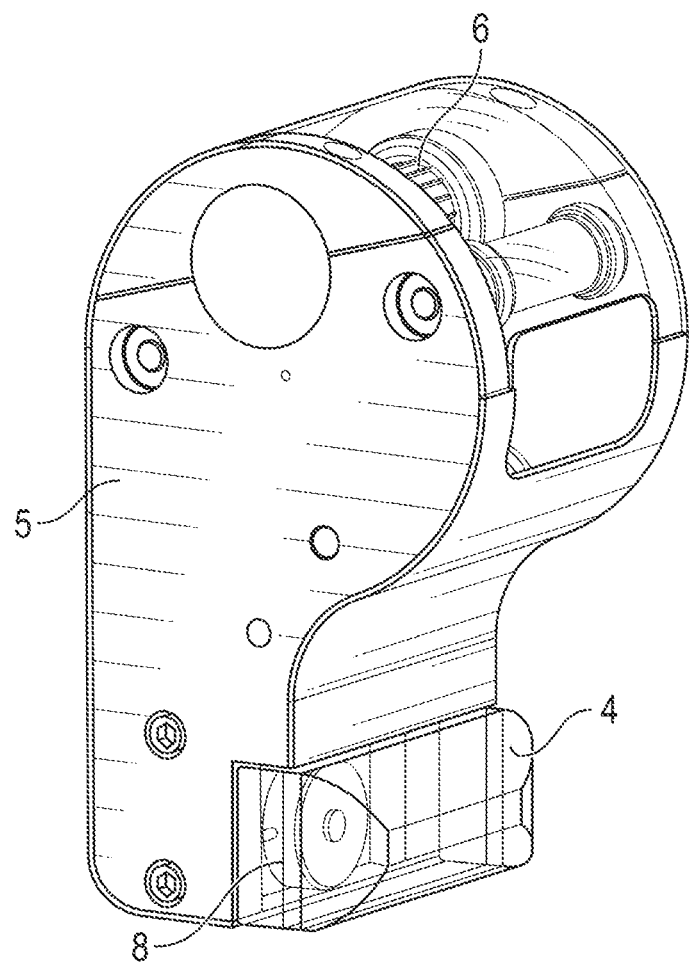
FIG. 7 shows a perspective view of the motor assembly and receiving surface of the device embodiment of FIG. 5, with certain surfaces made transparent to show a complementary engagement member of the motor assembly, and a force sensor located behind the receiving surface.
Figure 8:
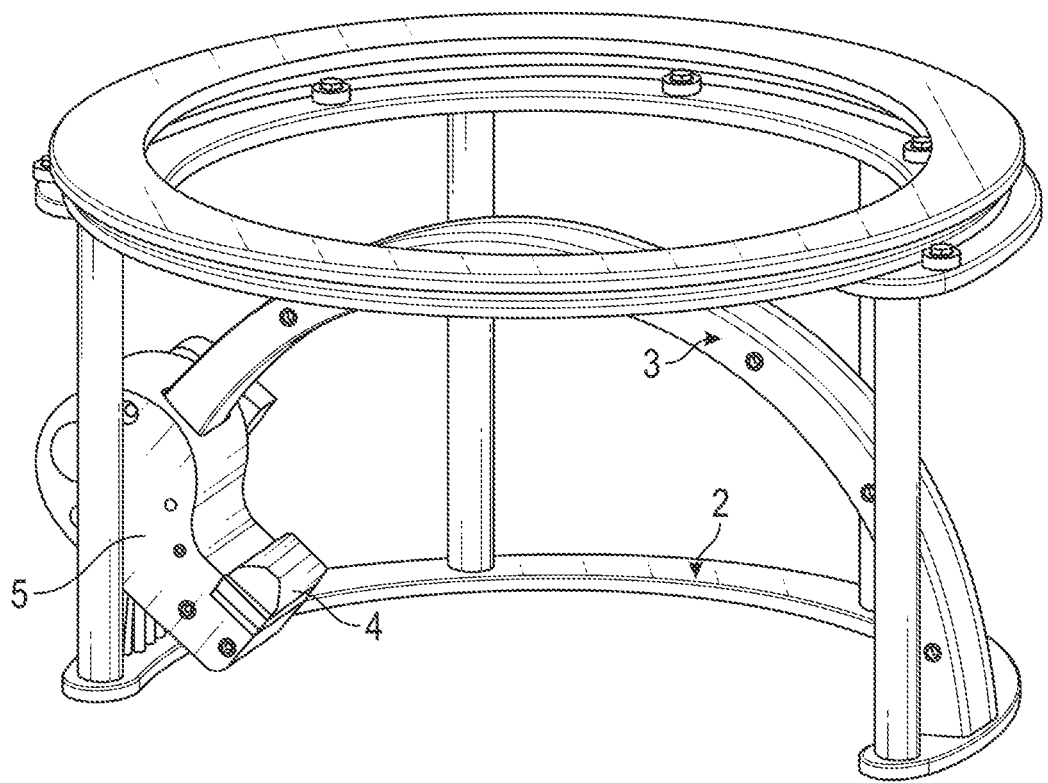
FIG. 8 shows a perspective view of the curved guide arm, motor assembly, receiving surface, and a portion of the support frame of the device embodiment of FIG. 5.

By way of further example, and as shown in FIGS. 6 and 7, the motor assembly (5) may comprise a motor driving a toothed gear-type non-slip complementary engagement member (6), which may engage with the curved guide arm (3) via one or more non-slip complementary engagement members in communication with, or integrated with, the guide arm (3). In the embodiment depicted in FIG. 6, the toothed gear-type non-slip complementary engagement member (6) engages with the curved guide arm (3) via a timing belt in a manner related to that already described above in relation to FIG. 4, however it will be recognized that in alternative configurations the toothed gear-type non-slip complementary engagement member (6) might, for example, engage with the curved guide arm (3) directly via a non-slip complementary engagement member (7) which may be directly integrated or joined with the curved guide arm (3).

The skilled person having regard to the teachings herein will recognize that other arrangements between the motor assembly and the guide arm are possible and will be able to select a suitable design to fit a particular application such that the motor assembly is operable to cause motion of the receiving surface with respect to the subject along a path dictated by the guide arm.

As will be understood, the motor assembly of the devices described herein may be configured to operate in response to, or based on, input force received from the subject at the receiving surface. In certain embodiments, the device may comprise one or more input sensor(s) (8) for sensing input force received from the subject at the receiving surface (4), and transmitting a control signal based on the input force. In certain embodiments, such as that depicted in FIG. 7, the one or more input sensor(s) (8) may be located at the receiving surface (4). In certain alternative or additional embodiments, the motor assembly (5) may comprise the input sensor (8), which may sense the force exerted on the receiving surface (4) either directly or indirectly. The skilled person having regard to the teachings herein will be able to select suitable input sensor(s), and input sensor location(s), to suit a particular application, and will be able to configure the input sensor(s) to communicate sensed information (in the form of, for example, a control signal) to the controller/motor assembly appropriately. The controller may be implemented, by way of example, in numerous ways including as software running on a computer or computing device, as an application specific integrated circuit (ASIC), a field programmable gate array (FPGA), a microcontroller, etc. The controller may be provided by a combination of hardware and software, including firmware, executing on the hardware to provide the controller functionality described above. Regardless of the particular implementation, the controller may be connected to sensors and actuators, such as the motor(s), and control the actuators based on, at least, the information received from the sensors.

By way of example, the receiving surface and/or the motor assembly may be provided with one or more sensors to sense force exerted on the receiving surface (either directly, or via the guide arm, for example).

In certain embodiments, one or more input sensor(s) (i.e. force sensor(s)) may be provided in or about the receiving surface and may be sandwiched between a pad and a pad housing of the receiving surface, for example. The input sensor may include, for example, a piezoelectric force sensor, a force-sensing resistor, one or more load cells, or any other force-sensing device(s). The input sensor may be interfaced to the controller and/or the motor assembly, and the controller may control the motor as described herein based on a control signal received from the input sensor.

In certain embodiments, the input sensor may comprise any suitable sensor(s) known to the person of skill in the art having regard to the teachings herein. Previously, exercise machines have sometimes employed a strain gauge to read force applied by a user. However, such strain gauges have sometimes been placed in a mechanical linkage such that the strain gauge reading may be subjective due to length of a torque arm (particularly where torque arm length is adjustable) and/or due to variations in where the user applies pressure on the torque arm (which may create different load readings even though the force may be substantially the same). Furthermore, attachment of a strain gauge to a metal component may reduce accuracy, as the metal component may deform under stress, and/or may be affected by manufacturing tolerances, metallurgy consistency, and/or temperature. Where wires are used to convey the input force or control signal to the controller, such wires may be more prone to breakage due to motions of the device. Thus, in embodiments where high input sensor reading accuracy is desirable, it is contemplated that the input sensor may comprise one or more load cell(s) or other sensor(s) located directly inline with the force being applied by the user. In certain embodiments, the input sensor may be located directly inline with the force being applied by the user by integrating the input sensor with the receiving surface. Further, in certain embodiments, a ball joint linkage may be included which is configured to maintain user force substantially perpendicular to the load cell(s) along the actuation path of the device during use.

An example of such a device configured for high input sensor accuracy is depicted in FIG. 14. The device includes a load cell-based input sensor integrated with receiving surface (4), and a ball joint linkage (16) integrated with the receiving surface to maintain the user force substantially perpendicular to the input sensor along the actuation path of the device during use. In the depicted example, the input sensor includes a wireless transceiver communicating with the controller, thereby avoiding use of wiring to the load cells. In the depicted example, the receiving surface (4) includes one or more input sensors (13) (in this example, in the form of one or more load cells including an amplifier), along with a microcontroller (14), a power supply, and a wireless transceiver (15). In this embodiment, a master node is utilized to process the received data and control the motor assembly depending on the selected protocol with which the device is operating.

In certain embodiments, the motor assembly may include a servomotor comprising an electric motor coupled to a position sensor for position feedback, and torque sensor for torque feedback, which may be coupled to a controller. In certain embodiments, the servomotor may be connected to a gearbox to reduce speed and increase torque, and/or to prevent "back driving" of the receiving surface. In certain further embodiments, the servomotor may be coupled to drive a timing belt via a drive gear, as described hereinabove. Such a servomotor configuration may be incorporated in, for example, the design depicted in FIG. 2. In such embodiments, when a subject applies force on the pad of the receiving surface by pressing his or her head thereon, the input force may be communicated up the receiving surface to the guide arm, and through the timing belt to the drive gear, or otherwise directly or indirectly to the drive gear, thereby affecting the torque generator at the motor. When the motor is a servomotor, the torque generated in the servomotor may be correlated to the force applied on the receiving surface, thus providing force input information and rendering additional force gauge(s) unnecessary and/or optional. In certain embodiments, the servomotor controller may be coupled to the servomotor to sense the torque developed in the servomotor, and the position sensor to sense the relative position of the guide arm and/or receiving surface, and to actuate the servomotor in response according to preconfigured parameters. In certain embodiments, the servomotor may instead be a stepper-type motor, or other suitable motor.

In such embodiments comprising, for example, a servomotor configuration, for both isometric and isokinetic exercises, a position of the motor may be preconfigured, and force applied to the receiving surface by the subject's head (which tends to move or accelerate the guide arm via the receiving surface, or to move or accelerate the receiving surface itself, depending on design) may be countered by the motor via the controller adjusting the torque generated by the servomotor to cancel the torque generated by the force applied to the receiving surface.

In certain embodiments, the motor assembly may include a stepper motor, or any other suitable motor known to the skilled person. It has been found that stepper motors, for example, may, in certain embodiments, provide for improved safety and/or cost effectiveness over servo motors. Since servo motors may operate at high speed, stepper motors may be desirable in certain embodiments as they loose torque at high rpm, providing for inherent safety since they skip when trying to go fast. Further, in certain embodiments, stepper motors may allow for avoiding using of an expensive and/or complex gearbox, which may provide for cost-effectiveness and/or may allow for the motor to be more easily replaceable during maintenance or upgrading, for example.

In another embodiment of the above device or devices, the motor assembly may be configured to move the receiving surface in a direction substantially aligned with the input force at a predetermined rate, so long as the input force remains within an allowable tolerance. The motor assembly may perform such action until, for example, a pre-determined or pre-set end position or suitable stopping point for the receiving surface is reached. FIGS. 9 and 10 depict such movement of the receiving surface in response to input force from the subject. In FIG. 9(A), the subject engages with the receiving surface of the device and begins to apply input force thereto. Once a predetermined minimum input force threshold is reached (as determined by an input force sensor located, in this example, with the receiving surface), the motor assembly provides controlled motion of the receiving surface away from the subject, as shown in FIG. 9(B), along an arc-shaped path dictated by the curved guide arm at a predetermined rate as long as the minimum input force threshold is maintained on the receiving surface. In the depicted embodiment, the motor assembly provides the controlled motion by actively driving along the curved guide arm. In such configuration, the rate at which the receiving surface moves away from the subject in the direction substantially aligned with the input force (or in a pre-determined direction suitable for the exercise or analysis to be performed) is controlled by the motor assembly.

As described above, the motor assembly may further be configured to stop movement of the receiving surface with respect to the subject upon interruption of the input force from the subject upon the receiving surface, upon failure of the input force to remain within an allowable tolerance, or both.

As will be understood, the allowable tolerance may comprise, for example, a lower threshold value for the input force to exceed, an upper threshold value for the input force to not exceed, an acceptable direction vector range for the input force to align within, one or more other suitable predetermined parameters, or any combination thereof.

FIG. 10 depicts action similar to that of FIG. 9, but with the curved guide arm rotated to a new position with respect to the subject, thereby exercising and/or analyzing different neck region muscle(s). As can be seen, positioning of the curved guide arm and receiving surface with respect to the subject can be used to target specific neck region muscle(s) for exercise and/or analysis. In the embodiments illustrated in FIGS. 1-10, the curved guide arm and receiving surface is rotatable 360° around the subject about a vertical axis, however it is contemplated that configurations with less than 360° range of rotation, or fixed configurations, may also be possible depending on desired application.

In still further embodiments of the above devices, the device may further comprise a positioning sensor which tracks location of the receiving surface, location of the guide arm, head positioning of the subject, or a combination thereof, in space. Such a positioning sensor may be located on the subject, on the receiving surface, on the guide arm, or integrated with the motor assembly, for example. In certain embodiments, position tracking may be accomplished by tracking action of the motor assembly over time (for example, number and direction of motor revolutions), which in turn provides location information for the receiving surface. In certain embodiments, position tracking may be accomplished using any suitable position tracking system which will be known to the person of skill in the art having regard to the teachings herein. For example, a suitable camera-based position tracking system, an accelerometer-based position tracking system, or another wired or wireless position tracking or detecting system may be used. Accurate position tracking during use of the device may, for example, facilitate Range of Motion (ROM) analysis of the subject, or may be used to provide tailored feedback/guidance to the subject during use, for example.

In certain embodiments, the positioning sensor may include any means suitable to sense a relative position of the curved guide arm and/or the receiving surface along its path. The positioning sensor may include a rotational sensor which, when the motor is a servomotor, may be included in or with the servomotor such as an absolute encoder of the servomotor, for example. The relative position of the guide arm may thus be deducible from the rotational position of the drive gear in such configurations. In such case, the absolute encoder may be manually calibrated to correlate the rotational position of the drive gear and the position of the guide arm and/or receiving surface along its arc path, for example.

In certain embodiments of the above device or devices, the guide arm may be rotatable with respect to the support frame about a substantially vertical axis, allowing for positioning of the receiving surface about at least a portion of an outer perimeter region surrounding the subject such that the receiving surface may be suitably positioned at a location adapted for the particular exercise/analysis to be performed and/or the particular body region to be targeted. In certain embodiments, the guide arm may be rotatable a full 360° about the vertical axis, such that the receiving surface (and the path along with the receiving surface may follow when input force is applied thereto) may be fully adjustable with respect to the subject. In the device embodiments depicted in FIGS. 2 and 8, full 360° rotation is possible through rotation of the guide arm and motor assembly about the support frame. It is, however, also contemplated that in certain embodiments configurations with less than 360° range of rotation, or fixed configurations, may also be possible depending on desired application. In certain embodiments, rotation about the vertical axis may be either automated or manual and may include one or more sensors or markings allowing for precise positioning around the vertical axis. In certain embodiments, once the guide arm/receiving surface is suitably positioned about the user, further rotation of the guide arm about the vertical axis (i.e. around the user) may be restricted or locked, such that the user may perform the exercise/analysis along a path predetermined by the orientation of the guide arm. In certain embodiments, rotation of the guide arm about the vertical axis (i.e. around the user) may be restricted or locked while the user is performing an exercise/assessment exertion on the receiving surface.

In certain embodiments of the above devices, the device may comprise a seat for the subject which orients the neck region of the subject with the receiving surface. The device embodiments depicted in FIGS. 1 and 5 each include a seat (11) for the subject. As will be understood, the seat, the support frame, and/or the mount of the suspension post to the supporting frame may be adjustable to vary a relative height or vertical position, to allow positioning of the receiving surface adjacent the side of the head of the subject.

In further embodiments, the device may further comprise one or more storage cabinets, and the one or more cabinets may be bolted or otherwise affixed to the standing frame.

As described herein, embodiments of the above devices may include a motor assembly configured or programmed to control movement of the receiving surface with respect to the subject to provide isometric exercise, isokinetic exercise, or both, to the subject during use; to assess range of motion of the subject during use; or a combination thereof.

Figure 11B:
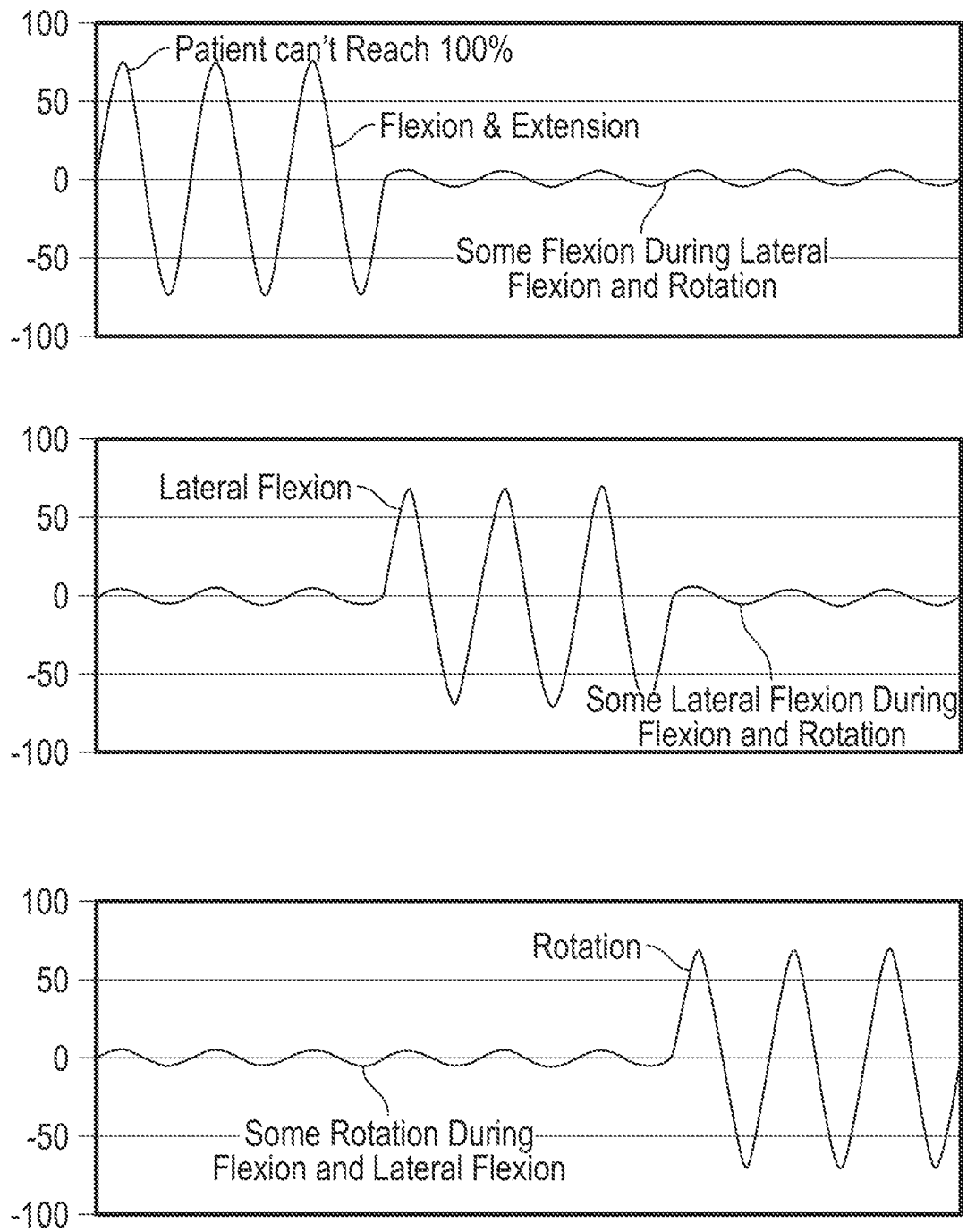

Range of motion (ROM) assessment may, for example, employ a positioning sensor as described herein above to track and assess a subject's ROM in particular direction(s). FIG. 11(A) provides a simulated ROM read out for a healthy subject being analyzed for [1] flexion and extension; [2] lateral flexion; and [3] rotation range of motion. FIG. 11(B) provides a corresponding simulated ROM readout of an injured subject. As can be seen, such ROM read outs may facilitate diagnosis and/or assessment of neck injury. In certain embodiments, ROM data obtained from a subject may be compared with a normative dataset, a database of injury-associated ROM data, or both, to further facilitate injury diagnosis and/or analysis.

In certain embodiments, for isometric (i.e. static) exercise or analysis, the subject may apply input force to the receiving surface until a threshold pressure is reached. The subject may then be instructed to hold this input pressure for a set period of time. In such exercise or analysis, the motor assembly may be configured to maintain the receiving surface at a fixed position, thereby providing for static exercise/analysis.

In certain embodiments, for isokinetic (i.e. dynamic) exercise or analysis, the motor assembly and/or controller associated therewith may be preconfigured with a force threshold such that when the input force applied to the receiving surface rises to the force threshold the motor assembly and/or controller actuates the motor (i.e. a servo-motor, for example) to move the guide arm/receiving surface in the direction of the applied force (and/or in a pre-determined direction suitable for the exercise and/or analysis to be performed). The rate of such motion may be a preconfigured rate and may be a relatively slow rate of motion which may be set based on experimentation or based on the particular application. The motor assembly and/or controller may be so configured that when the force applied to the receiving surface by the subject falls below the threshold force, the motor (i.e. a servomotor) ceases motion of the movable frame. The force threshold may be a lower force threshold, and the motor assembly and/or controller may also be configured with an upper force threshold such that if the force applied to the receiving surface by the subject exceeds the upper force threshold an acoustic or visual warning is produced. The device, in certain embodiments, be provided with acoustic or visual warning means or visual warning signal interfaced to the motor assembly and/or controller for the motor assembly and/or controller to signal the warning means or warning signal for such purpose.

As will be understood, devices as described herein may be configured for multiple-axis neck or other joint mechanic or other joint or musculotendious group (for example, rotational joint, flexion/extension joint, etc. . . . ) rehabilitation, strengthening, and/or assessment. In certain embodiments, devices may include motion tracking/processing elements (i.e. an MPU), and/or Bluetooth low energy (BLE) (or other suitable wireless communication such as, for example, xbee, wifi, etc. . . . ) microcontrollers (MCU) which allow communication between device components. In certain embodiments, a tablet computer may be provided as a user interface and/or clinician interface (where the clinician may set up sessions, review subject data, or guide subject use during exercise and/or analysis) and/or as a controller directing operation of the device.

In certain embodiments, a tablet-based computer or other such computer may be used to provide a user interface to a user and may be used to run a software application for guiding the user through a session. User data may be logged and used to identify treatment trends over time. The table-based computer may serve as a centralized client or node, sending and receiving data to/from individual components such as an augmented reality headset and/or the input sensor and/or the motor assembly, for example. In certain embodiments, wireless communications, such as BLE (or other suitable wireless communication such as, for example, xbee, wifi, etc. . . . ), may be used. In certain embodiments, motors may be connected to a two-wire bus with a primary BLE MCU as client. The MCU may be configured to await commands from the tablet-based computer, which may dictate motor position, torque, and speed. The MCU may include its own logic to safely deal with a lost connection to the client, or other errors which may be encountered. In certain embodiments, the input sensor(s) may comprise load cell(s) connected to the BLE MCU. In certain embodiments, the combined components may act as a force gauge inside the receiving surface, allowing accurate capture of the force directly applied by the user.

In certain embodiments, devices described herein may comprise a curved guide arm supported by a support frame, with the curved guide arm being driven by a motor assembly comprising, for example, a stepper motor. The curved guide arm may substantially trace a section of an arc (for example, may trace a portion of a circle), and may have an adjustable support member supporting a receiving surface thereon, which is directed inwardly with reference to the arc, for example directed inwardly toward the center of the arc (i.e. toward the center of the circle). An input sensor, such as a load cell, may be covered by a pad of the receiving surface, and positioned at or near the end of the adjustable support member, providing a cushioned surface upon which a user may push against. The curved guide arm may be configured to rotate about the center axis of the curved guide arm, with force applied to the pad being translated into rotational force on the stepper through a timing belt, for example.

In further embodiments, devices as described herein may include a swivel plate-type element which allows the curved guide arm to rotate about a vertical or substantially vertical axis (or another axis, depending on the desired application/orientation of the device). Rotation about the vertical or substantially vertical axis may be actuated by a stepper motor and a timing belt (for example), or a different motor and/or configuration, to cause the swivel plate to carry the curved guide arm around the user. In certain embodiments, the actuation of the curved guide arm and actuation of the swivel plate may be driven by the same motor, or by different motors. In certain embodiments, wires to the stepper motor may sit on top of the swivel plate in a loose coil and may uncoil/recoil in a slot track to accommodate rotational movement during use. In certain embodiments, the swivel plate may be configured to provide a hard stop once one full rotation has been made. In certain embodiments, two bearings may be used to securely hold the plate and provide rigid rotation.

In certain embodiments of the devices as described herein, an elevation assembly may be provided to raise or lower (i.e. translate) the curved guide arm/receiving surface in relation to the user. In embodiments where, for example, the user's neck is to be exercised or assessed, the elevation assembly may be used to place the axis of the curved guide arm at or in the vicinity of the pivoting axis of the cervical spine of the user. In certain embodiments, a fixed targeting light (76) (see FIG. 34) may be provided which points to the center of the axis of the arc, which may be used to correct alignment around the joint or musculotendinous group or body region. By way of example, the elevation assembly may comprise a height-adjustable chair or may comprise a high-adjustable section of the support frame which allows the curved guide arm and receiving surface to be raised or lowered with respect to the user. In certain embodiments, an electric jack may be provided to vertically translate the curved guide arm using linear bearings, for example. In certain embodiments, a user may be seated in a chair, and then the elevation assembly may be used to bring the curved guide arm to an appropriate position with respect to the user for use. FIG. 17 depicts an embodiment of a device as described herein which includes a chair for the user and a support frame which is height-adjustable to properly orient the curved guide arm/receiving surface with respect to the user based on user height.

In certain embodiments, the support frame of devices described herein may comprise a free-standing base or may be attached to an existing structure such as a wall, for example. In some embodiments, the device may include a chair for the user, or may be configured for use with a chair for the user. In other embodiments, the device may be for use by a standing user.

FIGS. 18A-18G depict an embodiment of a device as described herein shows in perspective views with various components made transparent, where FIGS. 18A-18G show the device embodiment in various exploded views to show components and connectivity therebetween. The depicted device embodiment is one in which the curved guide arm is driven by a motor assembly which is mounted to the support frame to control motion of the curved guide arm with receiving surface mounted thereto, and the device includes a second motor operating a rotational member to which the curved guide arm is mounted such that the curved guide arm can be rotated around the user by the second motor. The supporting frame of the depicted device is height-adjustable such that the curved guide arm (and in this example, the entire upper portion of the device, including the curved guide arm, motors, and associated components) can be translated up and down to accommodate the height of the user.

In certain embodiments, the device may be configured to allow for a user or experienced personnel to either manually or automatically position the receiving surface at a suitable 3D orientation with respect to the user which is appropriate for the size of the user and the particular exercise to be performed. In certain embodiments, the receiving surface may report to a desired 3D position, such as an initiation position for an exercise to be performed, automatically. An example of such automated reporting is depicted in FIGS. 20A and 20B, wherein the user of the device is wearing a headband comprising a motion processing unit (MPU) (26), a power supply, a microcontroller (27), and a radio transceiver chip (28) (FIG. 20A). As shown in FIG. 20B, a master controller may be used to read continual positioning data from the headband. A user, or experienced personnel, may initiate a "follow position mode", in which continual position data from the headband may be used by the master controller to move the vertical and horizontal axis actuators ((23) and (24)) to bring the receiving surface into a suitable initiation position for the exercise to be performed. In certain embodiments, the device may include one or more motors for driving rotation of the receiving surface about a vertical axis (i.e. around the periphery of the user), for driving the receiving surface toward a user via motion of the curved guide arm, and/or for driving the receiving surface toward or away from the curved guide arm to accommodate the proportions of the user and the particular exercise or analysis to be performed.

In further embodiments of the above devices, the device may further comprise a user interface for guiding the subject's interaction with the receiving surface during use. In certain embodiments, for example, the user interface may instruct the subject to apply input force to the receiving surface in a specific manner and provide the subject with real-time feedback allowing the subject to adjust application of input force so as remain within an allowable tolerance. In certain embodiments, the allowable tolerance may comprise a lower threshold value for the input force to exceed, an upper threshold value for the input force to not exceed, an acceptable direction vector range for the input force to align within, or any combination thereof.

In further embodiments, the user interface may comprise a graphical interface displayed to the subject during use, an auditory interface played for the subject during use, or a combination thereof. The user interface may, for example, comprise a graphical user interface which provides an immersive visual experience to the subject during use which guides interaction of the subject with the receiving surface.

As will be understood, in certain embodiments, devices described herein may be configured or pre-programmed to provide a fully or nearly fully autonomous exercise or analysis session to a user with minimal or no direct supervision from clinical personnel.

In certain examples, the device may include a user interface for providing feedback which may include light or sound generation means or sound generator, such as a buzzer, light, or display, interfaced with a controller. For example, as shown in FIG. 13, the user interface may include a display visible to the subject which illustrates to the subject the direction and amount of force for the exercise, and which adjusts based on the amount of input force actually applied by the subject. The controller may be configured to generate such feedback, or the device may be provided with or interface with a further feedback controller, such as a computer, which generates such feedback via the display or other feedback means (or feedback control). The controller or feedback controller may also be configured to display instructions on the display to guide the subject through the exercise. In certain embodiments, the user interface may, optionally, be displayed on or integrated within an optional surface (12) surrounding the subject, for example. In certain embodiments, the user interface may be presented to the subject via a headset unit or virtual reality/augmented reality goggles/glasses/display worn by the subject during use and interfaced with the device. In FIG. 14, for example, a device embodiment is depicted which includes augmented reality goggles (17) which present the user interface to the subject during use.

In certain embodiments, for example, the device may comprise a BLE (or other suitable wireless communication such as, for example, xbee, wifi, etc. . . . ) MCU/MPU-based augmented reality (AR) headset and/or other devices, which may be used to gather positional data on a user during treatment or analysis. Such data may be used to assess, for example, range of motion, and/or to facilitate correct user treatment during operation. The AR headset may provide a user with a heads-up display, which may guide them through their activity while allowing them to continue to see the environment around them, improving safety.

In certain embodiments, the AR headset may provide the user with a visually displayed object (such as, for example, a scalene triangle or other shape), and a visually displayed target region into which the user should try and orient the displayed object by moving a body part (i.e. the head, where the neck is to be exercised or assessed). The visually displayed object and target region may be displayed such that the two only overlap when the user's body part is properly oriented for correct usage of the device. Once the user's body part is properly positioned, the receiving surface may be either manually or automatically driven to abut the user's body part, and the session may begin. In certain embodiments, the AR headset may additionally be used to guide the user through the session, providing visual prompts as to how the user's body part should be moved (i.e. how quickly, and in which direction, for example).

In certain embodiments, AR or VR may be used to provide immersive user instruction. Correct positioning of the user during exercise is highly desired in many applications. Traditionally, the presence of experienced personnel has been needed to ensure correct user interactions to activate desired muscles. Visually immersive instruction technology may allow for less supervision of the user during use of the devices described herein. Augmented reality glasses or another such "heads-up" display may be used to provide user instruction, whereby immersive visual systems using motion processing MEMs, or camera tracking, to provide yaw, pitch, and roll data of a headset or users head or body part are employed. Such data may be used to visually instruct a user to move to their body part (for example, their head where the neck is to be exercised) into a specific position in 3D. Once the user is in the correct position, a pre-programmed exercise may be carried out with high accuracy. FIG. 19 illustrates an example of guided immersive head positioning. In step 1, a user is presented with a shape (18) from a headset (17), which appears projected in front of the user. A fixed target region (19) (i.e. a fixed corresponding shape) remains in place as a target for the user. In step 2, the user aligns the shape (18) with the target region (19), which accordingly positions the user's head correctly in 3D for initiation of the exercise or assessment. The device receives co-ordinates from the glasses when the user's head is in place, and in step 3 the received co-ordinates are used to drive the curved guide arm and receiving surface from resting position (22) to the user (i.e. the receiving surface reports to the correct position (21) once the user is in position). In step 4, the user applies force to the receiving surface, causing the motor to drive the curved guide arm/receiving surface away from the user so long as the applied force is within a desired range or at or above a target threshold.

A connection diagram of a device embodiment as described herein comprising a tablet-based computer for providing user input and controlling the device, and comprising an AR headset (in this example, an Epson Moverio AR headset) for guiding user operation, is depicted in FIG. 16. The depicted diagram may be considered as an example of a mesh network and is intended for illustrative purposes for the person of skill in the art. It will be understood that various substitutions, deletions, additions, or modifications may be made to suit a desired application, and that various other configurations may be used. In certain embodiments, the tablet and/or AR glasses may be omitted, for example, and the master node may be adapted accordingly.

In another embodiment of the above devices, the device may further comprise an administrator user interface for selecting the exercise and/or analysis parameters for the subject. By way of example, the device may provide an administrator user interface to medical personnel, allowing configuration of the device to perform specific exercises and/or analysis tailored to the particular subject and/or the suspected injury type. FIGS. 12(A) and 12(B) provide examples of such administrator interfaces which may be used.

As will be understood, in certain embodiments, user interfaces and/or device operational parameters and/or instructions for operation of the motor assembly and/or the user interface and/or computer programs relating thereto may be provided and stored on a computer-readable medium which may be interfaced or integrated with the device.

The computer-readable medium can be any suitable tangible, non-transitory medium, including magnetic, optical, or electrical storage medium including a diskette, compact disk read only memory (CD-ROM), memory device (volatile or non-volatile), or similar storage mechanism. The computer-readable medium may contain various sets of instructions, code sequences, configuration information, or other data, which, when executed, may cause a processor to perform steps in a method according to an embodiment as described herein. Those of skill in the art will appreciate that other instructions and operations for implementing the described implementations may be possible and may also be stored on the computer-readable medium. The instructions stored on the machine-readable medium may be executed by a processor or other suitable processing device and may interface with circuitry to perform the described tasks.

In another embodiment of the above device or devices, the device may comprise one or more sensors monitoring the position of the subject. By way of example, the device may comprise one or more sensors for monitoring the position of the back and/or shoulders of the subject during use. Such sensors may be used to, for example, verify that motion of the head against the receiving surface is being generated by muscles in the neck rather than tilting of the upper body (i.e., the sensors may monitor/verify that the subject's back and/or shoulders remain substantially stationary during use). In certain embodiments, such sensors may trigger a feedback signal (i.e. an audio or visual signal) for the subject if improper movement of the back and/or shoulders is detected during use.

In another embodiment, there is provided herein a method for exercising or analyzing a neck region of a subject, the method comprising:
  instructing the subject to apply an input force to a receiving surface;
  sensing the input force applied to the receiving surface over time; and
  controlling movement of the receiving surface with respect to the subject based on the input force received from the subject at the receiving surface using a motor assembly,
whereby the motor assembly drives the receiving surface in a direction substantially aligned with the input force at a predetermined rate, so long as the input force remains within an allowable tolerance, thereby exercising or analyzing function of the neck region. The motor assembly may perform such action until, for example, a pre-determined or pre-set end position or suitable stopping point for the receiving surface is reached.

In certain embodiments, the motor assembly may stop movement of the receiving surface with respect to the subject upon sensed interruption of the input force from the subject upon the receiving surface, upon sensed failure of the input force to remain within the allowable tolerance, or both. In certain embodiments, the allowable tolerance may comprise a lower threshold value for the input force to exceed, an upper threshold value for the input force to not exceed, an acceptable direction vector range for the input force to align within, or any combination thereof.

In still another embodiment, the motor assembly may control movement of the receiving surface with respect to the subject as part of the method, to provide isometric exercise, isokinetic exercise, or both, to the subject; to assess range of motion of the subject; or a combination thereof.

As will be understood, such methods may comprise tracking location of the receiving surface, head positioning of the subject, or both, in 3D space over time as described hereinabove. Such positioning information may be used to facilitate, for example, injury analysis of the subject.

In further embodiments, the instructing step of the method may comprise providing a user interface guiding the subject's interaction with the receiving surface. The user interface may, for example, instruct the subject to apply input force to the receiving surface in a specific manner, and may provide the subject with real-time feedback allowing the subject to adjust application of input force so as remain within the allowable tolerance. In yet another embodiment, the user interface may comprise a graphical interface, an auditory interface, or a combination thereof. In certain embodiments, the user interface may comprise a graphical user interface which provides an immersive visual experience to the subject during use which guides interaction of the subject with the receiving surface. Examples of such user interfaces have been described in detail hereinabove.

As will be understood, such methods may be performed using a device as defined hereinabove.

As will be understood, in certain embodiments devices as described herein may be configured for directionality and/or specificity suitable for performing a variety of exercises and/or assessments of a variety of body regions and/or joint mechanics (for example, rotational joints, flexion/extension joints, etc. . . . ) or other suitable joint of musculotendinous group. Devices described herein may, in certain embodiments, be configured for 360° positioning of the receiving surface about the subject, providing a contact point at any suitable location about the circumference of the cranium, for example. The arced or curved guide arm may also allow, via for/aft motion, another degree of freedom which may allow for multiple contact points on the cranium at virtually any point within the 360° circumference of the head. By way of example, in direct forward flexion) (0°/360°, the receiving surface may contact the forehead at the most cephalad point, mid forehead, or along the brow. Similar scenarios may occur throughout the 360° circumference depending on device configuration. In such manner, capacity of device embodiments described herein may be suitable to potentially strengthen larger or smaller muscle groups, and/or deep and/or superficial muscle groups of the neck. In certain embodiments, a level of finite control may be enhanced by changing the width and/or shape of the load cell or input sensor. As such, in certain embodiments, the load cell or input sensor, or the pad with such sensor integrated therewith, may be interchangeable, allowing the user and/or clinician to adapt the device to the particular clinical setting and tolerances as needed or desired.

In certain embodiments, devices described herein may be pre-programmed to provide particular strength parameters for the user to experience (i.e. 2 lbs, 10 lbs, 50 lbs, etc. . . . ), thereby allowing for substantially continuous even distribution of force in a specific direction. If, for example, the subject is expected to apply 5 lbs of force to the sensor pad and fails to do so (for example, if the subject applied only 3 lbs of force), the motor may be programmed to not engage. As well, if at any point along the path of the strengthening direction the subject failed to apply the programmed force amount, the motors may be configured to disengage with no recoil, thereby increase safety. Further, it is contemplated that in certain embodiments, devices as described herein may allow for isometric and isokinetic strengthening protocols to be utilized in the same workout scenario, for example. In certain embodiments, isokinetic treatment may take the form of concentric and/or an eccentric strengthening protocol.

As will be understood, in certain embodiments the utilization of AR (for example, via an MPU) may provide for reproducibility, consistency, and/or precision for the individual muscle or muscle group being strengthened or assessed. Where, for example, the neck is to be exercised or assessed, the subject may, for example, place their head in a proper (pre-determined or pre-programmed) position for the workout to begin. On completion of the first repetition, the AR/MPU may in certain embodiments ensure that the individual assumes the same position to commence the second repetition. Position sense of the upper torso may, in certain embodiments, by stabilized using a harness, or by combining another MPU on the shoulders, for example.

In certain embodiments, it is further contemplated that embodiments of devices described herein may be used to assess minimum/maximum tolerances that are typically utilized in WCB functional capacity evaluations. For example, in certain embodiments a device as described herein may be configured for a user to (in the case of MVA and WCB cases) precisely orient the subject's head and, using an input sensor-equipped receiving surface, determine the minimum and maximum pain tolerances correlated with a weight challenge in that direction.

In certain embodiments, devices as described herein may provide a graphical representation of data collected for a user, which may be used to compare for normative data for the age and/or sex of the user. Further, a graphical representation may be made to compare an initial evaluation or session with a subsequent evaluation or session. Captured data may provide insight on strength gains in healthy subjects (i.e. athletes), or in rehab settings, for example. It is contemplated that, in certain embodiments, data capture may facilitate delineating unexpected movement scenarios such as in malingering cases, for example.

As will also be understood, the devices and methods described hereinabove have been discussed in the context of analysis and/or exercise of a neck region of a subject; however, it is also contemplated that such devices and methods may be adapted for analysis and/or exercise of other muscles or muscle groups or joints of the body. In certain embodiments, such devices and methods may be adapted for analysis and/or exercise of a variety of body regions and/or joint mechanics (for example, rotational joints, flexion/extension joints, etc. . . . ) or other suitable joint or musculotendinous group. The person of skill in the art having regard to the teachings herein will be able to adapt devices and methods described herein in to suit the particular body region, joint, muscles, or muscle groups of interest. By way of example, the support frame may be adapted to receive the subject and position the receiving surface near a different body region of interest of the subject (such as, for example, the subject's arm, hand, leg, foot, jaw, or other suitable region), and the guide arm may be adapted to guide the receiving surface along an arc or other path suitable for exercise and/or analysis of the body region of interest. It will be recognized that the motor assembly, and function thereof, as described herein may be applied to exercise and/or analysis of a variety of suitable body regions of interest and is not limited to the head/neck region. Performance of exercise and/or analysis of muscle(s) or muscle groups using devices and methods which may allow for controlled application of force during use, protecting against "snap back" injury, may be of interest in a wide variety of applications. Devices and methods which may provide isometric exercise, isokinetic exercise, or both, to the subject during use, and/or may allow for assessment of muscle function, range of motion, or both, of the subject during use, may also be of interest in a variety of applications. In certain embodiments, it is contemplated that embodiments of devices as described herein may be employed for strengthening and/or assessing body parts such as, for example, the shoulder, or the TMJ, for example.

As such, in certain embodiments, there is provided herein a device for analysis and/or exercise of a body region of a subject, the device comprising:
 a support frame;
 a guide arm supported by the support frame;
 a receiving surface supported by the guide arm, the receiving surface for receiving input force from the subject; and
 a motor assembly in communication with the guide arm, the motor assembly controlling movement of the receiving surface with respect to the subject based on input force received from the subject at the receiving surface.

In another embodiment, the guide arm may be a curved guide arm.

In yet another embodiment, the body region of the subject may be a head, neck, arm, hand, leg, foot, jaw, or other suitable body region of the subject.

In still another embodiment, there is provided herein a method for exercising or analyzing a body region of a subject, the method comprising:
- instructing the subject to apply an input force to a receiving surface;
- sensing the input force applied to the receiving surface over time; and
- controlling movement of the receiving surface with respect to the subject based on the input force received from the subject at the receiving surface using a motor assembly,
- whereby the motor assembly moves the receiving surface in a direction substantially aligned with the input force at a predetermined rate, so long as the input force remains within an allowable tolerance, thereby exercising or analyzing function of the body region. The motor assembly may perform such action until, for example, a pre-determined or pre-set end position or suitable stopping point for the receiving surface is reached.

In yet another embodiment, the body region of the subject may be a head, neck, arm, hand, leg, foot, jaw, or other suitable body region of the subject.

FIGS. 30 and 31 depict an embodiment of a device as described herein, configured for exercise and/or assessment of the elbow or bicep while in use by a user. FIGS. 32 and 33 depict an embodiment of a device as described herein, configured for exercise and/or assessment of the shoulder while in use by a user. The depicted embodiments may provide for a degree of safety, since they do not actuate through 360°, and instead mechanically operate through the stroke length of the curved guide arm. Since a large arc length curved guide arm, and a small drive wheel, are used in these embodiments, even a small motor may be sufficient to deliver large loads, thereby decreasing cost. Wireless load cell-based input sensors are included in the depicted receiving surfaces (i.e. pads), providing for accuracy of results in these embodiments. As well, such devices may be configured for operation while seated, or lying in bed, due to the "hollow axis" of the device, facilitating setup for a variety of joint mechanics (i.e. rotational joints, flexion/extension joints, etc. . . . ) of the body.

Example 1—Device Electrical Layout Example

FIG. 21 provides an example of an electrical layout for an embodiment of a device as described herein. As will be understood, this Example is provided for illustrative purposes intended for the person of skill in the art. It will be understood that various substitutions, deletions, additions, or modifications may be made to suit a particular application, and that the following examples are not intended to be limiting.

The depicted example includes a main power switch (26) including fuses from an AC wall adaptor, and AC to DC power adaptors (27) for different electrical components of the device as shown. A plug (28) is shown, which is positioned on the outside of the device for charging external devices such as a table computer and/or AR glasses. A tablet interface (29) for control of the device is provided. Furthermore, the depicted scheme includes a circuit control (30) for a vertical positioning actuator. The device microcontroller (35) may use manual input buttons (32) to raise or lower the upper assembly of the device for different user heights. The power may be routed through a safety relay hard wired to a machine emergency stop (51). In the depicted example, a linear actuator (31) is used to lift the entire upper assembly for users of different height, controlled by control circuit (30). Mechanical "up" and "down" buttons (7) are provided on the device, allowing for adjustment of the position of the vertical linear actuator (31). The signal from these buttons is routed through the device's on-board microcontroller (35) for added control. In the depicted example, a large button (33) is provided, positioned under the curved guide arm motor assembly portion of the device, such that if the machine upper assembly is lowered too far and contacts the head of the user, the button/switch (33) will prevent further lowering of the machine onto the user. The depicted embodiment further includes visual indicator lights (34) showing device status.

As well, the embodiment includes an on-board microcontroller (35) as referenced above. Transceiver (36), such as a Bluetooth (or other suitable wireless communication) or Xbee Wifi transceiver, is provided, which enables the microcontroller (35) to communicate with other wireless element(s) of the device.

The device additionally includes a targeting lamp (37) which indicates the center of rotation of the curved guide arm. This assists in setting the center of rotation about the desired joint of the user. A transceiver (38) is also provided, such as an RS485 or Ethernet transceiver, which allows microcontroller communication with network-enabled motors.

A vertical axis rotational motor (39) is provided which is powered and which is controlled by microcontroller (35) through transceiver (38). This motor drives the curved guide arm (with pad) away/toward the user during use (i.e. changes the vertical axis angle). A further rotational motor (40) is provided which is also powered, and which is also controlled by microcontroller (35) through transceiver (38). The second motor (40) drives rotation of the curved guide arm (with pad) around the periphery of the user (i.e. drives the receiving surface about the horizontal axis or arc angle). An optional third accessory motor (41) may be provided for automated adjustment of receiving surface positioning (i.e. for moving the receiving surface closer to or further from the curved guide arm to accommodate user height/positioning). The third motor (41), if present, is powered and is controlled by microcontroller (35) through transceiver (38). Operation of third motor (41) is shown in FIG. 22. Alternatively, such adjustment may be manual or mechanical, for example via mechanical detents. The depicted configuration includes wireless visual immersive glasses (42), such as augmented reality or virtual reality glasses, goggles, or headset.

The receiving surface of the depicted configuration includes an input sensor in the form of a load cell (43) located in the receiving surface to indicate pressing force of the user during use of the device. An optional extra load cell (44) may be provided, located in the receiving surface, to indicate pressing force of the user during use of the device, giving further precision through use of more than one load cell. The device further includes a microcontroller (45) for processing load cell data from (43), and passing the data to the radio transceiver (46). Transceiver (46), such as a Bluetooth (or other suitable wireless communication) or Xbee WiFi transceiver, may enable load cell data to be sent to any other suitable transceiver on the device. A motion processing chip (47) is also provided, which gives relative positioning to microcontroller (48). This may be used at any suitable body position to track and/or maintain user conformity and/or correct user positioning. Microcontroller (48) processes the data from MPU (47), and then passes that positional data to transceiver (49). Transceiver (49), such as a Bluetooth (or other suitable wireless communication) or XBee WiFi transceiver, enables the positional data to be sent to any other suitable transceiver on the device. (50) depicts an embodiment of (47), (48), and (49), in which motional capturing units may be used to facilitate correct body positioning during exercise. A machine emergency stop (51) is included, which may be used to halt any actuation of the device if pressed.

Example 2—Example of a Neck Exercise Device

FIGS. 23-27 depict another example of an embodiment of a device as described herein, in this example used for neck exercise and/or assessment. As will be understood, this Example is provided for illustrative purposes intended for the person of skill in the art. It will be understood that various substitutions, deletions, additions, or modifications may be made to suit a particular application, and that the following examples are not intended to be limiting.

In the depicted device example, as shown in FIG. 23, the device includes a curved guide arm (52) having a receiving surface including input sensors (push pad and wireless load cells (53)) attached thereto via an arm (56) of adjustable length. The curved guide arm is driven toward/away from the user by a motor assembly supported above the user via the support frame. The lower portion of the motor assembly includes a large safety stop pad (54) which assists with height adjustment safety by preventing the upper portion of the device from lowering toward the user when the stop pad (54) is contacted with the user's head. A second motor (55) is provided which drives a belt to rotate the curved guide arm/receiving surface peripherally about the user (i.e. around the vertical axis).

As seen in FIG. 24, the motor assembly of the device further includes side guide rollers (57) interacting with the curved guide arm, and pinch roller compression springs (58). The motor (59) of the motor assembly is connected with a drive belt as shown to drive motion of the curved guide arm. Vertical axis bearings (60) are also depicted, which facilitate rotation of the curved guide arm about the vertical axis.

As depicted in FIG. 25, the device includes a support frame including a vertical frame assembly (61), with an internal electronics mounting plate (62). A rotational wiring harness (63) is also provided to accommodate device motion. End stops (64) are included, to restrict motion of the curved guide arm beyond a predetermined position. A ball joint (65) is included to assist with positioning of the load cells during use. The adjustable arm (56) is also depicted.

FIG. 26 depicts the rear of the device, and shows a tablet control interface (66), user seat (67), power adaptor (68), and main switch and power plug (69). The upper portion of the support frame (as well as the motor assembly, curved guide arm, and receiving surface) of the device can be raised or lowered to accommodate user dimensions and activity to be performed. A vertical actuator (70) is provided for such raising or lowering, as well as linear bearings (71). Vertical actuator control buttons (72) may be used for raising or lowering accordingly.

FIG. 27 depicts the upper portion (73) of the support frame of the device which may be raised or lowered as described above to raise or lower the curved guide arm (52) with respect to the user. An emergency stop button (74) is provided for user safety, and a pivot post (75) is provided which allows orientation of the control tablet toward a user, or toward a clinician. A base assembly (75) supports the upper portion (73) and houses the vertical actuator.

FIG. 28 provides a rendering of a device embodiment similar to those depicted in FIGS. 23-27.

FIG. 29 depicts a variant of the above-described devices, in which the device is a wall-mounted device, with the upper portion including the guide arm being raised or lowered along a support rail stationed against the wall. The depicted embodiment is a simplified version of that depicted in FIG. 23 and is design to be more cost-effective by omitting a vertical actuator (i.e. height adjustment is manual). The rotational motor for rotating the guide arm/receiving surface around the periphery of the user may also be omitted in certain embodiments, depending on intended application.

Although the invention has been illustrated and described in greater detail with reference to the preferred exemplary embodiment, the invention is not limited to the examples disclosed, and further variations can be inferred by a person skilled in the art, without departing from the scope of protection of the invention.

For the sake of clarity, it is to be understood that the use of "a" or "an" throughout this application does not exclude a plurality, and "comprising" does not exclude other steps or elements.

The invention claimed is:

1. A device for analysis and/or exercise of a neck region of a subject, said device comprising:
   a support frame;
   a curved guide arm supported by the support frame;
   a receiving surface supported by the curved guide arm, the receiving surface for receiving input force from the subject; and
   a motor assembly in communication with the curved guide arm, the motor assembly controlling movement of the receiving surface with respect to the subject based on input force received from the subject at the receiving surface;
     wherein the motor assembly is configured to move the receiving surface in a direction substantially aligned with the input force at a predetermined rate, so long as the input force remains within an allowable tolerance, until a pre-determined end position is reached;
     wherein the motor assembly is configured to stop movement of the receiving surface with respect to the subject upon interruption of the input force from the subject upon the receiving surface, upon failure of the input force to remain within an allowable tolerance, upon reaching a pre-determined end position, or any combination thereof, or both; and
     wherein the allowable tolerance comprises a lower threshold value for the input force to exceed, an upper threshold value for the input force to not exceed, an acceptable direction vector range for the input force to align within, or any combination thereof.

2. The device according to claim 1, wherein:
   the receiving surface is fixedly mounted to or integrated with the curved guide arm, and the motor assembly is mounted to the support frame and controls movement of the curved guide arm, such that movement of the receiving surface with respect to the subject is controlled by movement of the curved guide arm by the motor assembly; or the receiving surface is movably mounted to the curved guide arm, and the motor assembly is mounted to the curved guide arm and controls movement of the receiving surface along the curved guide arm, such that movement of the receiving surface with respect to the subject is controlled by movement of the receiving surface along the curved guide arm by the motor assembly.

3. The device according to claim 2, wherein the motor assembly engages with the curved guide arm via one or more non-slip complementary engagement members located on the motor assembly and curved guide arm.

4. The device according to claim 1, wherein the device further comprises one or more input sensors for sensing input force received from the subject at the receiving surface and transmitting a control signal based on said input force, and a controller for receiving the control signal and controlling action of the motor assembly based on the control signal.

5. The device according to claim 4, wherein at least one input sensor is located at the receiving surface.

6. The device according to claim 1, wherein the device further comprises a user interface for guiding the subject's interaction with the receiving surface during use, wherein the user interface instructs the subject to apply input force to the receiving surface in a specific manner, and provides the subject with real-time feedback allowing the subject to adjust application of input force so as remain within an allowable tolerance, wherein the allowable tolerance comprises a lower threshold value for the input force to exceed, an upper threshold value for the input force to not exceed, an acceptable direction vector range for the input force to align within, or any combination thereof.

7. The device according to claim 6, wherein the user interface comprises a graphical interface displayed to the subject during use, an auditory interface played for the subject during use, or a combination thereof.

8. The device of claim 6, wherein the user interface comprises a graphical user interface which provides an immersive visual experience to the subject during use which guides interaction of the subject with the receiving surface.

9. The device according to claim 1, wherein the device further comprises a positioning sensor which tracks location of the receiving surface, head positioning of the subject, or both, in 3D space.

10. The device according to claim 1, wherein the curved guide arm is rotatable with respect to the support frame about a substantially vertical axis, allowing for positioning of the receiving surface about at least a portion of an outer perimeter region surrounding the subject.

11. The device according to claim 1, wherein the device comprises a seat for the subject which orients the neck region of the subject with the receiving surface.

12. The device according to claim 1, wherein the motor assembly controls movement of the receiving surface with respect to the subject so as to provide isometric exercise, isokinetic exercise, or both, to the subject during use so as to assess range of motion of the subject during use; or a combination thereof.

13. A method for exercising or analyzing a neck region of a subject, said method comprising:

instructing the subject to apply an input force to a receiving surface;

sensing the input force applied to the receiving surface over time; and controlling movement of the receiving surface with respect to the subject based on the input force received from the subject at the receiving surface using a motor assembly, whereby the motor assembly moves the receiving surface away from or toward the subject in a direction substantially aligned with the input force, or in a pre-determined direction, at a predetermined rate, so long as the input force remains within an allowable tolerance, until a pre-determined end position is reached, thereby exercising or analyzing function of the neck region; and wherein the allowable tolerance comprises a lower threshold value for the input force to exceed, an upper threshold value for the input force to not exceed, an acceptable direction vector range for the input force to align within, or any combination thereof.

14. The method according to claim 13, wherein the motor assembly stops movement of the receiving surface with respect to the subject upon sensed interruption of the input force from the subject upon the receiving surface, upon sensed failure of the input force to remain within the allowable tolerance, upon reaching a pre-determined end position, or any combination thereof.

15. The method according to claim 13, wherein the method further comprises tracking location of the receiving surface, head positioning of the subject, or both, in 3D space over time.

16. The method according to claim 13, wherein the motor assembly controls movement of the receiving surface with respect to the subject so as to provide isometric exercise, isokinetic exercise, or both, to the subject, so as to assess range of motion of the subject, or a combination thereof.

17. The method according to claim 13, wherein the instructing step comprises providing a user interface guiding the subject's interaction with the receiving surface, wherein the user interface instructs the subject to apply input force to the receiving surface in a specific manner, and provides the subject with real-time feedback allowing the subject to adjust application of input force so as remain within the allowable tolerance, and wherein the user interface comprises a graphical user interface which provides an immersive visual experience to the subject during use which guides interaction of the subject with the receiving surface.

* * * * *